US006531479B2

(12) United States Patent
Wang et al.

(10) Patent No.: US 6,531,479 B2
(45) Date of Patent: Mar. 11, 2003

(54) ANTI-CANCER COMPOUNDS

(75) Inventors: Shudong Wang, Angus (GB); Peter M. Fischer, Angus (GB)

(73) Assignee: Cyclacel Limited (GB)

( * ) Notice: Subject to any disclaimer, the term of this patent is extended or adjusted under 35 U.S.C. 154(b) by 0 days.

(21) Appl. No.: 09/823,075

(22) Filed: Mar. 29, 2001

(65) Prior Publication Data

US 2002/0019404 A1 Feb. 14, 2002

(30) Foreign Application Priority Data

Mar. 29, 2000 (GB) ............................. 0007636
Jun. 20, 2000 (GB) ............................. 0015117

(51) Int. Cl.⁷ .................. A61K 31/506; A61K 31/427; C07D 239/02; C07D 417/00; C07D 277/22
(52) U.S. Cl. ................. 514/275; 514/365; 544/330; 544/331; 548/146; 548/202; 548/203; 548/205
(58) Field of Search ................ 514/275, 365; 544/330, 331; 548/146, 202, 203, 205

(56) References Cited

U.S. PATENT DOCUMENTS

| 5,516,775 A | 5/1996 | Zimmermann et al. .. 514/224.2 |
| 6,107,301 A | 8/2000 | Aldrich et al. .............. 514/258 |

FOREIGN PATENT DOCUMENTS

| EP | 164 204 | 12/1985 |
| EP | 233 461 | 8/1987 |
| EP | 739 341 | 10/1996 |
| WO | WO 95/09847 | 4/1995 |
| WO | WO 95/09852 | 4/1995 |
| WO | WO 95/19358 | 7/1995 |
| WO | WO 97/19065 | 5/1997 |
| WO | WO 00/12485 | 3/2000 |

OTHER PUBLICATIONS

Zimmerman er al;Phenyl–pytimidine(PAP) derivatives . . . protein kinase C(PKC);Arch Pharm.329/7,371(1996).*
Zimmermann et al;Phenylamino–pyrimidine(PAP) derivative . . . protein kinase C (PKC);Arch.Pharm.329/7, 371(1996).*
Paul, R. et al., "Preparation of substituted N–phenyl–4–aryl–2–pyrimidinamines as mediator release inhibitors,"*J. Med. Chem.* Sep. 17, 1993;36(19):2716–25.
Zimmermann, J. et al., "Phenylamino–pyrimidine (PAP) derivatives: a new class of potent and selective inhibitors of protein kinase C (PKC)," *Arch. Pharm.* (Weinheim). Jul. 1996;329(7):371–6.

* cited by examiner

*Primary Examiner*—Richard L. Raymond
*Assistant Examiner*—Sudhaker B. Patel
(74) *Attorney, Agent, or Firm*—Lahive & Cockfield LLP; Giulio A. DeConti, Jr.; Cynthia L. Kanik

(57) ABSTRACT

The present invention relates to 2-substituted 4-heteroaryl-pyrimidines, their preparation, pharmaceutical compositions containing them and their use as inhibitors of cyclin-dependent kinases (CDKs) and hence their use in the treatment of proliferative disorders such as cancer, leukaemia, psoriasis and the like.

23 Claims, 14 Drawing Sheets

ANTI-CANCER COMPOUNDS

The present invention relates to 2-substituted 4-heteroaryl-pyrimidines, their preparation, pharmaceutical compositions containing them, and their use in the treatment of proliferative disorders such as cancer, leukemia, psoriasis and the like.

BACKGROUND TO THE INVENTION

Certain 4,5,6-substituted-N-(substituted-phenyl)-2-pyrimidineamines having anti-asthmatic properties are disclosed in EP-A-233,461. Certain 4-heteroaryl-N-(3-substituted-phenyl)-2-pyridineamines possessing antiproliferative properties and inhibiting protein kinases C, epidermal growth factor receptor-associated tyrosine protein kinase (EGF-R-TPK), as well as CDK1/cyclin B have been disclosed in WO95/09847 wherein the exemplified heteroaryl are pyridyl and indolyl.

J. Med. Chem. (1993) Vol. 36, pages 2716–2725, Paul, R. et al: discloses a further class of phenyl amino-pyrimidines possessing anti-inflammatory activity. These compounds include mono-substituted 2-thienyl groups at the 4-position of the pyrimidine ring and dimethyl-3-furyl groups at this position.

It is an aim of the present invention to provide a further class of N-phenyl-2-pyrimidine anti-proliferative compounds. The compounds of the present invention have surprisingly been found to not to be inhibitors of protein kinase C. As discussed hereinafter, their activity may be demonstrated by inhibition of cell proliferation in cell lines and/or inhibition of cyclin dependent kinase enzymes. Throughout the specification, the term "thienyl" is used interchangeably with "thiophene"

SUMMARY OF THE INVENTION

The first aspect of the present invention relates to compounds of general formula I:

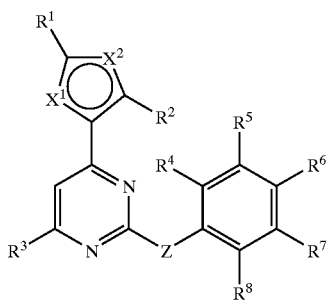

wherein:
$X^1$ is CH and $X^2$ is S; or
one of $X^1$ and $X^2$ is S, and the other of $X^1$ and $X^2$ is N;
Z is NH, NHCO, NHSO$_2$, NHCH$_2$, CH$_2$, CH$_2$CH$_2$, or CH=CH;
$R^1$, $R^2$, and $R^3$ are independently H, alkyl, aryl, aralkyl, heterocycle, halogeno, NO$_2$, CN, OH, alkoxy, aryloxy, NH$_2$, NH—R', N—(R')(R"), NH—COR', NH-aryl, N-(aryl)$_2$, COOH, COO—R', COO-aryl, CONH$_2$, CONH—R', CON—(R')(R"), CONH-aryl, CON-(aryl)$_2$, SO$_3$H, SO$_2$NH$_2$, CF$_3$, CO—R', or CO-aryl, wherein alkyl, aryl, aralkyl, heterocycle and NH-aryl groups may be further substituted with one or more groups selected from halogeno, NO$_2$, CN, OH, O-methyl, NH$_2$, COOH, CONH$_2$ and CF$_3$; at least one of the groups $R^1$ and $R^2$ being other than H when either $X^1$ or $X^2$ is S;

$R^4$, $R^5$, $R^6$, $R^7$, and $R^8$ are independently from each other H, substituted or unsubstituted lower alkyl, halogeno, NO$_2$, CN, OH, substituted or unsubstituted alkoxy, NH$_2$, NH—R', alkyl-aryl, alkyl-heteroaryl, NH(C=NH)NH$_2$, N(R')$_3^+$, N—(R')(R"), COOH, COO—R', CONH$_2$, CONH—R', CON-(R')(R"), SO$_3$H, SO$_2$NH$_2$, CF$_3$ or (CH$_2$)$_n$O(CH$_2$)$_m$NR'R", (CH$_2$)$_n$CO$_2$ (CH$_2$)$_m$OR'" wherein n is 0, 1, 2 or 3 and m is 1, 2 or 3;

wherein R', R" and R'" are each independently alkyl groups that may be the same or different;
and pharmaceutically acceptable salts thereof.

DESCRIPTION OF THE FIGURES

FIG. 6 shows human lung carcinoma cells (A549) treated for 16 h with 10 μM compound 28. Extensive cytoplasmic vaculation is observed in the treated cell (A) but not in the control cells (B).

DESCRIPTION OF THE PREFERRED EMBODIMENTS

Figure 1:
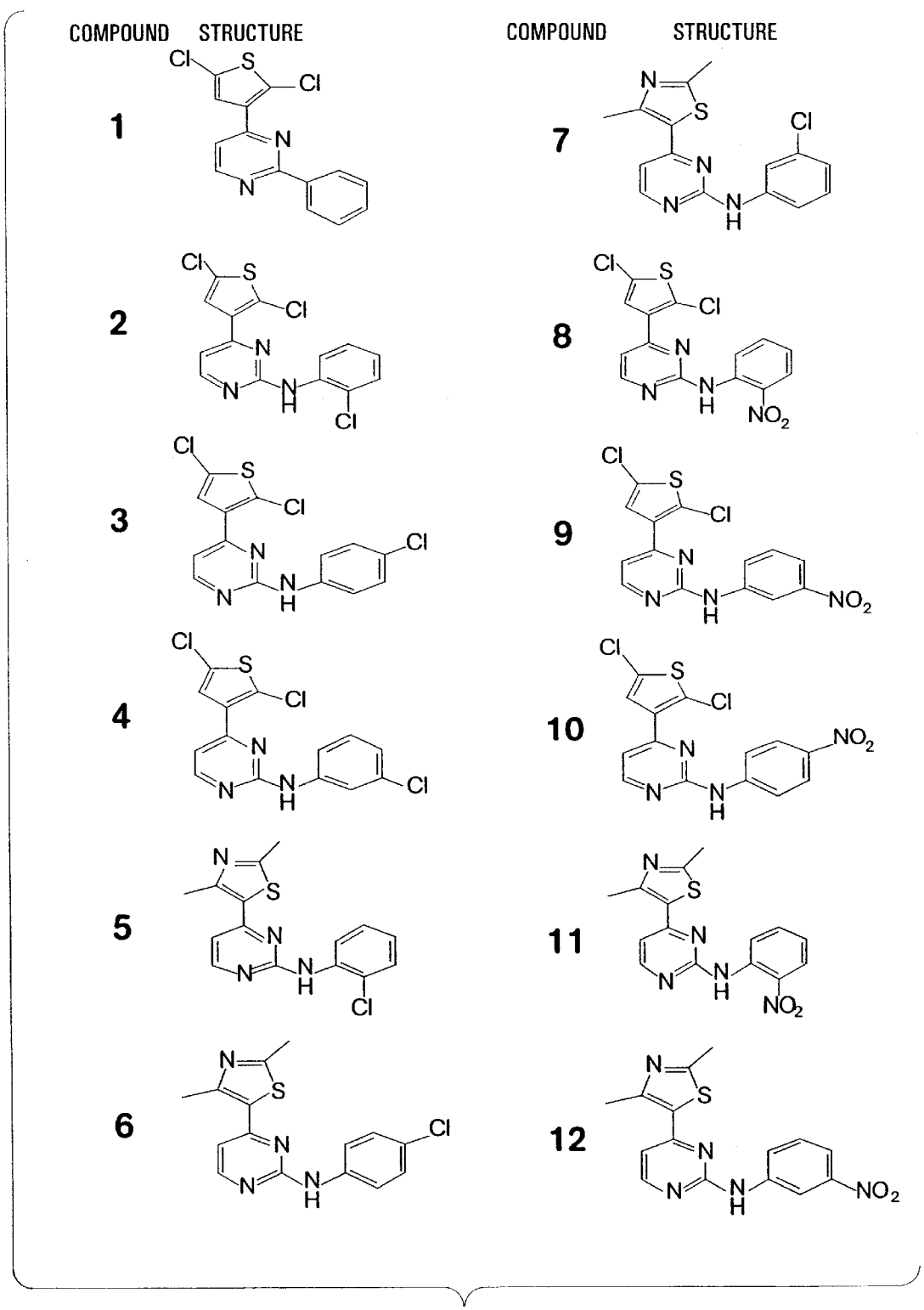
FIG. 1 shows the chemical structure of compounds 1–119 according to the invention.
Figures 1, 2:
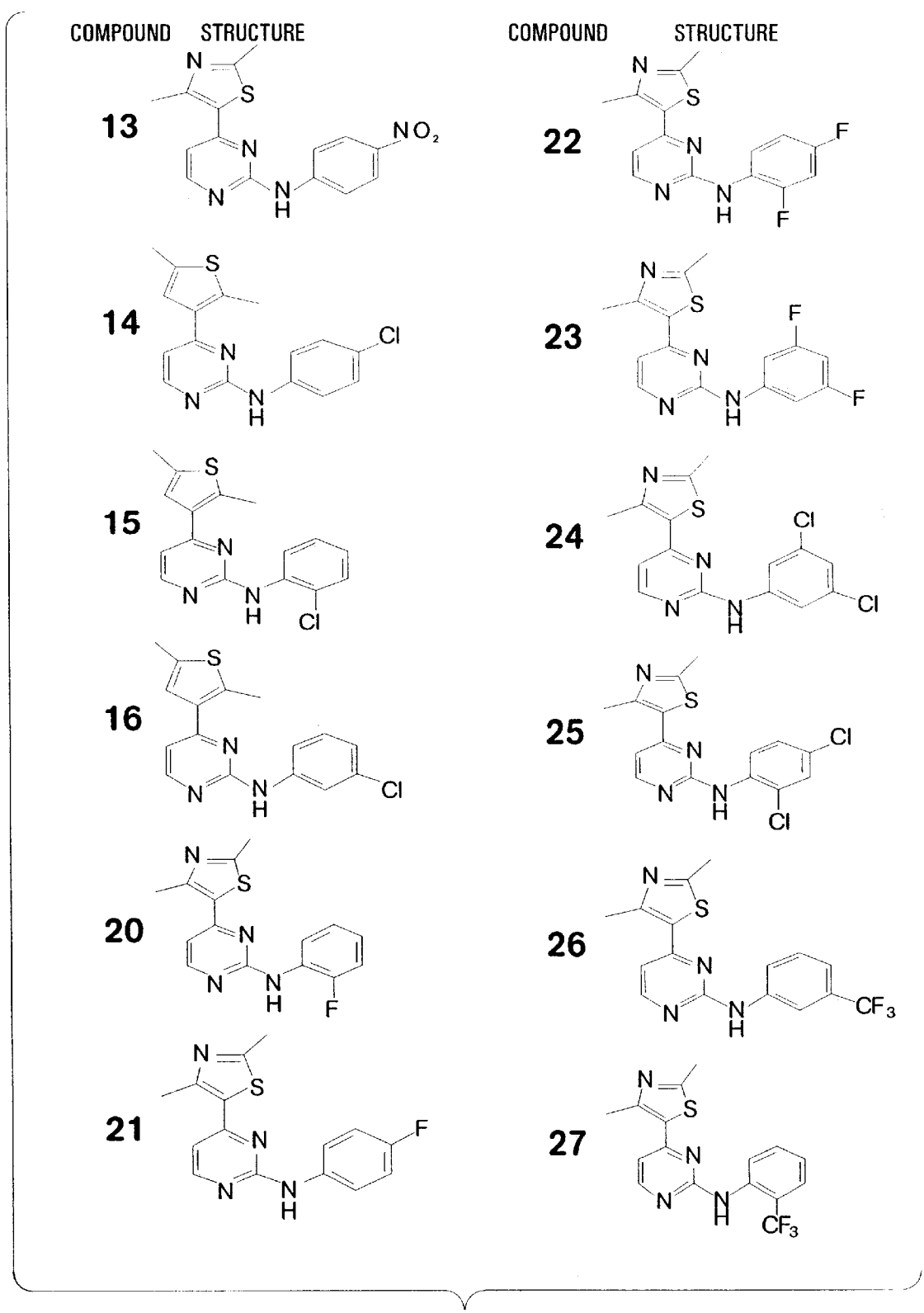
FIG. 2 shows the mitotic arrest and induction of apoptosis by compound 28 in Saos-2 cells. Cells were treated with 1 μM compound 28 for 48 h. Mitotic and apoptotic cells are indicated by the arrows.

As used herein the term "alkyl" includes both straight chain and branched alkyl groups having from 1 to 8 carbon atoms, e.g. methyl, ethyl propyl, isopropyl, butyl, isobutyl, tert-butyl, pentyl, hexyl etc. and the term "lower alkyl" is similarly used for groups having from 1 to 4 carbon atoms.

The term "aryl" is used to include groups having from 6 to 10 carbon atoms, e.g. phenyl, naphthyl etc.

The term "aralkyl" is used as a conjunction of the terms alkyl and aryl as given above.

This invention provides a compound of general formula I:

$$\text{I}$$

(structural formula showing a thiazole/thiophene ring with $R^1$, $X^1$, $X^2$, $R^2$ substituents connected to a pyrimidine ring bearing $R^3$, linked via Z to a phenyl ring with $R^4$, $R^5$, $R^6$, $R^7$, $R^8$ substituents)

wherein:
$X^1$ is CH and $X^2$ is S; or
one of $X^1$ and $X^2$ is S, and the other of $X^1$ and $X^2$ is N;
Z is NH, NHCO, NHSO$_2$, NHCH$_2$, CH$_2$, CH$_2$CH$_2$, or CH=CH;
$R^1$, $R^2$, and $R^3$ are independently H, alkyl, aryl, aralkyl, heterocycle, halogeno, NO$_2$, CN, OH, alkoxy, aryloxy, NH$_2$, NH—R', N—(R')(R"), NH—COR', NH-aryl, N-(aryl)$_2$, COOH, COO—R', COO-aryl, CONH$_2$, CONH—R', CON—(R')(R"), CONH-aryl, CON-(aryl)$_2$, SO$_3$H, SO$_2$NH$_2$, CF$_3$, CO—R', or CO-aryl, wherein alkyl, aryl, aralkyl, heterocycle and NH-aryl groups may be further substituted with one or more groups selected from halogeno, NO$_2$, CN, OH, O-methyl, NH$_2$, COOH, CONH$_2$ and CF$_3$; at least one of the groups $R^1$ and $R^2$ being other than H when either $X^1$ or $X^2$ is S;
$R^4$, $R^5$, $R^6$, $R^7$, and $R^8$ are independently from each other H, substituted or unsubstituted lower alkyl, halogeno, NO$_2$, CN, OH, substituted or unsubstituted alkoxy, NH$_2$, NH—R', alkyl-aryl, alkyl-heteroaryl, NH(C=NH)NH$_2$, N(R')$_3^+$, N—(R')(R"), COOH, COO—R', CONH$_2$, CONH—R', CON—(R')(R"), SO$_3$H, SO$_2$NH$_2$, CF$_3$ or (CH$_2$)$_n$O(CH$_2$)$_m$NR'R", (CH$_2$)$_n$CO$_2$(CH$_2$)$_m$OR'" wherein n is 0, 1, 2 or 3 and m is 1, 2 or 3;
wherein R', R" and R'" are each independently alkyl groups that may be the same or different;
and pharmaceutically acceptable salts thereof.

This invention further provides the above compound, wherein;
$X^1$ and $X^2$ are S and N respectively, or CH and S respectively;
$R^1$, $R^2$ and $R^3$ are each independently selected from H, alkyl, aryl, aralkyl, halogeno, NO$_2$, CN, OH, alkoxy, aryloxy, NH$_2$, NHCOR', NHCOR', NH-aryl, NH—R', N—(R')(R"), COOH, COO—R', CONH$_2$, CONH—R', CON—(R')(R"), SO$_3$H, SO$_2$NH$_2$, CF$_3$, and CO—R' wherein alkyl, aryl, NH-aryl and aralkyl groups may be further substituted with one or more groups selected from halogeno, NO$_2$, CN, OH, O-methyl, NH$_2$, COOH, CONH$_2$ and CF$_3$;
Z is selected from N, NHSO$_2$ and NHCH$_2$;
$R^4$-$R^8$ are each independently selected from H, OH, halogeno, nitro, amino, alkoxy, carbamoyl, sulfamyl, C$_{1-4}$ alkyl, substituted C$_{1-4}$ alkyl, COOH, COOR', CN, CF$_3$, (CH$_2$)$_n$O(CH$_2$)$_m$NR'R", alkyl-aryl, alkyl-heteroaryl, NH(C=NH)NH$_2$, N(R')$_3^+$, N(R')(R") and (CH$_2$)$_n$CO$_2$(CH$_2$)$_m$OR'".

In an embodiment of the above compounds, $X^1$ and $X^2$ are S and N respectively.

In another embodiment of the above compounds, Z is NH and $R^3$ is H.

Included within the scope of this invention are the above compounds, wherein $R^1$ and $R^2$ are each independently one or more of halogeno, a C$_{1-4}$ alkyl group, H, aryl, heterocycle or NH(R').

In an embodiment of the above compounds, $R^1$ and $R^2$ are both chloro or methyl.

In another embodiment of the above compounds, $R^3$ is selected from H, aryl, substituted aryl, halo, C$_{1-4}$ alkoxy and OH.

This invention includes the above compounds wherein $R^4$ to $R^8$ are selected independently from F, NH$_2$, NO$_2$, OH, Cl, Br, I, CF$_3$, OMe, COOH, COOR', CN, H, C$_{1-4}$ alkyl, C$_{1-4}$ alkoxy, CH$_2$CO$_2$CH$_2$CH$_2$OMe, NH(C=NH)NH$_2$, and CO$_2$CH$_2$CH$_2$OMe, CH$_2$OCH$_2$CH$_2$NEt$_2$, CH$_2$-heteroaryl, NMe$_3^+$, NMe$_2$.

This invention features a compound selected from;
(a) 2-{N-(phenyl)}-4-(2,4-dimethylthiazol-5-yl) pyrimidineamines in which the phenyl group is 2-, 3- or 4-substituted by at least one of Me, F, NH$_2$, NO$_2$, OH, Cl, Br, I, CF$_3$, OMe, CN, COOH, CH$_2$OH, COOMe, COOEt, NH(C=NH)NH$_2$, CH$_2$CO$_2$CH$_2$CH OMe, CH$_2$-pyridyl, CH$_2$OCH$_2$CH$_2$NEt$_2$, CO$_2$CH$_2$CH$_2$OMe, NMe$_3^+$ and NMe$_2$;
(b) 2-{N-(phenyl)}-4-(2,5-dichloro-thien-3-yl) pyrimidineamines in which the phenyl group is 2-, 3- or 4-substituted by at least one of F, NO$_2$, OH, Cl, or OMe;
(c) 2-{N-(phenyl)}-4-(2,5-dimethyl-thien-3-yl) pyrimidineamines in which the phenyl group is 2-, 3- or 4-substituted by at least one of F, NO$_2$, OH, Cl, or OMe, and
(d) 2-{N-(phenyl)}-4-(4-methyl-2-methylamino-thiazol-5-yl)pyrimidineamines in which the phenyl group is 2-, 3- or 4-substituted by at least one of F, OH, I, NO$_2$, Cl, COOR', Br, OMe or CF$_3$.

This invention features the above compounds, wherein;
for group (a) the phenyl group is mono-substituted by F, NH$_2$, NO$_2$, OH, Cl, Br, I, CF$_3$, OMe, CN, CH$_2$OH, COOH, COOMe, COOEt, CH$_2$CO$_2$CH$_2$CH$_2$OMe or CO$_2$CH$_2$CH$_2$OMe at any of the 2,3 or 4-positions, or di-substituted by 2,4-difluoro, 3,5-difluoro, 3,4-difluoro, 2,4-dichloro, 3,5-dichloro, 3,4-dichloro, 4-hydroxy-2-nitro, 4-hydroxy-3-nitro, 6-chloro-3-carboxy, 4-chloro-3-carboxy, 6-chloro-2-carboxy, 2-fluoro-4-iodo, 2-hydroxy-4-methoxy, 3-chloro-4-iodo, 3-chloro-4-hydroxy, 3-chloro-4-methyl, 3-chloro-4-methoxy, 4-fluoro-3-nitro, 6-chloro-3-methoxycarbonyl, 3-chloro-4-methoxcarbonyl, 3-chloro-4-ethoxycarbonyl, 2-hydroxy-4-methoxy, 2-chloro-5-methoxycarbonyl, 4-chloro-3-methoxycarbonyl, 6-chloro-3-(CO$_2$CH$_2$CH$_2$OMe), 3-chloro-4-(CO$_2$CH$_2$CH$_2$OMe), 4-chloro-3-trifluoromethyl, or 3-(CO$_2$CH$_2$CH$_2$OMe)-4-fluoro.
for group (b) the phenyl group is mono-substituted by chloro, or, nitro, at any of the 2, 3 or 4-positions;
for group (c) the phenyl group is mono-substituted by chloro at any of the 2, 3 or 4-positions,
for group (d) the phenyl group is mono-substituted by chloro, bromo, iodo, fluoro, OH, nitro, CF$_3$ or OMe at any of the 2, 3 or 4 positions, or disubstituted by 4-hydroxy-3-nitro, 3-chloro-4-ethoxycarbonyl, 3,4-difluoro, 2,4-difluoro, 4-chloro-3-trifluoromethyl or 4-fluoro-3-nitro.
In an embodiment of the above compounds, for group (a) the phenyl group is monosubstituted by Br, I or CF$_3$.

This invention also features one or more compounds selected from;
4-(2,5-Dichloro-thiophen-3-yl)-2-phenyl-pyrimidine,
(2-Chloro-phenyl)-{4-(2,5-dichloro-thiophen-3-yl)-pyrimidin-2-yl}-amine,
(4-Chloro-phenyl)-{4-(2,5-dichloro-thiophen-3-yl)-pyrimidin-2-yl}-amine,
(3-Chloro-phenyl)-{4-(2,5-dichloro-thiophen-3-yl)-pyrimidin-2-yl}-amine,
(2-Chloro-phenyl)-{4-(2,4-dimethyl-thiazol-5-yl)-pyrimidin-2-yl}-amine,
(4-Chloro-phenyl)-{4-(2,4-dimethyl-thiazol-5-yl)-pyrimidin-2-yl}-amine,
(3-Chloro-phenyl)-{4-(2,4-dimethyl-thiazol-5-yl)-pyrimidin-2-yl}-amine,
{4-(2,5-Dichloro-thiophen-3-yl)-pyrimidin-2-yl}-(2-nitro-phenyl)-amine,
{4-(2,5-Dichloro-thiophen-3-yl)-pyrimidin-2-yl}-(3-nitro-phenyl)-amine,
{4-(2,5-Dichloro-thiophen-3-yl)-pyrimidin-2-yl}-(4-nitro-phenyl)-amine,
{4-(2,4-Dimethyl-thiazol-5-yl)-pyrimidin-2-yl}-(2-nitro-phenyl)-amine,
{4-(2,4-Dimethyl-thiazol-5-yl)-pyrimidin-2-yl}-(3-nitro-phenyl)-amine,
{4-(2,4-Dimethyl-thiazol-5-yl)-pyrimidin-2-yl}-(4-nitro-phenyl)-amine,
(4-Chloro-phenyl)-{4-(2,5-dimethyl-thiophen-3-yl)-pyrimidin-2-yl}-amine,
(2-Chloro-phenyl)-{4-(2,5-dimethyl-thiophen-3-yl)-pyrimidin-2-yl}-amine,
(3-Chloro-phenyl)-{4-(2,5-dimethyl-thiophen-3-yl)-pyrimidin-2-yl}-amine,
{4-(2,4-Dimethyl-thiazol-5-yl)-pyrimidin-2-yl}-(2-fluoro-phenyl)-amine,
{4-(2,4-Dimethyl-thiazol-5-yl)-pyrimidin-2-yl}-(4-fluoro-phenyl)-amine,
(2,4-Difluoro-phenyl)-{4-(2,4-dimethyl-thiazol-5-yl)-pyrimidin-2-yl}-amine,
(3,5-Difluoro-phenyl)-{4-(2,4-dimethyl-thiazol-5-yl)-pyrimidin-2-yl}-amine,
(3,5-Dichloro-phenyl)-{4-(2,4-dimethyl-thiazol-5-yl)-pyrimidin-2-yl}-amine,
(2,4-Dichloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-trifluoromethyl-phenyl)-amine,
{4-(2,4-Dimethyl-thiazol-5-yl)-pyrimidin-2-yl}-(2-trifluoromethyl-phenyl)-amine,
{4-(2,4-Dimethyl-thiazol-5-yl)-pyrimidin-2-yl}-(4-trifluoromethyl-phenyl)-amine,
(2-Bromo-phenyl)-{4-(2,4-dimethyl-thiazol-5-yl)-pyrimidin-2-yl}-amine,
(3-Bromo-phenyl)-{4-(2,4-dimethyl-thiazol-5-yl)-pyrimidin-2-yl}-amine,
(4-Bromo-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-trifluoromethyl-phenyl)-amine,
{4-(2,4-Dimethyl-thiazol-5-yl)-pyrimidin-2-yl}-(3-iodo-phenyl)-amine,
{4-(2,4-Dimethyl-thiazol-5-yl)-pyrimidin-2-yl}-(4-iodo-phenyl)-amine,
{4-(2,4-Dimethyl-thiazol-5-yl)-pyrimidin-2-yl}-pyridin-2-yl-amine,
{4-(2,4-dimethyl-thiazol-5-yl)-pyrimidin-2-(3-fluoro-phenyl)-amine,
(3,4-Difluoro-phenyl)-{4-(2,4-dimethyl-thiazol-5-yl)-pyrimidin-2-yl}-amine,
{4-(2,4-dimethyl-thiazol-5-yl)-pyrimidin-2-yl}-(2-methoxy-phenyl)-amine,
{4-(2,4-Dimethyl-thiazol-5-yl)-pyrimidin-2-yl}-(3-methoxy-phenyl)-amine,
{4-(2,4-Dimethyl-thiazol-5-yl)-pyrimidin-2-yl}-(4-methoxy-phenyl)-amine,
3-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-phenol,
N-{4-(2,4-Dimethyl-thiazol-5-yl)-pyrimidin-2-yl}-3-nitro-benzenesulfonamide,
4-Chloro-N-{4-(2,4-dimethyl-thiazol-5-yl)-pyrimidin-2-yl}-benzenesulfonamide,
N-{4-(2,4-Dimethyl-thiazol-5-yl)-pyrimidin-2-yl}-4-fluoro-benzenesulfonamide,
4-{4-(2,4-Dimethyl-thiazol-5-yl)-pyrimidin-2-ylamino}-2-nitro-phenol,
N-{4-(2,4-Dimethyl-thiazol-5-yl)-pyrimidin-2-yl}-4-nitro-benzenesulfonamide,
N-{4-(2,4-Dimethyl-thiazol-5-yl)-pyrimidin-2-yl}-benzene-1,3-diamine,
4-{4-(2,4-Dimethyl-thiazol-5-yl)-pyrimidin-2-ylamino}-benzonitrile,
3-{4-(2,4-Dimethyl-thiazol-5-yl)-pyrimidin-2-ylamino}-benzonitrile,
4-{4-(2,4-Dimethyl-thiazol-5-yl)-pyrimidin-2-ylamino}-benzoic acid methyl ester,
(3-Chloro-4-methyl-phenyl)-{4-(2,4-dimethyl-thiazol-5-yl)-pyrimidin-2-yl}-amine,
(3-Chloro-4-methoxy-phenyl)-{4-(2,4-dimethyl-thiazol-5-yl)-pyrimidin-2-yl}-amine,
4-{4-(2,4-Dimethyl-thiazol-5-yl)-pyrimidin-2-ylamino}-benzoic acid,
{4-Bromo-6-(2,4-dimethyl-thiazol-5-yl)-pyrimidin-2-yl}-(3-nitro-phenyl)-amine,
{4-(2,4-Dimethyl-thiazol-5-yl)-6-phenyl-pyrimidin-2-yl}-(3-nitro-phenyl)-amine,
4-{4-(2,4-Dimethyl-thiazol-5-yl)-6-phenyl-pyrimidin-2-ylamino}-phenol,
(3,4-Difluoro-phenyl)-{4-(4-methyl-2-phenyl-thiazol-5-yl)-pyrimidin-2-yl}-amine,
4-{4-(4-Methyl-2-phenyl-thiazol-5-yl)-pyrimidin-2-ylamino}-phenol,
{4-(2,4-Dimethyl-thiazol-5-yl)-6-phenyl-pyrimidin-2-yl}-(4-fluoro-phenyl)-amine,
(4-Fluoro-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-phenol,
{4-(2,4-Dimethyl-thiazol-5-yl)-6-(4-trifluoromethyl-phenyl)-pyrimidin-2-yl}-(4-fluoro-phenyl)-amine,
(4-Chloro-phenyl)-{4-(2,4-dimethyl-thiazol-5-yl)-6-(4-trifluoromethyl-phenyl)-pyrimidin-2-yl}-amine,
4-{4-(2,4-Dimethyl-thiazol-5-yl)-6-(4-trifluoromethyl-phenyl)-pyrimidin-2-ylamino}-2-nitro-phenol,
(4-Fluoro-phenyl)-{4-(4-methyl-2-pyridin-3-yl-thiazol-5-yl)-pyrimidin-2-yl}-amine,
{4-(2,4-Dimethyl-thiazol-5-yl)-6-(3-trifluoromethyl-phenyl)-pyrimidin-2-yl}-(4-fluoro-phenyl)-amine,
4-{6-(2,4-Dimethyl-thiazol-5-yl)-2-(4-fluoro-phenylamino)-pyrimidin-4-yl}-2,6-dimethoxy-phenol,
4-{6-(2,4-Dimethyl-thiazol-5-yl)-2-(4-fluoro-phenylamino)-pyrimidin-4-yl)-phenol,
{4-(4-Methyl-2-pyridin-3-yl-thiazol-5-yl)-pyrimidin-2-yl}-(3-nitro-phenyl)-amine, (4-Iodo-phenyl)-{4-(4-methyl-2-methylamino-thiazol-5-yl)-pyrimidin-2-yl}-amine,
4-{2-Amino-6-(2,4-dimethyl-thiazol-5-yl)-pyrimidin-4-yl}-2,6-dimethoxy-phenol,
4-{4-(4-Methyl-2-methylamino-thiazol-5-yl)-pyrimidin-2-ylamino}-2-nitro-phenol,
2-Chloro-4-{4-(4-methyl-2-methylamino-thiazol-5-yl)-pyrimidin-2-ylamino}-benzoic acid ethyl ester,
{4-(2-Ethylamino-4-methyl-thiazol-5-yl)-pyrimidin-2-yl}-(4-fluoro-phenyl)-amine,
{4-(4-Methyl-2-methylamino-thiazol-5-yl)-pyrimidin-2-yl}-(3-nitro-phenyl)-amine,
3-{4-(2-Ethylamino-4-methyl-thiazol-5-yl)-pyrimidin-2-ylamino}-phenol,
2-Chloro-4-{4-(2-ethylamino-4-methyl-thiazol-5-yl)-pyrimidin-2-ylamino}-benzoic acid ethyl ester,
4-Chloro-3-{4-(2,4-dimethyl-thiazol-5-yl)-pyrimidin-2-ylamino}-benzoic acid 2-methoxy-ethyl ester,
2-Chloro-4-{4-(2,4-dimethyl-thiazol-5-yl)-pyrimidin-2-ylamino}-benzoic acid 2-methoxy-ethyl ester,
4-Chloro-3-{4-(2,4-dimethyl-thiazol-5-yl)-pyrimidin-2-ylamino}-benzoic acid,
2-Chloro-5-{3-(2,4-dimethyl-thiazol-5-yl)-phenylamino}-benzoic acid,
{4-(2-Allylamino-4-methyl-thiazol-5-yl)-pyrimidin-2-yl)}-(4-fluoro-phenyl)-amine,
(3-Bromo-phenyl)-{4-(4-methyl-2-methylamino-thiazol-5-yl)-pyrimidin-2-yl}-amine,
{4-(2-Allylamino-4-methyl-thiazol-5-yl)-pyrimidin-2-yl}-(3-nitro-phenyl)-amine,
3-{4-(4-Methyl-2-methylamino-thiazol-5-yl)-pyrimidin-2-ylamino}-phenol,
(4-Bromo-phenyl)-{4-(4-methyl-2-methylamino-thiazol-5-yl)-pyrimidin-2-yl}-amine,
(4-Chloro-phenyl)-{4-(4-methyl-2-methylamino-thiazol-5-yl)-pyrimidin-2-yl}-amine,
(3-Methoxy-phenyl)-{4-(4-methyl-2-methylamino-thiazol-5-yl)-pyrimidin-2-yl}-amine,
{4-(4-Methyl-2-methylamino-thiazol-5-yl)-pyrimidin-2-yl}-(4-trifluoromethyl-phenyl)-amine,
{4-(4-Methyl-2-methylamino-thiazol-5-yl)-pyrimidin-2-yl}-(3-trifluoromethyl-phenyl)-amine,
{4-(2-Allylamino-4-methyl-thiazol-5-yl)-pyrimidin-2-yl}-(3-nitro-phenyl)-amine,
2-Chloro-5-{4-(2,4-dimethyl-thiazol-5-yl)-pyrimidin-2-ylamino}-benzoic acid ethyl ester,
3-Chloro-2-{4-(2,4-dimethyl-thiazol-5-yl)-pyrimidin-2-ylamino}-benzoic acid ethyl ester,
{4-(2,4-Dimethyl-thiazol-5-yl)-pyrimidin-2-yl}-(2-fluoro-4-iodo-phenyl)-amine,
2-{4-(2,4-Dimethyl-thiazol-5-yl)-pyrimidin-2-ylamino}-5-methoxy-phenol,
(3-Chloro-4-iodo-phenyl)-{4-(2,4-dimethyl-thiazol-5-yl)-pyrimidin-2-yl}-amine,
2-Chloro-4-{4-(2,4-dimethyl-thiazol-5-yl)-pyrimidin-2-ylamino}-phenol,
5-{4-(2,4-Dimethyl-thiazol-5-yl)-pyrimidin-2-ylamino}-2-fluoro-benzoic acid 2-methoxy-ethyl ester,
2-Chloro-5-{4-(2,4-dimethyl-thiazol-5-yl)-pyrimidin-2-ylamino}-benzoic acid methyl ester,
4-Chloro-3-{4-(2,4-dimethyl-thiazol-5-yl)-pyrimidin-2-ylamino}-benzoic acid methyl ester,
2-Chloro-4-{4-(2,4-dimethyl-thiazol-5-yl)-pyrimidin-2-ylamino}-benzoic acid methyl ester,
(3-Iodo-phenyl)-{4-(4-methyl-2-methylamino-thiazol-5-yl)-pyrimidin-2-yl}-amine,
(3-Fluoro-phenyl)-{4-(4-methyl-2-methylamino-thiazol-5-yl)-pyrimidin-2-yl}-amine,
(3,4-Difluoro-phenyl)-{4-(4-methyl-2-methylamino-thiazol-5-yl)-pyrimidin-2-yl}-amine,
(2,4-Difluoro-phenyl)-{4-(4-methyl-2-methylamino-thiazol-5-yl)-pyrimidin-2-yl}-amine,
(3,5-Difluoro-phenyl)-{4-(4-methyl-2-methylamino-thiazol-5-yl)-pyrimidin-2-yl}-amine,
(4-Chloro-3-trifluoromethyl-phenyl)-{4-(4-methyl-2-methylamino-thiazol-5-yl)-pyrimidin-2-yl}-amine,
(3-Chloro-phenyl)-{4-(4-methyl-2-methylamino-thiazol-5-yl)-pyrimidin-2-yl}-amine,
(4-Methoxy-phenyl)-{4-(4-methyl-2-methylamino-thiazol-5-yl)-pyrimidin-2-yl}-amine,
(4-Fluoro-3-nitro-phenyl)-{4-(4-methyl-2-methylamino-thiazol-5-yl)-pyrimidin-2-yl}-amine,
4-{4-{2-(4-Nitro-phenylamino)-thiazol-5-yl}-pyrimidin-2-ylamino}-phenol,
N-{5-{2-(4-Hydroxy-phenylamino)-pyrimidin-4-yl}-4-methyl-thiazol-2-yl}-acetamide,
(4-Fluoro-phenyl)-{4-{2-(4-nitro-phenylamino)-thiazol-5-yl}-pyrimidin-2-yl}-amine,
4-{4-(2-Amino-4-methyl-thiazol-5-yl)-pyrimidin-2-ylamino}-phenol,
N-{3-{4-(2,4-Dimethyl-thiazol-5-yl)-pyrimidin-2-ylamino}-phenyl}-guanidine,
{3-{4-(2,4-Dimethyl-thiazol-5-yl)-pyrimidin-2-ylamino}-phenyl}-methanol,
{4-(2,4-Dimethyl-thiazol-5-yl)-pyrimidin-2-yl}-(4-pyridin-4-ylmethyl-phenyl)-amine,
{3-(2-Diethylamino-ethoxymethyl)-phenyl}-{4-(2,4-dimethyl-thiazol-5-yl)-pyrimidin-2-yl}-amine,
N,N-Dimethyl-N'-{4-(2,4-dimethyl-thiazol-5-yl)-pyrimidin-2-yl}-benzene-1,4-diamine, and
{4-{4-(2,4-Dimethyl-thiazol-5-yl)-pyrimidin-2-ylamino}-phenyl}-trimethyl-ammonium.

Also encompassed by this invention are one or more compounds selected from the following:
(4-Chloro-phenyl)-{4-(2,4-dimethyl-thiazol-5-yl)-pyrimidin-2-yl}-amine,
(3-Chloro-phenyl)-{4-(2,4-dimethyl-thiazol-5-yl)-pyrimidin-2-yl}-amine,
{4-(2,5-Dichloro-thiophen-3-yl)-pyrimidin-2-yl}-(3-nitro-phenyl)-amine,
{4-(2,4-Dimethyl-thiazol-5-yl)-pyrimidin-2-yl}-(3-nitro-phenyl)-amine,
{4-(2,4-Dimethyl-thiazol-5-yl)-pyrimidin-2-yl}-(4-nitro-phenyl)-amine,
{4-(2,4-Dimethyl-thiazol-5-yl)-pyrimidin-2-yl}-(2-fluoro-phenyl)-amine,
{4-(2,4-Dimethyl-thiazol-5-yl)-pyrimidin-2-yl}-(4-fluoro-phenyl)-amine,
(2,4-Difluoro-phenyl)-{4-(2,4-dimethyl-thiazol-5-yl)-pyrimidin-2-yl}-amine,
(3,5-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(4-trifluoromethyl-phenyl)-amine,
(3-Bromo-phenyl)-{4-(2,4-dimethyl-thiazol-5-yl)-pyrimidin-2-yl}-amine,
(4-Bromo-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-iodo-phenyl)-amine,
{4-(2,4-Dimethyl-thiazol-5-yl)-pyrimidin-2-yl}-(4-fluoro-phenyl)-amine,
(3,4-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-methoxy-phenyl)-amine, {4-(2,4-Dimethyl-thiazol-5-yl)-pyrimidin-2-yl}-(3-methoxy-phenyl)-amine,
{4-(2,4-Dimethyl-thiazol-5-yl)-pyrimidin-2-yl}-(4-methoxy-phenyl)-amine,
3-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-2-nitro-phenol,
N-{4-(2,4-Dimethyl-thiazol-5-yl)-pyrimidin-2-yl}-benzene-1,3-diamine,
4-{4-(2,4-Dimethyl-thiazol-5-yl)-pyrimidin-2-ylamino}-benzonitrile,
3-{4-(2,4-Dimethyl-thiazol-5-yl)-pyrimidin-2-ylamino}-benzonitrile,
4-{4-(2,4-Dimethyl-thiazol-5-yl)-pyrimidin-2-ylamino}-benzoic acid methyl ester,
(3-Chloro-4-methyl-phenyl)-{4-(2,4-dimethyl-thiazol-5-yl)-pyrimidin-2-yl}-amine,
(3-Chloro-4-methoxy-phenyl)-{4-(2,4-dimethyl-thiazol-5-yl)-pyrimidin-2-yl}-amine,
4-{-4-(2,4-Dimethyl-thiazol-5-yl)-pyrimidin-2-ylamino}-benzoic acid,
{4-Bromo-6-(2,4-dimethyl-thiazol-5-yl)-pyrimidin-2-yl}-(3-nitro-phenyl)-amine,
4-{4-(4-Methyl-2-phenyl-thiazol-5-yl)-pyrimidin-2-ylamino}-phenol,
(4-Fluoro-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-phenol,
(4-Iodo-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-2-nitro-phenol,
2-Chloro-4-{4-(4-methyl-2-methylamino-thiazol-5-yl)-pyrimidin-2-ylamino}-benzoic acid ethyl ester,
{4-(2-Ethylamino-4-methyl-thiazol-5-yl)-pyrimidin-2-yl}-(4-fluoro-phenyl)-amine,
{4-(4-Methyl-2-methylamino-thiazol-5-yl)-pyrimidin-2-yl}-(3-nitro-phenyl)-amine,
{4-(2-Allylamino-4-methyl-thiazol-5-yl)-pyrimidin-2-yl}-(4-fluoro-phenyl)-amine,
(3-Bromo-phenyl)-{4-(4-methyl-2-methylamino-thiazol-5-yl)-pyrimidin-2-yl}-amine,
{4-(2-Allylamino-4-methyl-thiazol-5-yl)-pyrimidin-2-yl}-(3-nitro-phenyl)-amine,
3-{4-(4-Methyl-2-methylamino-thiazol-5-yl)-pyrimidin-2-ylamino}-phenol,
(4-Bromo-phenyl)-{4-(4-methyl-2-methylamino-thiazol-5-yl)-pyrimidin-2-yl}-amine,
(4-Chloro-phenyl)-{4-(4-methyl-2-methylamino-thiazol-5-yl)-pyrimidin-2-yl}-amine,
(3-Methoxy-phenyl)-{4-(4-methyl-2-methylamino-thiazol-5-yl)-pyrimidin-2-yl}-amine,
{4-(4-Methyl-2-methylamino-thiazol-5-yl)-pyrimidin-2-yl}-(4-trifluoromethyl-phenyl)-amine,
{4-(4-Methyl-2-methylamino-thiazol-5-yl)-pyrimidin-2-yl}-(3-trifluoromethyl-phenyl)-amine,
5-{4-(2,4-Dimethyl-thiazol-5-yl)-pyrimidin-2-ylamino}-2-fluoro-benzoic acid 2-methoxy-ethyl ester,
2-Chloro-5-{4-(2,4-dimethyl-thiazol-5-yl)-pyrimidin-2-ylamino}-benzoic acid methyl ester,
(3,5-Difluoro-phenyl)-{4-(4-methyl-2-methylamino-thiazol-5-yl)-pyrimidin-2-yl}-amine,
(4-Chloro-3-trifluoromethyl-phenyl)-{4-(4-methyl-2-methylamino-thiazol-5-yl)-pyrimidin-2-yl}-amine,
(3-Chloro-phenyl)-{4-(4-methyl-2-methylamino-thiazol-5-yl)-pyrimidin-2-yl}-amine,
(4-Methoxy-phenyl)-{4-(4-methyl-2-methylamino-thiazol-5-yl)-pyrimidin-2-yl}-amine,
2-{4-(2,4-Dimethyl-thiazol-5-yl)-pyrimidin-2-ylamino}-5-methoxy-phenol,
(3-Fluoro-phenyl)-{4-(4-methyl-2-methylamino-thiazol-5-yl)-pyrimidin-2-yl}-amine,
(3,4-Difluoro-phenyl)-{4-(4-methyl-2-methylamino-thiazol-5-yl)-pyrimidin-2-yl}-amine,
N-{3-{4-(2,4-Dimethyl-thiazol-5-yl)-pyrimidin-2-ylamino}-phenyl}-guanidine,
{4-(2,4-Dimethyl-thiazol-5-yl)-pyrimidin-2-yl}-(4-pyridin-4-ylmethyl-phenyl)-amine,
N,N-Dimethyl-N'-{4-(2,4-dimethyl-thiazol-5-yl)-pyrimidin-2-yl}-benzene-1,4-diamine,
{4-{4-(2,4-Dimethyl-thiazol-5-yl)-pyrimidin-2-ylamino}-phenyl}-trimethyl-ammonium.

In addition, this invention provides a compound selected from the following:
{4-(2,4-Dimethyl-thiazol-5-yl)-pyrimidin-2-yl}-(4-trifluoromethyl-phenyl)-amine,
(4-Bromo-phenyl)-{4-(2,4-dimethyl-thiazol-5-yl)-pyrimidin-2-yl}-amine,
4-{4-(4-Methyl-2-methylamino-thiazol-5-yl)-pyrimidin-2-ylamino}-phenol,
(4-Fluoro-phenyl)-{4-(4-methyl-2-methylamino-thiazol-5-yl)-pyrimidin-2-yl}-amine.

Further, this invention provides one or more compounds selected from the following:
(2-Chloro-phenyl)-{4-(2,5-dichloro-thiophen-3-yl)-pyrimidin-2-yl}-amine,
(4-Chloro-phenyl)-{4-(2,5-dichloro-thiophen-3-yl)-pyrimidin-2-yl}-amine,
(3-Chloro-phenyl)-{4-(2,5-dichloro-thiophen-3-yl)-pyrimidin-2-yl}-amine,
(2-Chloro-phenyl)-{4-(2,5-dimethyl-thiophen-3-yl)-pyrimidin-2-yl}-amine,
(3,5-Dichloro-phenyl)-{4-(2,4-dimethyl-thiazol-5-yl)-pyrimidin-2-yl}-amine,
(2,4-Dichloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-trifluoromethyl-phenyl)-amine,
{4-(2,4-Dimethyl-thiazol-5-yl)-pyrimidin-2-yl}-(2-trifluoromethyl-phenyl)-amine,
{4-(2,4-Dimethyl-thiazol-5-yl)-pyrimidin-2-yl}-(2-iodo-phenyl)-amine,
{4-(2,4-Dimethyl-thiazol-5-yl)-pyrimidin-2-yl}-(4-iodo-phenyl)-amine,
N-{4-(2,4-Dimethyl-thiazol-5-yl)-pyrimidin-2-yl}-3-nitro-benzenesulfonamide,
{4-(2,4-Dimethyl-thiazol-5-yl)-6-phenyl-pyrimidin-2-yl}-(3-nitro-phenyl)-amine,
(3,4-Difluoro-phenyl)-{4-(4-methyl-2-phenyl-thiazol-5-yl)-pyrimidin-2-yl}-amine,
(4-Chloro-phenyl)-{4-(2,4-dimethyl-thiazol-5-yl)-6-(4-trifluoromethyl-phenyl)-pyrimidin-2-yl}-amine,
4-{6-(2,4-Dimethyl-thiazol-5-yl)-2-(4-fluoro-phenylamino)-pyrimidin-4-yl}-2,6-dimethoxy-phenol,
4-{6-(2,4-Dimethyl-thiazol-5-yl)-2-(4-fluoro-phenylamino)-pyrimidin-4-yl}-phenol,
2-Chloro-5-{4-(2,4-dimethyl-thiazol-5-yl)-pyrimidin-2-ylamino}-benzoic acid ethyl ester,
3-Chloro-2-{4-(2,4-dimethyl-thiazol-5-yl)-pyrimidin-2-ylamino}-benzoic acid ethyl ester,
{4-(2,4-Dimethyl-thiazol-5-yl)-pyrimidin-2-yl}-(2-fluoro-4-iodo-phenyl)-amine, (3-Chloro-4-iodo-phenyl)-{4-(2,4-dimethyl-thiazol-5-yl)-pyrimidin-2-yl}-amine,
4-Chloro-3-{4-(2,4-dimethyl-thiazol-5-yl)-pyrimidin-2-ylamino}-benzoic acid methyl ester,
(3-Iodo-phenyl)-{4-(4-methyl-2-methylamino-thiazol-5-yl)-pyrimidin-2-yl}-amine,
(2,4-Difluoro-phenyl)-{4-(4-methyl-2-methylamino-thiazol-5-yl)-pyrimidin-2-yl}-amine.

This invention includes the compound {4-(2,4-Dimethyl-thiazol-5-yl)-pyrimidin-2-yl}-(4-iodo-phenyl)-amine.

In one aspect, this invention pertains to pharmaceutical compositions comprising a compound as described above or a pharmaceutically acceptable salt thereof together with a pharmaceutically acceptable excipient.

This invention also pertains to the above pharmaceutical compositions which further comprise one or more other anticancer agents.

This invention includes the use of one or more of the above-described compounds or pharmaceutically acceptable salts thereof in the treatment of a proliferative disorder.

In an embodiment of the above use, the proliferative disorder is cancer or leukaemia.

In another embodiment of the above uses, said one or more compounds are administered in an amount sufficient to inhibit at least one CDK enzyme.

In still another embodiment of the above uses, the CDK enzyme is CDK2 and/or CDK4.

In another aspect, this invention provides the use of one or more compounds of formula

I wherein:
$X^1$ is CH and $X^2$ is S; or
one of $X^1$ and $X^2$ is S, and the other of $X^1$ and $X^2$ is N;
Z is NH, NHCO, NHSO$_2$, NHCH$_2$, CH$_2$, CH$_2$CH$_2$, or CH=CH;
$R^1$, $R^2$, and $R^3$ are independently H, alkyl, aryl, aralkyl, heterocycle, halogeno, NO$_2$, CN, OH, alkoxy, aryloxy, NH$_2$, NH—R', N—(R')(R''), NH-aryl, N-(aryl)$_2$, COOH, COO—R', COO-aryl, CONH$_2$, CONH—R', CON—(R')(R''), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogeno, NO$_2$, CN, OH, O-methyl, NH$_2$, COOH, CONH$_2$ and CF$_3$;
$R^4$, $R^5$, $R^6$, $R^7$, and $R^8$ are independently from each other H, substituted or unsubstituted lower alkyl, halogeno, NO$_2$, CN, OH, substituted or unsubstituted alkoxy, NH$_2$, NH—R', N—(R')(R''), COOH, COO—R', CONH$_2$, CONH—R', CON—(R')(R''), SO$_3$H, SO$_2$NH$_2$, or CF$_3$, other than when $R^5$, $R^6$ and $R^7$ are all methoxy and $R^4$ and $R^8$ are hydrogen or when $R^6$ and $R^7$ are both methoxy and $R^4$, $R^5$ and $R^8$ are all hydrogen;

wherein R' and R'' are each independently alkyl groups that may be the same or different;
and pharmaceutically acceptable salts thereof;
in the manufacture of a medicament for use in the treatment of a proliferative disease.

In an embodiment of the above uses, the compound is any of the above-described compounds.

In another embodiment of the above uses, the compound is administered in combination with one or more other anticancer compounds.

Preferred compounds of formula I are those bearing a mono- or di-substituted 5-membered heterocyclic radical, attached to the pyrimidine ring through one of the ring carbon atoms and chosen from the following: thiazol-3-yl thiazol-5-yl and thien-3-yl, preferably a thien-3-yl or thiazol-5-yl, most preferably, the heterocycle is a thiazol-5-yl group.

Preferably, $R^1$, $R^2$ and $R^3$ are each independently selected from H, alkyl, aryl, aralkyl, halogeno, NO$_2$, CN, OH, alkoxy, aryloxy, NH$_2$, NHCOR', NHCOR', NH-aryl, NH—R', N—(R')(R''), COOH, COO—R', CONH$_2$, CONH—R', CON—(R')(R''), SO$_3$H, SO$_2$NH$_2$, CF$_3$, and CO—R' wherein alkyl, aryl, NH-aryl and aralkyl groups may be further substituted with one or more groups selected from halogeno, NO$_2$, CN, OH, O-methyl, NH$_2$, COOH, CONH$_2$ and CF$_3$;

More preferably, $R^1$ and $R^2$ are each independently halogeno, C$_{1-4}$ alkyl group, H, aryl, heterocycle or NH(R'). Even more preferably, $R^1$ and $R^2$ are both chloro or both methyl.

$R^3$ is preferably selected from H, aryl, substituted aryl, halo, C$_{1-4}$ alkoxy and OH, more preferably, $R^3$ is H or methyl, most preferably H.

The group Z is preferably NH, NHSO$_2$ or NHCH$_2$, more preferably NH or NHSO$_2$ most preferably NH.

The phenyl substituents $R^4$–$R^8$ are preferably selected from H, OH, halogeno, nitro, amino, alkoxy, carbamoyl, sulfamyl, C$_{1-4}$ alkyl, substituted C$_{1-4}$ alkyl, COOH, COOR', CN, CF$_3$, (CH$_2$)$_n$O(CH$_2$)$_m$NR'R'', alkyl-aryl, alkyl-heteroaryl, NH(C=NH)NH$_2$, N(R')$_3^-$, N(R')(R'') and (CH$_2$)$_n$CO$_2$(CH$_2$)$_m$OR'''.

Even more preferably, $R^4$-$R^8$ are each independently F, NH$_2$, NO$_2$, OH, Cl, Br, I, CF$_3$, OMe, COOH, COOR', CN, H, C$_{1-4}$ alkyl, C$_{1-4}$ alkoxy, CH$_2$CO$_2$CH$_2$CH$_2$OMe, NH(C=NH)NH$_2$, and CO$_2$CH$_2$CH$_2$OMe, CH$_2$OCH$_2$CH$_2$NEt$_2$, CH$_2$-heteroaryl, NMe$_3^+$, NMe$_2$.

R', R'', and R''' are each independently preferably methyl or ethyl.

Particularly preferred combinations of the above stated preferences include where the heterocycle is a thien-3-yl group or a thiazol-5-yl group, the latter being most preferred, Z being NH, $R^3$ being H and the remaining groups being selected from the preferences stated above. Particularly preferable is when $R^1$ and $R^2$ are each independently one or more of halogeno or C$_{1-4}$ alkyl groups, especially when $R^1$ and $R^2$ are both chloro or methyl and when $R^4$ to $R^8$ are selected independently from of F, NH$_2$, NO$_2$, OH, Cl, Br, I, CF$_3$ and OMe.

In a particularly preferred embodiment of the invention, $X^1$ and $X^2$ are S and N respectively.

In another particularly preferred embodiment, Z is NH and $R^3$ is H.

Thus, particularly preferred embodiments include;
(a) 2-{N-(phenyl)}-4-(2,4-dimethylthiazol-5-yl) pyrimidineamines in which the phenyl group is 2-, 3- or 4-substituted by at least one of Me, F, NH$_2$, NO$_2$, OH, Cl, Br, I, CF$_3$, OMe, CN, COOH, CH$_2$OH, COOMe, COOEt, NH(C=NH)NH$_2$, CH$_2$CO$_2$CH$_2$CH$_2$OMe, CH$_2$-pyridyl, CH$_2$OCH$_2$CH$_2$NEt$_2$, CO$_2$CH$_2$CH$_2$OMe, NMe$_3^+$ and NMe$_2$;

(b) 2-{N-(phenyl)}-4-(2,5-dichloro-thien-3-yl) pyrimidineamines in which the phenyl group is 2-, 3- or 4-substituted by at least one of F, NO$_2$, OH, Cl, or OMe;

(c) 2-{N-(phenyl)}-4-(2,5-dimethyl-thien-3-yl) pyrimidineamines in which the phenyl group is 2-, 3- or 4-substituted by at least one of F, NO$_2$, OH, Cl, or OMe, and (d) 2-{N-(phenyl)}-4-(4-methyl-2-methylamino-thiazol-5-yl)pyrimidineamines in which the phenyl group is 2-, 3- or 4-substituted by at least one of F, OH, I, NO$_2$, Cl, COOR', Br, OMe or CF$_3$.

Within these groups (a) to (d), the following phenyl substituents are preferable;

for group (a) the phenyl group is mono-substituted by F, NH$_2$, NO$_2$, OH, Cl, Br, I, CF$_3$, OMe, CN, CH$_2$OH, COOH, COOMe, COOEt, CH$_2$CO$_2$CH$_2$CH$_2$OMe or CO$_2$CH$_2$CH$_2$OMe at any of the 2, 3 or 4-positions, or di-substituted by 2,4-difluoro, 3,5-difluoro, 3,4-difluoro, 2,4-dichloro, 3,5-dichloro, 3,4-dichloro, 4-hydroxy-2-nitro, 4-hydroxy-3-nitro, 6-chloro-3-carboxy, 4-chloro-3-carboxy, 6-chloro-2-carboxy, 2-fluoro-4-iodo, 2-hydroxy-4-methoxy, 3-chloro-4-iodo, 3-chloro-4-hydroxy, 3-chloro-4-methyl, 3-chloro-4-methoxy, 4-fluoro-3-nitro, 6-chloro-3-methoxycarbonyl, 3-chloro-4-methoxcarbonyl, 3-chloro-4-ethoxcarbonyl, 2-hydroxy-4-methoxy, 2-chloro-5-methoxycarbonyl, 4-chloro-3-methoxycarbonyl, 6-chloro-3-(CO$_2$CH$_2$CH$_2$OMe), 3-chloro-4-(CO$_2$CH$_2$CH$_2$OMe), 4-chloro-3-trifluoromethyl, or 3-(CO$_2$CH$_2$CH$_2$OMe)-4-fluoro.

for group (b) the phenyl group is mono-substituted by chloro, or, nitro, at any of the 2, 3 or 4-positions;

for group (c) the phenyl group is mono-substituted by chloro at any of the 2, 3 or 4-positions, for group (d) the phenyl group is mono-substituted by chloro, bromo, iodo, fluoro, OH, nitro, CF$_3$ or OMe at any of the 2, 3 or 4 positions, or disubstituted by 4-hydroxy-3-nitro, 3-chloro-4-ethoxycarbonyl, 3,4-difluoro, 2,4-difluoro, 4-chloro-3-trifluoromethyl or 4-fluoro-3-nitro.

Even more preferably, for group (a) the phenyl group is monosubstituted by Br, I or CF$_3$.

Most preferably, the compounds of the present invention are selected from;

4-(2,5-Dichloro-thiophen-3-yl)-2-phenyl-pyrimidine,
(2-Chloro-phenyl)-{4-(2,5-dichloro-thiophen-3-yl)-pyrimidin-2-yl}-amine,
(4-Chloro-phenyl)-4-(2,5-dichloro-thiophen-3-yl)-pyrimidin-2-yl}-amine,
(3-Chloro-phenyl)-{4-(2,5-dichloro-thiophen-3-yl)-pyrimidin-2-yl}-amine,
(2-Chloro-phenyl)-{4-(2,4-dimethyl-thiazol-5-yl)-pyrimidin-2-yl}-amine,
(4-Chloro-phenyl)-{4-(2,4-dimethylthiazol-5-yl)-pyrimidin-2-yl}-amine,
(3-Chloro-phenyl)-{4-(2,4-dimethyl-thiazol-5-yl)-pyrimidin-2-yl}-amine,
{4-(2,5-Dichloro-thiophen-3-yl)-pyrimidin-2-yl}-(2-nitro-phenyl)-amine,
{4-(2,5-Dichloro-thiophen-3-yl)-pyrimidin-2-yl}-(3-nitro-phenyl)-amine,
{4-(2,5-Dichloro-thiophen-3-yl)-pyrimidin-2-yl}-(4-nitro-phenyl)-amine,
{4-(2,4-Dimethyl-thiazol-5-yl)-pyrimidin-2-yl}-(2-nitro-phenyl)-amine,
{4-(2,4-Dimethyl-thiazol-5-yl)-pyrimidin-2-yl}-(3-nitro-phenyl)-amine,
{4-(2,4-Dimethyl-thiazol-5-yl)-pyrimidin-2-yl}-(4-nitro-phenyl)-amine,
{4-(2,4-Dimethyl-thiazol-5-yl)-pyrimidin-2-yl}-(4-nitro-phenyl)-amine,
(4-Chloro-phenyl)-{4-(2,5-dimethyl-thiophen-3-yl)-pyrimidin-2-yl}-amine,
(2-Chloro-phenyl)-{4-(2,5-dimethyl-thiophen-3-yl)-pyrimidin-2-yl}-amine,
(3-Chloro-phenyl)-{4-(2,5-dimethyl-thiophen-3-yl)-pyrimidin-2-yl}-amine,
{4-(2,4-Dimethyl-thiazol-5-yl)-pyrimidin-2-yl}-(2-fluoro-phenyl)-amine,
{4-(2,4-Dimethyl-thiazol-5-yl)-pyrimidin-2-yl}-(4-fluoro-phenyl)-amine,
(2,4-Difluoro-phenyl)-{4-(2,4-dimethyl-thiazol-5-yl)-pyrimidin-2-yl}-amine,
(3,5-Difluoro-phenyl)-{4-(2,4-dimethyl-thiazol-5-yl)-pyrimidin-2-yl}-amine,
(3,5-Dichloro-phenyl)-{4-(2,4-dimethyl-thiazol-5-yl)-pyrimidin-2-yl}-amine,
(2,4-Dichloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-trifluoromethyl-phenyl)-amine,
{4-(2,4-Dimethyl-thiazol-5-yl)-pyrimidin-2-yl}-(2-trifluoromethyl-phenyl)-amine,
{4-(2,4-Dimethyl-thiazol-5-yl)-pyrimidin-2-yl}-(4-trifluoromethyl-phenyl)-amine,
(2-Bromo-phenyl)-{4-(2,4-dimethyl-thiazol-5-yl)-pyrimidin-2-yl}-amine,
(3-Bromo-phenyl)-{4-(2,4-dimethyl-thiazol-5-yl)-pyrimidin-2-yl}-amine,
(4-Bromo-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-iodo-phenyl)-amine,
{4-(2,4-Dimethyl-thiazol-5-yl)-pyrimidin-2-yl}-(3-iodo-phenyl)-amine,
{4-(2,4-Dimethyl-thiazol-5-yl)-pyrimidin-2-yl}-(4-iodo-phenyl)-amine,
{4-(2,4-Dimethyl-thiazol-5-yl)-pyrimidin-2-yl}-pyridin-2-yl-amine,
{4-(2,4-Dimethyl-thiazol-5-yl)-pyrimidin-2-yl}-(3-fluoro-phenyl)-amine,
(3,4-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-methoxy-phenyl)-amine,
{4-(2,4-Dimethyl-thiazol-5-yl)-pyrimidin-2-yl}-(3-methoxy-phenyl)-amine,
{4-(2,4-Dimethylthiazol-5-yl)-pyrimidin-2-yl}-(4-methoxy-phenyl)-amine,
3-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-phenol,
N-{4-(2,4-Dimethyl-thiazol-5-yl)-pyrimidin-2-yl}-3-nitro-benzenesulfonamide,
4-Chloro-N-{4-(2,4-dimethyl-thiazol-5-yl)-pyrimidin-2-yl}-benzenesulfonamide,
N-{4-(2,4-Dimethyl-thiazol-5-yl)-pyrimidin-2-yl}-4-fluoro-benzenesulfonamide,
4-{4-(2,4-Dimethyl-thiazol-5-yl)-pyrimidin-2-ylamino}-2-nitro-phenol, N-{4-(2,4-Dimethyl-thiazol-5-yl)-pyrimidin-2-yl}-4-nitro-benzenesulfonamide,
N-{4-(2,4-Dimethyl-thiazol-5-yl)-pyrimidin-2-yl}-benzene-1,3-diamine,
4-{4-(2,4-Dimethyl-thiazol-5-yl)-pyrimidin-2-ylamino}-benzonitrile,
3-{4-(2,4-Dimethyl-thiazol-5-yl)-pyrimidin-2-ylamino}-benzonitrile,
4-{4-(2,4-Dimethyl-thiazol-5-yl)-pyrimidin-2-ylamino}-benzoic acid methyl ester,
(3-Chloro-4-methyl-phenyl)-{4-(2,4-dimethyl-thiazol-5-yl)-pyrimidin-2-yl}-amine,
(3-Chloro-4-methoxy-phenyl)-{4-(2,4-dimethyl-thiazol-5-yl)-pyrimidin-2-yl}-amine,
4-{4-(2,4-Dimethyl-thiazol-5-yl)-pyrimidin-2-ylamino}-benzoic acid,
{4-Bromo-6-(2,4-dimethyl-thiazol-5-yl)-pyrimidin-2-yl}-(3-nitro-phenyl)-amine,
{4-(2,4-Dimethyl-thiazol-5-yl)-6-phenyl-pyrimidin-2-yl}-(3-nitro-phenyl)-amine,
4-{4-(2,4-Dimethyl-thiazol-5-yl)-6-phenyl-pyrimidin-2-ylamino}-phenol,
(3,4-Difluoro-phenyl)-{4-(4-methyl-2-phenyl-thiazol-5-yl)-pyrimidin-2-yl}-amine,
4-{4-(4-Methyl-2-phenyl-thiazol-5-yl)-pyrimidin-2-ylamino}-phenol,
{4-(2,4-Dimethyl-thiazol-5-yl)-6-phenyl-pyrimidin-2-yl}-(4-fluoro-phenyl)-amine,
(4-Fluoro-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-phenol,
{4-(2,4-Dimethyl-thiazol-5-yl)-6-(4-trifluoromethyl-phenyl)-pyrimidin-2-yl}-(4-fluoro-phenyl)-amine,
(4-Chloro-phenyl)-{4-(2,4-dimethyl-thiazol-5-yl)-6-(4-trifluoromethyl-phenyl)-pyrimidin-2-yl}-amine,
4-{4-(2,4-Dimethyl-thiazol-5-yl)-6-(4-trifluoromethyl-phenyl)-pyrimidin-2-ylamino}-2-nitro-phenol,
(4-Fluoro-phenyl)-{4-(4-methyl-2-pyridin-3-yl-thiazol-5-yl)-pyrimidin-2-yl}-amine,
{4-(2,4-Dimethyl-thiazol-5-yl)-6-(3-trifluoromethyl-phenyl)-pyrimidin-2-yl}-(4-fluoro-phenyl)-amine,
4-{6-(2,4-Dimethyl-thiazol-5-yl)-2-(4-fluoro-phenylamino)-pyrimidin-4-yl}-2,6-dimethoxy-phenol,
4-{6-(2,4-Dimethyl-thiazol-5-yl)-2-(4-fluoro-phenylamino)-pyrimidin-4-yl}-phenol,
{4-(4-Methyl-2-pyridin-3-yl-thiazol-5-yl)-pyrimidin-2-yl}-(3-nitro-phenyl)-amine,
(4-Iodo-phenyl)-{4-(4-methyl-2-methylamino-thiazol-5-yl)-pyrimidin-2-yl}-amine,
4-{2-Amino-6-(2,4-dimethyl-thiazol-5-yl)-pyrimidin-4-yl}-2,6-dimethoxy-phenol,
4-{4-(4-Methyl-2-methylamino-thiazol-5-yl)-pyrimidin-2-ylamino}-2-nitro-phenol,
2-Chloro-4-{4-(4-methyl-2-methylamino-thiazol-5-yl)-pyrimidin-2-ylamino}-benzoic acid ethyl ester,
{4-(2-Ethylamino-4-methyl-thiazol-5-yl)-pyrimidin-2-yl}-(4-fluoro-phenyl)-amine,
{4-(4-Methyl-2-methylamino-thiazol-5-yl)-pyrimidin-2-yl}-(3-nitro-phenyl)-amine,
3-{4-(2-Ethylamino-4-methyl-thiazol-5-yl)-pyrimidin-2-ylamino}-phenol,
2-Chloro-4-{4-(2-ethylamino-4-methyl-thiazol-5-yl)-pyrimidin-2-ylamino}-benzoic acid ethyl ester,
4-Chloro-3-{4-(2,4-dimethyl-thiazol-5-yl)-pyrimidin-2-ylamino}-benzoic acid 2-methoxy-ethyl ester,
2-Chloro-4-{4-(2,4-dimethyl-thiazol-5-yl)-pyrimidin-2-ylamino}-benzoic acid 2-methoxy-ethyl ester,
4-Chloro-3-{4-(2,4-dimethyl-thiazol-5-yl)-pyrimidin-2-ylamino}-benzoic acid,
2-Chloro-5-{3-(2,4-dimethyl-thiazol-5-yl)-phenylamino}-benzoic acid,
{4-(2-Allylamino-4-methyl-thiazol-5-yl)-pyrimidin-2-yl}-(4-fluoro-phenyl)-amine,
(3-Bromo-phenyl)-{4-(4-methyl-2-methylamino-thiazol-5-yl)-pyrimidin-2-yl}-amine,
{4-(2-Allylamino-4-methyl-thiazol-5-yl)-pyrimidin-2-yl}-(3-nitro-phenyl)-amine,
3-{4-(4-Methyl-2-methylamino-thiazol-5-yl)-pyrimidin-2-ylamino}-phenol,
(4-Bromo-phenyl)-{4-(4-methyl-2-methylamino-thiazol-5-yl)-pyrimidin-2-yl}-amine,
(4-Chloro-phenyl)-{4-(4-methyl-2-methylamino-thiazol-5-yl)-pyrimidin-2-yl}-amine,
(3-Methoxy-phenyl)-{4-(4-methyl-2-methylamino-thiazol-5-yl)-pyrimidin-2-yl}-amine,
{4-(4-Methyl-2-methylamino-thiazol-5-yl)-pyrimidin-2-yl}-(4-trifluoromethyl-phenyl)-amine,
{4-(4-Methyl-2-methylamino-thiazol-5-yl)-pyrimidin-2-yl}-(3-trifluoromethyl-phenyl)-amine,
{4-(2-Allylamino-4-methyl-thiazol-5-yl)-pyrimidin-2-yl}-(3-nitro-phenyl)-amine,
2-Chloro-5-{4-(2,4-dimethyl-thiazol-5-yl)-pyrimidin-2-ylamino}-benzoic acid ethyl ester,
3-Chloro-2-{4-(2,4-dimethyl-thiazol-5-yl)-pyrimidin-2-ylamino}-benzoic acid ethyl ester,
{4-(2,4-Dimethyl-thiazol-5-yl)-pyrimidin-2-yl}-(2-fluoro-4-iodo-phenyl)-amine,
2-{4-(2,4-Dimethyl-thiazol-5-yl)-pyrimidin-2-ylamino}-5-methoxy-phenol,
(3-Chloro-4-iodo-phenyl)-{4-(2,4-dimethyl-thiazol-5-yl)-pyrimidin-2-yl}-amine,
2-Chloro-4-{4-(2,4-dimethyl-thiazol-5-yl)-pyrimidin-2-ylamino}-phenol,
5-{4-(2,4-Dimethyl-thiazol-5-yl)-pyrimidin-2-ylamino}-2-fluoro-benzoic acid 2-methoxy-ethyl ester,
2-Chloro-5-{4-(2,4-dimethyl-thiazol-5-yl)-pyrimidin-2-ylamino}-benzoic acid methyl ester,
4-Chloro-3-{4-(2,4-dimethyl-thiazol-5-yl)-pyrimidin-2-ylamino}-benzoic acid methyl ester,
2-Chloro-4-{4-(2,4-dimethyl-thiazol-5-yl)-pyrimidin-2-ylamino}-benzoic acid methyl ester,
(3-Iodo-phenyl)-{4-(4-methyl-2-methylamino-thiazol-5-yl)-pyrimidin-2-yl}-amine,
(3-Fluoro-phenyl)-{4-(4-methyl-2-methylamino-thiazol-5-yl)-pyrimidin-2-yl}-amine,
(3,4-Difluoro-phenyl)-{4-(4-methyl-2-methylamino-thiazol-5-yl)-pyrimidin-2-yl}-amine,
(2,4-Difluoro-phenyl)-{4-(4-methyl-2-methylamino-thiazol-5-yl)-pyrimidin-2-yl}-amine,
(3,5-Difluoro-phenyl)-{4-(4-methyl-2-methylamino-thiazol-5-yl)-pyrimidin-2-yl}-amine,
(4-Chloro-3-trifluoromethyl-phenyl)-{4-(4-methyl-2-methylamino-thiazol-5-yl)-pyrimidin-2-yl}-amine,
(3-Chloro-phenyl)-{4-(4-methyl-2-methylamino-thiazol-5-yl)-pyrimidin-2-yl}-amine,
(4-Methoxy-phenyl)-{4-(4-methyl-2-methylamino-thiazol-5-yl)-pyrimidin-2-yl}-amine,
(4-Fluoro-3-nitro-phenyl)-{4-(4-methyl-2-methylamino-thiazol-5-yl)-pyrimidin-2-yl}-amine,
4-{4-{2-(4-Nitro-phenylamino)-thiazol-5-yl}-pyrimidin-2-ylamino}-phenol,
N-{5-{2-(4-Hydroxy-phenylamino)-pyrimidin-4-yl}-4-methyl-thiazol-2-yl}-acetamide,
(4-Fluoro-phenyl)-{4-{2-(4-nitro-phenylamino)-thiazol-5-yl}-pyrimidin-2-yl}-amine, 4-{4-(2-Amino-4-methyl-thiazol-5-yl)-pyrimidin-2-ylamino}-phenol,
N-{3-{4-(2,4-Dimethyl-thiazol-5-yl)-pyrimidin-2-ylamino}-phenyl}-guanidine,
{3-{4-(2,4-Dimethyl-thiazol-5-yl)-pyrimidin-2-ylamino}-phenyl}-methanol,
{4-(2,4-Dimethyl-thiazol-5-yl)-pyrimidin-2-yl}-(4-pyridin-4-ylmethyl-phenyl)-amine,
{3-(2-Diethylamino-ethoxymethyl)-phenyl}-{4-(2,4-dimethyl-thiazol-5-yl)-pyrimidin-2-yl}-amine,
N,N-Dimethyl-N'-{4-(2,4-dimethyl-thiazol-5-yl)-pyrimidin-2-yl}-benzene-1,4-diamine,
{4-{4-(2,4-Dimethyl-thiazol-5-yl)-pyrimidin-2-ylamino}-phenyl}-trimethyl-ammonium.

The structures of the above-mentioned compounds are illustrated in FIG. 1.

Particularly preferred compounds observed to be CDK inhibitors include the following:

(4-Chloro-phenyl)-{4-(2,4-dimethyl-thiazol-5-yl)-pyrimidin-2-yl}-amine,
(3-Chloro-phenyl)-{4-(2,4-dimethyl-thiazol-5-yl)-pyrimidin-2-yl}-amine,
{4-(2,5-Dichloro-thiophen-3-yl)-pyrimidin-2-yl}-(3-nitro-phenyl)-amine,
{4-(2,4-Dimethyl-thiazol-5-yl)-pyrimidin-2-yl}-(3-nitro-phenyl)-amine,
{4-(2,4-Dimethyl-thiazol-5-yl)-pyrimidin-2-yl}-(4-nitro-phenyl)-amine,
{4-(2,4-Dimethyl-thiazol-5-yl)-pyrimidin-2-yl}-(2-fluoro-phenyl)-amine,
{4-(2,4-Dimethyl-thiazol-5-yl)-pyrimidin-2-yl}-(4-fluoro-phenyl)-amine,
(2,4-Difluoro-phenyl)-{4-(2,4-dimethyl-thiazol-5-yl)-pyrimidin-2-yl}-amine,
(3,5-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(4-trifluoromethyl-phenyl)-amine,
(3-Bromo-phenyl)-{4-(2,4-dimethyl-thiazol-5-yl)-pyrimidin-2-yl}-amine,
(4-Bromo-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-iodo-phenyl)-amine,
{4-(2,4-Dimethyl-thiazol-5-yl)-pyrimidin-2-yl}-(3-fluoro-phenyl)-amine,
(3,4-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-methoxy-phenyl)-amine,
{4-(2,4-Dimethyl-thiazol-5-yl)-pyrimidin-2-yl}-(3-methoxy-phenyl)-amine,
{4-(2,4-Dimethyl-thiazol-5-yl)-pyrimidin-2-yl}-(4-methoxy-phenyl)-amine,
3-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-2-nitro-phenol,
N-{4-(2,4-Dimethyl-thiazol-5-yl)-pyrimidin-2-yl}-benzene-1,3-diamine,
4-{4-(2,4-Dimethyl-thiazol-5-yl)-pyrimidin-2-ylamino}-benzonitrile,
3-{4-(2,4-Dimethyl-thiazol-5-yl)-pyrimidin-2-ylamino}-benzonitrile,
4-{4-(2,4-Dimethyl-thiazol-5-yl)-pyrimidin-2-ylamino}-benzoic acid methyl ester,
(3-Chloro-4-methyl-phenyl)-{4-(2,4-dimethyl-thiazol-5-yl)-pyrimidin-2-yl}-amine,
(3-Chloro-4-methoxy-phenyl)-{4-(2,4-dimethyl-thiazol-5-yl)-pyrimidin-2-yl}-amine,
4-{4-(2,4-Dimethyl-thiazol-5-yl)-pyrimidin-2-ylamino}-benzoic acid,
{4-Bromo-6-(2,4-dimethyl-thiazol-5-yl)-pyrimidin-2-yl}-(3-nitro-phenyl)-amine,
4-{4-(4-Methyl-2-phenyl-thiazol-5-yl)-pyrimidin-2-ylamino}-phenol,
(4-Fluoro-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-phenol,
(4-Iodo-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-2-nitro-phenol,
2-Chloro-4-{4-(4-methyl-2-methylamino-thiazol-5-yl)-pyrimidin-2-ylamino}-benzoic acid ethyl ester,
{4-(2-Ethylamino-4-methyl-thiazol-5-yl)-pyrimidin-2-yl}-(4-fluoro-phenyl)-amine,
{4-(4-Methyl-2-methylamino-thiazol-5-yl)-pyrimidin-2-yl}-(3-nitro-phenyl)-amine,
{4-(2-Allylamino-4-methyl-thiazol-5-yl)-pyrimidin-2-yl}-(4-fluoro-phenyl)-amine,
(3-Bromo-phenyl)-{4-(4-methyl-2-methylamino-thiazol-5-yl)-pyrimidin-2-yl}-amine,
{4-(2-Allylamino-4-methyl-thiazol-5-yl)-pyrimidin-2-yl}-(3-nitro-phenyl)-amine,
3-{4-(4-Methyl-2-methylamino-thiazol-5-yl)-pyrimidin-2-ylamino}-phenol,
(4-Bromo-phenyl)-4-(4-methyl-2-methylamino-thiazol-5-yl)-pyrimidin-2-yl}-amine,
(4-Chloro-phenyl)-{4-(4-methyl-2-methylamino-thiazol-5-yl)-pyrimidin-2-yl}-amine,
(3-Methoxy-phenyl)-{4-(4-methyl-2-methylamino-thiazol-5-yl)-pyrimidin-2-yl}-amine,
{4-(4-Methyl-2-methylamino-thiazol-5-yl)-pyrimidin-2-yl}-(4-trifluoromethyl-phenyl)-amine,
{4-(4-Methyl-2-methylamino-thiazol-5-yl)-pyrimidin-2-yl}-(3-trifluoromethyl-phenyl)-amine,
5-{4-(2,4-Dimethyl-thiazol-5-yl)-pyrimidin-2-ylamino}-2-fluoro-benzoic acid 2-methoxy-ethyl ester,
2-Chloro-5-{4-(2,4-dimethyl-thiazol-5-yl)-pyrimidin-2-ylamino}-benzoic acid methyl ester,
(3,5-Difluoro-phenyl)-{4-(4-methyl-2-methylamino-thiazol-5-yl)-pyrimidin-2-yl}-amine,
(4-Chloro-3-trifluoromethyl-phenyl)-{4-(4-methyl-2-methylamino-thiazol-5-yl)-pyrimidin-2-yl}-amine,
(3-Chloro-phenyl)-{4-(4-methyl-2-methylamino-thiazol-5-yl)-pyrimidin-2-yl}-amine,
(4-Methoxy-phenyl)-{4-(4-methyl-2-methylamino-thiazol-5-yl)-pyrimidin-2-yl}-amine,
2-{4-(2,4-Dimethyl-thiazol-5-yl)-pyrimidin-2-ylamino}-5-methoxy-phenol,
(3-Fluoro-phenyl)-{4-(4-methyl-2-methylamino-thiazol-5-yl)-pyrimidin-2-yl}-amine,
(3,4-Difluoro-phenyl)-{4-(4-methyl-2-methylamino-thiazol-5-yl)-pyrimidin-2-yl}-amine,
N-{3-{4-(2,4-Dimethyl-thiazol-5-yl)-pyrimidin-2-ylamino}-phenyl}-guanidine,
{4-(2,4-Dimethyl-thiazol-5-yl)-pyrimidin-2-yl}-(4-pyridin-4-ylmethyl-phenyl)-amine,
N,N-Dimethyl-N'-{4-(2,4-dimethyl-thiazol-5-yl)-pyrimidin-2-yl}-benzene-1,4-diamine,
{4-{4-(2,4-Dimethyl-thiazol-5-yl)-pyrimidin-2-ylamino}-phenyl}-trimethyl-ammonium.

Even more preferred compounds observed to be CDK inhibitors include the following:

{4-(2,4-Dimethyl-thiazol-5-yl)-pyrimidin-2-yl}-(4-trifluoromethyl-phenyl)-amine,
(4-Bromo-phenyl)-{4-(2,4-dimethyl-thiazol-5-yl)-pyrimidin-2-yl}-amine,
4-{4-(4-Methyl-2-methylamino-thiazol-5-yl)-pyrimidin-2-ylamino}-phenol,
(4-Fluoro-phenyl)-{4-(4-methyl-2-methylamino-thiazol-5-yl)-pyrimidin-2-yl}-amine.

The following compounds are observed to be particularly effective anti-proliferative agents, as demonstrated by cell-based assays:

(2-Chloro-phenyl)-{4-(2,5-dichloro-thiophen-3-yl)-pyrimidin-2-yl}-amine,
(4-Chloro-phenyl)-{4-(2,5-dichloro-thiophen-3-yl)-pyrimidin-2-yl}-amine,
(3-Chloro-phenyl)-{4-(2,5-dichloro-thiophen-3-yl)-pyrimidin-2-yl}-amine,
(2-Chloro-phenyl)-{4-(2,5-dimethyl-thiophen-3-yl)-pyrimidin-2-yl}-amine,
(3,5-Dichloro-phenyl)-{4-(2,4-dimethyl-thiazol-5-yl)-pyrimidin-2-yl}-amine,
(2,4-Dichloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-trifluoromethyl-phenyl)-amine,
{4-(2,4-Dimethyl-thiazol-5-yl)-pyrimidin-2-yl}-(2-trifluoromethyl-phenyl)-amine,
{4-(2,4-Dimethyl-thiazol-5-yl)-pyrimidin-2-yl}-(2-iodo-phenyl)-amine,
{4-(2,4-Dimethyl-thiazol-5-yl)-pyrimidin-2-yl}-(4-iodo-phenyl)-amine,
N-{4-(2,4-Dimethyl-thiazol-5-yl)-pyrimidin-2-yl}-3-nitro-benzenesulfonamide,
{4-(2,4-Dimethyl-thiazol-5-yl)-6-phenyl-pyrimidin-2-yl}-(3-nitro-phenyl)-amine,
(3,4-Difluoro-phenyl)-{4-(4-methyl-2-phenyl-thiazol-5-yl)-pyrimidin-2-yl}-amine,
(4-Chloro-phenyl)-{4-(2,4-dimethyl-thiazol-5-yl)-6-(4-trifluoromethyl-phenyl)-pyrimidin-2-yl}-amine,
4-{6-(2,4-Dimethyl-thiazol-5-yl)-2-(4-fluoro-phenylamino)-pyrimidin-4-yl-2,6-dimethoxy-phenol,
4-{6-(2,4-Dimethyl-thiazol-5-yl)-2-(4-fluoro-phenylamino)-pyrimidin-4-yl}-phenol,
2-Chloro-5-{4-(2,4-dimethyl-thiazol-5-yl)-pyrimidin-2-ylamino}-benzoic acid ethyl ester,
3-Chloro-2-{4-(2,4-dimethyl-thiazol-5-yl)-pyrimidin-2-ylamino}-benzoic acid ethyl ester,
{4-(2,4-Dimethyl-thiazol-5-yl)-pyrimidin-2-yl}-(2-fluoro-4-iodo-phenyl)-amine,
(3-Chloro-4-iodo-phenyl)-{4-(2,4-dimethyl-thiazol-5-yl)-pyrimidin-2-yl}-amine,
4-Chloro-3-{4-(2,4-dimethyl-thiazol-5-yl)-pyrimidin-2-ylamino}-benzoic acid methyl ester,
(3-Iodo-phenyl)-{4-(4-methyl-2-methylaminothiazol-5-yl)-pyrimidin-2-yl}-amine,
(2,4-Difluoro-phenyl)-{4-(4-methyl-2-methylamino-thiazol-5-yl)-pyrimidin-2-yl}-amine.

The following compound is observed to be an even more effective anti-proliferative agent, as demonstrated by cell-based assays: {4-(2,4-dimethyl-thiazol-5-yl)-pyrimidin-2-yl}-(4-iodo-phenyl)-amine.

The compounds of formula I have been found to possess anti-proliferative activity and are therefore believed to be of use in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4) in an appropriate assay. These assays including methods for their performance are described in more detail in Example 23. Using such cell line and enzymes assays it may be determined whether a compound is anti-proliferative in the context of the present invention.

Without wishing to be bound by theory, the compounds of the present invention are believed to exert their anti-proliferative effect in a non-protein kinase C (PKC) dependent manner. Many of the compounds inhibit cyclin-dependent kinase enzymes (CDKs) that have been shown to be involved in cell cycle control. These CDKs include CDK2 and CDK4 and particularly their respective interactions with cyclin E and cyclin D1. These compounds of the present invention are further believed to be advantageous in being selective for CDK enzymes implicated in proliferative diseases. By the term "selective" it is meant that although possible having some inhibitory effect on another enzyme (such as PKC), the compound is preferentially effective against an enzyme implicated in proliferative diseases.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

A further embodiment of the present invention therefore relates to the use of one or more compounds of formula I in the treatment of proliferative disorders. Preferably, the proliferative disorder is a cancer or leukaemia. The term proliferative disorder is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required.

In a particularly preferred embodiment, the invention relates to the use of one or more compounds of formula I in the treatment of a CDK dependent or sensitive disorder. CDK dependent disorders are associated with an above normal level of activity of one or more CDK enzymes. Such disorders preferably associated with an abnormal level of activity of CDK2 and/or CDK4. A CDK sensitive disorder is a disorder in which an aberration in the CDK level is not the primary cause, but is downstream of the primary metabolic aberration. In such scenarios, CDK2 and/or CDK4 can be said to be part of the sensitive metabolic pathway and CDK inhibitors may therefore be active in treating such disorders. Such disorders are preferably cancer or leukaemic disorders.

A second aspect of the present invention relates to the use of one or more compounds of formula

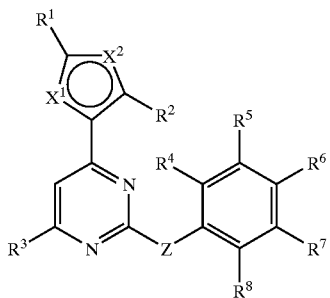

I wherein:
$X^1$ is CH and $X^2$ is S; or
one of $X^1$ and $X^2$ is S, and the other of $X^1$ and $X^2$ is N;
Z is NH, NHCO, NHSO$_2$, NHCH$_2$, CH$_2$, CH$_2$CH$_2$, or CH=CH;
$R^1$, $R^2$, and $R^3$ are independently H, alkyl, aryl, aralkyl, heterocycle, halogeno, NO$_2$, CN, OH, alkoxy, aryloxy, NH$_2$, NH—R', N—(R')(R"), NH-aryl, N-(aryl)$_2$, COOH, COO—R', COO-aryl, CONH$_2$, CONH—R', CON—(R')(R"), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogeno, NO$_2$, CN, OH, O-methyl, NH$_2$, COOH, CONH$_2$ and CF$_3$;
$R^4$, $R^5$, $R^6$, $R^7$, and $R^8$ are independently from each other H, substituted or unsubstituted lower alkyl, halogeno, NO$_2$, CN, OH, substituted or unsubstituted alkoxy, NH$_2$, NH—R', N—(R')(R"), COOH, COO—R', CONH$_2$, CONH—R', CON—(R')(R"), SO$_3$H, SO$_2$NH$_2$, or CF$_3$, other than when $R^5$, $R^6$ and $R^7$ are all methoxy and $R^4$ and $R^8$ are hydrogen or when $R^6$ and $R^7$ are both methoxy and $R^4$, $R^5$ and $R^8$ are all hydrogen;
wherein R' and R" are each independently alkyl groups that may be the same or different;
and pharmaceutically acceptable salts thereof;
in the manufacture of a medicament for use in the treatment of a proliferative disease.

The term "proliferative disorder" has been previously discussed and the same definition applies to the second aspect of the invention.

The preferred embodiments of this further aspect of the invention are identical to those described above in respect of the first aspect.

In a particularly preferred embodiment, the one or more compounds of the invention are administered in combination with one or more other anticancer agents. In such cases, the compounds of the invention may be administered consecutively, simultaneously or sequentially with the one or more other anticancer agents.

As used herein the phrase "manufacture of a medicament" includes the use of a compound of formula I directly as the medicament in addition to its use in a screening programme for further anti-proliferative agents or in any stage of the manufacture of such a medicament.

The compounds of the present invention (first and seconds aspects) can be present as salts or esters, in particular pharmaceutically acceptable salts or esters.

Pharmaceutically acceptable salts of the compounds of the invention (first and seconds aspects) include suitable acid addition or base salts thereof. A review of suitable pharmaceutical salts may be found in Berge et al, J Pharm Sci, 66, 1–19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C$_1$-C$_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C$_1$-C$_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1–12 carbon atoms which may be unsubstituted or substituted, e.g. by a halogen).

In all aspects of the present invention previously discussed, the invention includes, where appropriate all enantiomers and tautomers of compounds of formula I. The man skilled in the art will recognise compounds that possess an optical properties (one or more chiral carbon atoms) or tautomeric characteristics. The corresponding enantiomers and/or tautomers may be isolated/prepared by methods known in the art.

The invention furthermore relates to the compounds of or of use in the present invention (first and seconds aspects) in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

The invention further includes the compounds (first and seconds aspects) of or of use in the present invention in prodrug form. Such prodrugs are generally compounds of formula I wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

The present invention also encompasses pharmaceutical compositions comprising the compounds of the invention (first and seconds aspects). In this regard, and in particular for human therapy, even though the compounds of the present invention (including their pharmaceutically acceptable salts, esters and pharmaceutically acceptable solvates) can be administered alone, they will generally be administered in admixture with a pharmaceutical carrier, excipient or diluent selected with regard to the intended route of administration and standard pharmaceutical practice.

Thus, the present invention also relates to pharmaceutical compositions comprising one or more compounds of formula I or pharmaceutically acceptable salts or esters thereof, together with at least one pharmaceutically acceptable excipient, diluent or carrier.

By way of example, in the pharmaceutical compositions of the present invention, the compounds of the invention may be admixed with any suitable binder(s), lubricant(s), suspending agent(s), coating agent(s), and/or solubilising agent(s). Examples of such suitable excipients for the various different forms of pharmaceutical compositions described herein may be found in the "Handbook of Pharmaceutical Excipients, $2^{nd}$ Edition, (1994), Edited by A Wade and PJ Weller.

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10–100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10–1000 mg, preferably between 10–250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will vary with the age, weight and response of the particular patient. The dosages disclosed herein are exemplary of the average case. There can of course be individual instances where higher or lower dosage ranges are merited, and such are within the scope of this invention.

In an exemplary embodiment, one or more doses of 10 to 150 mg/day will be administered to the patient for the treatment of malignancy.

The pharmaceutical compositions of the invention may further comprise one or more additional anticancer agents, for example, existing anticancer drugs available on the market.

Anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Suitable anti-proliferative agents or anticancer agents that may be used in combination with at least one compound of the present invention include: DNA damaging agents, antimetabolites, anti-tumour antibiotics, natural products and their analogues, dihydrofolate reductase inhibitors, pyrimidine analogues, purine analogues, cyclin-dependent kinase inhibitors, thymidylate synthase inhibitors, DNA intercalators, DNA cleavers, topoisomerase inhibitors, anthracyclines, vinca drugs, mitomycins, bleomycins, cytotoxic nucleosides, pteridine drugs, diynenes, podophyllotoxins, platinum containing drugs, differentiation inducers, and taxanes. Particularly useful members of those classes include, for example, methotrexate, methopterin, dichloromethotrexate, 5-fluorouracil, 6-mercaptopurine, tri-substituted purines such as olomoucine, roscovitine, bohemine and purvalanol, flavopiridol, staurosporin, cytosine arabinoside, melphalan, leurosine, actinomycin, daunorubicin, doxorubicin, mitomycin D, mitomycin A, caminomycin, aminopterin, tallysomycin, podophyllotoxin (and derivatives thereof), etoposide, cisplatin, carboplatinum, vinblastine, vincristine, vindesin, paclitaxel, docetaxel, taxotere retinoic acid, butyric acid, acetyl spermidine, tamoxifen, irinotecan and camptothecin. Most preferably the drug moiety is selected from methotrexate, podophyllotoxin (and derivatives thereof), etoposide, camptothecin, paclitaxel, doxorubicin, roscovitine and bohemine.

The compounds of this invention (I) can be synthesised, for example, by an adaptation of the Traube synthesis (A. R. Katritzky, I. Taher, *Can. J. Chem.* 1986, 64, 2087 and references cited therein), i.e. by condensation between 1,3-dicarbonyl compounds 1 or acrylates 2 or 3, and amidine 4, as shown in Scheme 1.

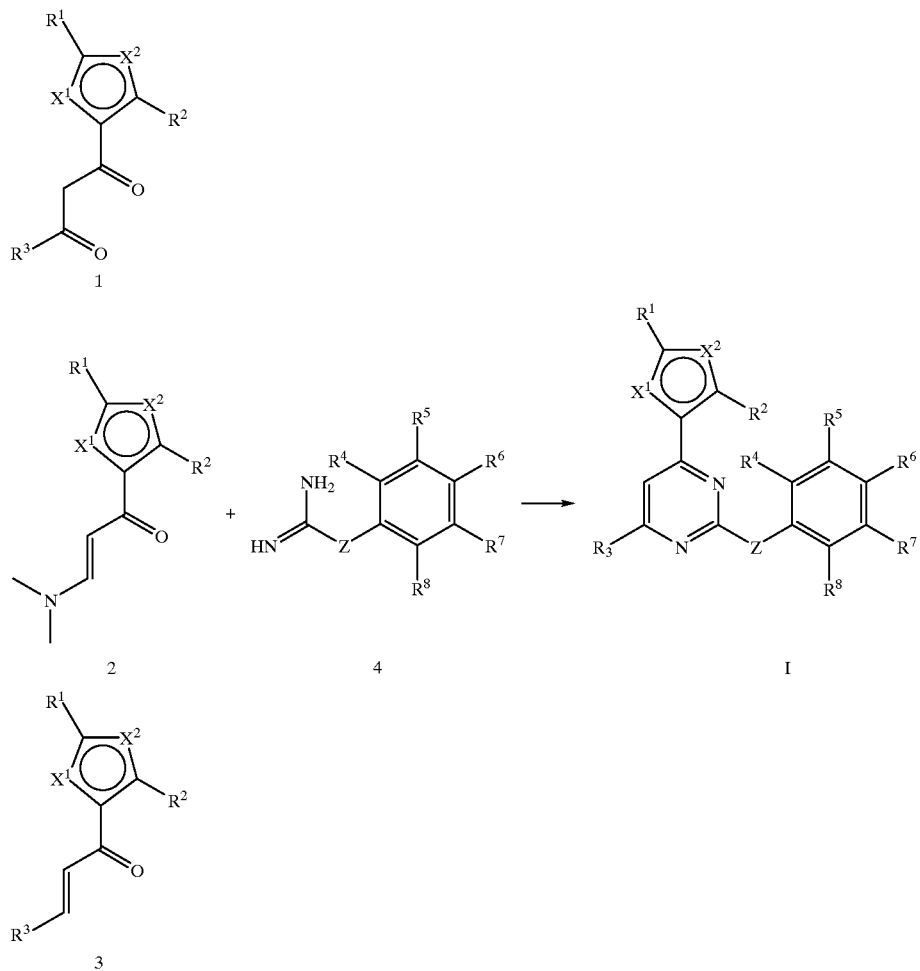

The dicarbonyl compounds 1 in turn can be prepared by many methods known in the art (J. March, In: Advanced Organic Chemistry: Reactions, Mechanism, and Structure, 4th Ed., John Wiley & Sons, Inc., New York, 1992, p. 1283). Acrylates 2 and 3, which are particularly suitable for the purposes of this invention, are obtained from heterocyclic methyl ketones 5 by condensation with dimethylformamide dimethylacetal 6 and aldehydes 7 respectively, (Scheme 2).

Scheme 2

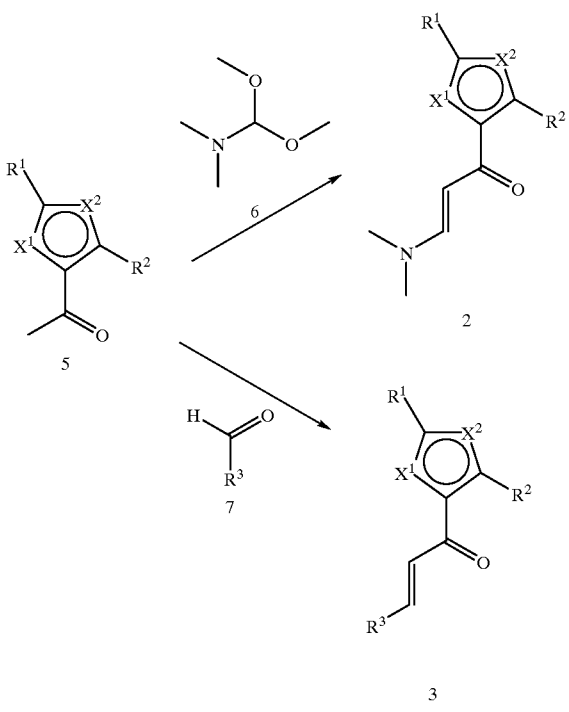

The diamino compounds 4 will be amidines 4a or guanidines 4b, depending on the definition of Z in general structure I. Amidines (HN=CRNH₂) can be obtained from readily available amine precursors by condensation with e.g. ketenimines, or by addition of ammonia to suitable nitriles or imidates. Guanidines 4b (Scheme 3) can be elaborated by a number of methods known in the art. For the purposes of this invention, the most useful route is amination of cyanamide 8 with anilines 9.

Scheme 3

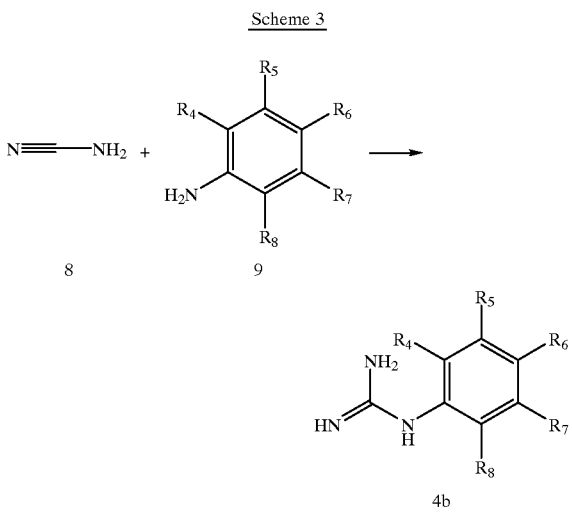

Alternatively, compounds of general structure I can be obtained from suitable pyrimidine precursors directly, e.g. from 2,4-disubstituted (halogen, amine, etc.) pyrimidines by successive substitution reactions.

EXAMPLES

Abbreviations

DE MALDI-TOF MS, delayed extraction matrix assisted laser desorption ionisation time-of-flight mass spectrometry; DMF, N,N-dimethylformamide; LC-MS, liquid chromatography-mass spectrometry; NMR, nuclear magnetic resonance spectroscopy; RP-HPLC, reversed-phase high performance liquid chromatography; r.t. room temperature; PE, petroleum ether (40–60° C. boiling fraction); DMSO, dimethylsulfoxide.

General

NMR spectra were recorded using a Bruker DPX-300 instrument. Chemical shifts are reported in ppm (δ) from tetramethylsilane. EM Kieselgel 60 (0.040–0.063 mm) was used for flash column chromatography. Melting points were determined with a LEICA testo-720 electrothermometer and are uncorrected. Compound numbers are shown in brackets, where appropriate.

Example 1

3-Dimethylamino-1-(2,5-dimethyl-thiophen-3-yl)-propenone

A solution of 3-acetyl-2,5-dimethylthiophene (0.1 mol, 15.4 g) in N,N-dimethylformamide dimethylacetal (14.6 mL) was refluxed under $N_2$ for 16 h. The reaction mixture was evaporated to dryness. The residue was triturated with $iPr_2O$, the resulting solid was filtered and washed with the same solvent twice to afford the title compound as a yellow solid (8.60 g, 41%). $^1$H-NMR (300 MHz, $CDCl_3$) δ 2.40 (s, 6H, $CH_3$), 2.63 (s, 6H, $CH_3$), 5.42 (d, 1H, J=12.5 Hz, CH) 6.89 (s, 1H, Ar-H), 7.66 (d, 1H, J=12.5 Hz, CH).

4-(2,5-Dimethyl-thiophen-3-yl)-pyrimidin-2-ylamine

A mixture of 3-dimethylamino-1-(2,5-dimethyl-thiophen-3-yl)-propenone (3.5 mmol, 0.733 g) and guanidine carbonate (3.5 mmol, 0.631 g) in 2-methoxyethanol was refluxed under $N_2$ for 21 h. The solvent was evaporated to dryness and the residue was purified by flash chromatography, using EtOAc/PE (5:1, v/v) to elute the product, which was then recrystallised from acetone to afford the title compound as light-yellow crystals (331 mg, 46%). $^1$H-NMR (300 MHz, $CDCl_3$) δ 2.43 (s, 3H, $CH_3$), 2.64 (s, 3H, $CH_3$), 5.05 (br, 2H, $NH_2$), 6.74 (d, 1H, J=5.2 Hz, pyrimidinyl-H), 6.97 (s, 1H, thienyl-H), 8.28 (d, 1H, J=5.2 Hz, pyrimidinyl-H).

Example 2

N-(4-Chloro-phenyl)-guanidine nitrate

A solution of 4-chloroaniline (70 mmol, 8.88 g) in EtOH (5 mL) on an ice bath was treated with nitric acid (69% aq soln.; 5 mL). To this mixture cyanamide (50% aq. soln.; 5.4 mL) was added. The reaction mixture was stirred at r.t. for 10 min and then refluxed under $N_2$ for a further 22 h. The solvent was evaporated. The dark brown solid residue was washed with EtOH and was dried under high vacuum to afford the title compound as a white powder (7.16 g, 44%). $^1$H-NMR (300 MHz, $d_6$-DMSO) δ 7.27–7.54 (m, 4H, Ph-H), 9.65 (br. s, 2H, NH).

(4-Chloro-phenyl)-{4-(2,5-dichloro-thiophen-3-yl)-pyrimidin-2-yl}-amine {3}

A mixture of 1-(2,5-dichloro-thiophen-3-yl)-3-dimethylamino-propenone (1.2 mmol, 0.29 g) and N-(4-chloro-phenyl)-guanidine nitrate (1.2 mmol, 0.27 g) in iPrOH (5 mL) was treated with NaOH (48 mg). The reaction mixture was refluxed under $N_2$ for 20 h. The solvent was evaporated and the residue was purified by flash chromatography (EtOAc/PE, 5:1 and 10:3) to afford the title compound as a light yellow solid. Recrystallisation from EtOAc/PE gave pure product (283 mg, 66%). $^1$H-NMR (300 MHz, CDCl$_3$) δ 7.30–7.35 (m, 4H, Ph-H), 7.61 (m, 2H, Ph-H), 8.48 (d, 1H, J=5.2 Hz, pyrimidyl-H).

The following compounds were prepared in a manner analogous to that described above:

(2-Chloro-phenyl)-{4-(2,5-dichloro-thiophen-3-yl)-pyrimidin-2-yl}-amine {2}

$^1$H-NMR (300 MHz, CDCl$_3$) δ 6.99 (m, 1H, Ph-H), 7.29–7.42 (m, 4H, Ph-H, thienyl-H, and pyrimidinyl-H), 8.53 (d, 1H, J=5.2 Hz, pyrimidinyl-H), 8.57 (m, 1H, Ph-H).

(3-Chloro-phenyl)-{4-(4-(2,5-dichloro-thiophen-3-yl)-pyrimidin-2-yl}-amine {4}

$^1$H-NMR (300 MHz, CDCl$_3$) δ 7.02 (m, 1H, Ph-H), 7.23–7.40 (m, 4H, Ph-H, thienyl-H and pyrimidinyl-H), 7.93 (t, 1H, J=1.99, 3.95 Hz, Ph-H), 8.50 (d, 1H, J=5.2 Hz, pyrimidinyl-H), (4-Chloro-phenyl)-{4-(2,5-dimethyl-thiophen-3-yl)-pyrimidin-2-yl}-amine {14}

$^1$H-NMR (300 MHz, CDCl$_3$) δ 2.45 (s, 3H, CH$_3$), 2.66 (s, 3H, CH$_3$), 6.87 (d, 1H, J=5.3 Hz, pyrimidinyl-H), 7.01 (s, 1H, thienyl-H), 7.29 (m, 2H, Ph-H), 7.60 (m, 2H, Ph-H), 8.40 (d, 1H, J=5.3 Hz, pyrimidinyl-H).

(2-Chloro-phenyl)-{4-(2,5-dimethyl-thiophen-3-yl)-pyrimidin-2-yl}-amine {14}

$^1$H-NMR (300 MHz, CDCl$_3$) δ 2.45 (s, 3H, CH$_3$), 2.68 (s, 3H, CH$_3$), 6.91 (d, 1H, J=5.2 Hz, pyrimidinyl-H), 6.97 (m, 1H, Ph-H), 7.04 (s, 1H, thienyl-H), 7.28 (m, 1H, Ph-H), 7.38 (m, 2H, Ph-H), 8.44 (d, 1H, J=5.2 Hz, pyrimidinyl-H), 8.60 (m, 1H, Ph-H).

(3-Chloro-phenyl)-(4-(2,5-dimethyl-thiophen-3-yl)-pyrimidin-2-yl}-amine {16}

$^1$H-NMR (300 MHz, CDCl$_3$) δ 2.45 (s, 3H, CH$_3$), 2.70 (s, 3H, CH$_3$), 6.90 (d, 1H, J=5.2 Hz, pyrimidinyl-H), 7.20–7.33 (m, 3H, Ph-H and thienyl-H), 7.34 (m, 1H, Ph-H), 7.96 (m, 1H, Ph-H), 8.42 (d, 1H, J=5.2 Hz, pyrimidinyl-H).

{4-(2,5-Dichloro-thiophen-3-yl)-pyrimidin-2-yl}-(3-nitro-phenyl)-amine {9}

$^1$H-NMR (300 MHz, d$_6$-DMSO) δ 7.43 (d, 1H, J=5.2 Hz, pyrimidinyl-H), 7.59 (m, 1H, Ph-H), 7.67 (m, 1H, Ph-H), 7.82 (m, 1H, Ph-H), 8.04 (m, 1H, Ph-H), 8.70 (d, 1H, J=5.2 Hz, pyrimidinyl-H), 9.03 (s, 1H, thienyl-H).

Example 3

3-Dimethylamino-1-(2,4-dimethyl-thiazol-5-yl)-propenone

A solution of 5-acetyl-2,4-dimethylthiazole (10 g, 60 mmol) in N,N-dimethylformamide dimethylacetal (10 mL) was refluxed under N$_2$. After 18 h, the reaction mixture was evaporated to dryness and the residue was recrystallised from iPr$_2$O/CH$_2$Cl$_2$ to afford the title compound as a brown powder (9.94 g, 79%). $^1$H-NMR (300 MHz, CDCl$_3$) δ 2.66 (s, 6H, CH$_3$), 2.70 (s, 6H, CH$_3$), 5.37 (d, 1H, J=12.2 Hz, CH), 7.66 (d, 1H, J=12.2 Hz, CH).

Example 4

N-(3-Nitro-phenyl)-guanidine nitrate

A mixture of 3-nitroaniline (50 mmol, 6.90 g) in EtOH (10 mL) was cooled on an ice bath. Nitric acid (69% aq. soln.; 3.6 mL) was added dropwise. To this mixture cyanamide (50% aq soln.; 5 mL) was added. The reaction mixture was stirred at r.t. for 10 min and was then refluxed under N$_2$ for a further 22 h. The solvent was evaporated. The dark brown solid was washed with EtOAc/EtOH and dried under high vacuum overnight to afford the title compound as a brown solid (6.90 g, 57%). $^1$H-NMR (300 MHz, DMSO-d$_6$) δ 7.66–7.75 (m, 2H, Ph-H), 8.09–8.14 (m, 2H, Ph-H).

{4-(2,4-Dimethyl-thiazol-5-yl)-pyrimidin-2-yl}-(3-nitro-phenyl)-amine {12}

A mixture of 3-dimethylamino-1-(2,4-dimethyl-thiazol-5-yl)-propenone (1.0 mmol, 0.21 g) and N-(3-nitro-phenyl)-guanidine nitrate (1.0 mmol, 0.24 g) in 2-methoxyethanol (5 mL) was treated with NaOH (40 mg). The reaction mixture was refluxed under N$_2$ for 20 h. The solvent was evaporated and the residue was purified by flash chromatography (EtOAc/PE, 5:1) and recrystallisation from EtOAc/MeOH to afford the title compound as a yellow solid (151 mg, 46%). M.p. 176–178° C. LC-MS: m/z=328 (M+1). C$_{15}$H$_{13}$N$_5$O$_2$S requires: C, 55.03; H, 4.00; N, 21.39; found: C, 54.67; H, 3.88; N, 21.77. $^1$H-NMR (300 MHz, CDCl$_3$) δ 2.72 (s, 3H, CH$_3$), 2.74 (s, 3H, CH$_3$), 7.06 (d, 1H, J=5.3 Hz, pyrimidinyl-H), 7.74–7.92 (m, 3H, Ph-H), 8.46 (d, 1H, J=5.3 Hz, pyrimidinyl-H), 8.91 (t, 1H, J=4.3, 2.1 Hz, Ph-H).

Example 5

N-(4-Fluoro-phenyl)-guanidine nitrate

A solution of 4-fluoroaniline (25 mmol, 2.80 g) in EtOH (10 mL) was cooled on an ice bath. Nitric acid (69% aq. soln.; 1.8 mL) was added dropwise. Then cyanamide (50% aq. soln.; 4 mL) was added. The reaction mixture was refluxed under N$_2$ for 21 h. The solvent was evaporated to dryness. The solid residue was washed with EtOH and dried under high vacuum overnight to afford the title compound as a purple powder (2.54 g, 47%). This material was used for subsequent reaction without further purification.

{4-(2,4-Dimethyl-thiazol-5-yl)-pyrimidin-2-yl}-(4-fluoro-phenyl)-amine {21}

To a mixture of 3-dimethylamino-1-(2,4-dimethyl-thiazol-5-yl)-propenone (1.0 mmol, 0.21 g) and N-(4-fluoro-phenyl)-guanidine nitrate (2.0 mmol, 0.44 g) in 2-methoxyethanol (5 mL) was added NaOH (40 mg). The reaction mixture was refluxed under N$_2$ for 24 h. The solvent was evaporated to dryness and the residue was purified by flash chromatography (EtOAc/PE, 2:1) and recrystallisation from EtOAc/PE to afford the title compound as brown crystals (269 mg, 89%). $^1$H-NMR (300 MHz, CDCl$_3$) δ 2.69 (s, 3H, CH$_3$), 2.71 (s, 3H, CH$_3$), 6.93 (d, 1H, J=5.3 Hz, pyrimidinyl-H), 7.03 (m, 2H, Ph-H), 7.58 (m, 2H, Ph-H), 8.40 (d, 1H, J=5.3 Hz, pyrimidinyl-H).

Example 6

N-(2,4-Difluoro-phenyl)-guanidine nitrate

To a mixture of 2,4-difluoroaniline (25 mmol, 3.2 g) in EtOH (10 mL) in an ice bath was added nitric acid (69% aq soln.; 1.8 mL) dropwise. After completion of the addition cyanamide (50% aq. soln.; 4 mL) was added. The reaction mixture was refluxed under N$_2$ for 22 h. The solvent was evaporated. The solid residue was washed with EtOH and was dried under high vacuum to afford the title compound as a purple solid (2.32 g, 40%).

(2,4-Difluoro-phenyl)-{4-(2,4-dimethyl-thiazol-5-yl)-pyrimidin-2-yl}-amine {22}

A mixture of 3-dimethylamino-1-(2,4-dimethyl-thiazol-5-yl)-propenone (1.0 mmol, 0.21 g) and N-(2,4-difluorophenyl)-guanidine nitrate (2 mmol, 0.47 g) in 2-methoxyethanol (5 mL) was treated with NaOH (40 mg). After 24 h refluxing under $N_2$ the solvent was evaporated to dryness and the residue was purified by flash chromatography (EtOAc/PE, 2:1) and recrystallisation from EtOAc/PE to afford the title compound as a brown powder (250 mg, 79%). $^1$H-NMR (300 MHz, CDCl$_3$) δ 2.69 (s, 3H, CH$_3$), 2.71 (s, 3H, CH$_3$), 6.93 (d, 1H, J=5.3 Hz, pyrimidinyl-H), 7.01 (m, 2H, Ph-H), 7.58 (m, 2H, Ph-H), 8.40 (d, 1H, J=5.3 Hz, pyrimidinyl-H).

Example 7

N-(4-Hydroxy-2-nitro-phenyl)-guanidine nitrate

A mixture of 4-amino-2-nitrophenol (25 mmol, 3.85 g) in EtOH (6 mL) on an ice bath was treated with nitric acid (69% aq soln.; 1.8 mL). To this of cyanamide (50% aq. soln.; 4 mL) was added. The reaction mixture was refluxed under $N_2$ for 22 h. The solvent was evaporated. The dark brown solid residue was washed with EtOH and was dried under high vacuum to afford the title compound as a grey solid (3.53 g, 54%).

4-{4-(2,4-Dimethyl-thiazol-5-yl)-pyrimidin-2-ylamino}-2-nitro-phenol {45}

3-Dimethylamino-1-(2,4-dimethyl-thiazol-5-yl)-propenone (1 mmol, 0.21 g) in 2-methoxyethanol (5 mL) was treated with N-(4-hydroxy-2-nitro-phenyl)-guanidine nitrate (2 mmol, 0.52 g) in the presence of NaOH (40 mg). The reaction mixture was refluxed under $N_2$ for 24 h. The solvent was evaporated to dryness and the residue was purified by flash chromatography (EtOAc) and recrystallisation from EtOAc/PE to afford the title compound as a yellow powder (61 mg). $^1$H-NMR (300 MHz, CDCl$_3$) δ 2.71 (s, 3H, CH$_3$), 2.73 (s, 3H, CH$_3$), 7.01 (d, 1H, J=5.2 Hz, pyrimidinyl-H), 7.18 (m, 1H, Ph-H), 7.64 (m, 1H, Ph-H), 8.42 (d, 1H, J 5.2 Hz, pyrimidinyl-H), 8.75 (d, 1H, J=2.7 Hz, Ph-H), 10.45 (br. s, 1H, OH).

The following compounds were prepared in a manner analogous to that described above:

(2-Chloro-phenyl)-{4-(2,4-dimethyl-thiazol-5-yl)-pyrimidin-2-yl}-amine {5}

$^1$H-NMR (300 MHz, CDCl$_3$) δ 2.71 (s, 3H, CH$_3$), 2.72 (s, 3H, CH$_3$), 6.96–7.02 (m, 2H, pyrimidinyl-H and Ph-H), 7.30–7.42 (m, 2H, Ph-H), 8.46 (d, 1H, J=5.3 Hz, pyrimidinyl-H). 8.54–8.58 (m, 1H, Ph-H).

(3-Chloro-phenyl)-{4-(2,4-dimethyl-thiazol-5-yl)-pyrimidin-2-yl}-amine {7}

$^1$H-NMR (300 MHz, CDCl$_3$) δ 2.71 (s, 6H, CH$_3$), 6.97–7.04 (m, 2H, pyrimidinyl-H and Ph-H), 7.23–7.36 (m, 2H, Ph-H), 7.94 (t, 1H, J=1.9, 3.9 Hz, Ph-H), 8.43 (d, 1H, J=5.3 Hz, pyrimidinyl-H).

(4-Chloro-phenyl)-{4-(2,4-dimethyl-thiazol-5-yl)-pyrimidin-2-yl}-amine {6}

$^1$H-NMR (300 MHz, CDCl$_3$) δ 2.70 (s, 3H, CH$_3$), 2.71 (s, 3H, CH$_3$), 6.96 (d, 2H, J=5.3 Hz, pyrimidinyl-H), 7.33 (m, 2H, Ph-H), 7.60 (m, 2H, Ph-H), 8.42 (d, 1H, J=5.3 Hz, pyrimidinyl-H).

{4-(2,4-Dimethyl-thiazol-5-yl)-pyrimidin-2-yl}-(2-fluoro-phenyl)-amine {20}

$^1$H-NMR (300 MHz, CDCl$_3$) δ 2.71 (s, 3H, CH$_3$), 2.72 (s, 3H, CH$_3$), 6.98–7.22 (m, 4H, pyrimidinyl-H and Ph-H), 8.45 (d, 1H, J=5.3 Hz, pyrimidinyl-H). 8.50 (m, 1H, Ph-H).

{4-(2,4-Dimethyl-thiazol-5-yl)-pyrimidin-2-yl}-(3-fluoro-phenyl)-amine {35}

$^1$H-NMR (300 MHz, CDCl$_3$) δ 2.71 (s, 3H, CH$_3$), 2.72 (s, 3H, CH$_3$), 6.75 (m, 1H, Ph-H), 7.00 (d, 1H, J=5.3 Hz, pyrimidinyl-H), 7.17–7.32 (m, 3H, Ph-H), 7.77 (m, 1H, Ph-H), 8.44 (d, 1H, J=5.3 Hz, pyrimidinyl-H).

(3,5-Difluoro-phenyl)-{4-(2,4-dimethyl-thiazol-5-yl)-pyrimidin-2-yl}-amine {23}

$^1$H-NMR (300 MHz, CDCl$_3$) δ 2.71 (s, 3H, CH$_3$), 2.73 (s, 3H, CH$_3$), 6.49 (m, 1H, Ph-H), 7.02 (d, 1H, J=5.3 Hz, pyrimidinyl-H), 7.28–7.34 (m, 2H, Ph-H), 8.46 (d, 1H, J=5.3 Hz, pyrimidinyl-H).

(3,5-Dichloro-phenyl)-{4-(2,4-dimethyl-thiazol-5-yl)-pyrimidin-2-yl}-amine {24}

$^1$H-NMR (300 MHz, CDCl$_3$) δ 2.72 (s, 6H, CH$_3$), 7.01–7.04 (m, 2H, pyrimidinyl-H and Ph-H), 7.67 (m, 2H, Ph-H), 8.45 (d, 1H, J=5.3 Hz, pyrimidinyl-H).

(2,4-Dichloro-phenyl)-{4-(2,4-dimethyl-thiazol-5-yl)-pyrimidin-2-yl}-amine {25}

$^1$H-NMR (300 MHz, CDCl$_3$) δ 2.71 (s, 3H, CH$_3$), 2.72 (s, 3H, CH$_3$), 7.02 (d, 1H, J=5.3 Hz, pyrimidinyl-H), 7.29–7.42 (m, 2H, Ph-H), 8.46 (d, 1H, J=5.3 Hz, pyrimidinyl-H), 8.54 (d, 1H, J=8.9 Hz, Ph-H).

{4-(2,4-Dimethyl-thiazol-5-yl)-pyrimidin-2-yl]-(2-trifluoromethyl-phenyl)-amine {27}

$^1$H-NMR (300 MHz, CDCl$_3$), 2.69 (s, 3H, CH$_3$), 2.70 (s, 3H, CH$_3$), 7.00 (d, 1H, J=5.3 Hz, pyrimidinyl-H), 7.19 (m, 1H, Ph-H), 7.59–7.65 (m, 2H, Ph-H), 8.37 (d, 1H, J =6.4 Hz, Ph-H), 8.44 (d, 1H, J=5.3 Hz, pyrimidinyl-H).

{4-(2,4-Dimethyl-thiazol-5-yl)-pyrimidin-2-yl}-(3-trifluoromethyl-phenyl)-amine {26}

$^1$H-NMR (300 MHz, CDCl$_3$) δ 2.71 (s, 3H, CH$_3$), 2.72 (s, 3H, CH$_3$), 7.01 (d, 1H, J=5.3 Hz, pyrimidinyl-H), 7.29–7.34 (m, 2H, Ph-H), 7.45 (m, 1H, Ph-H), 7.64 (m, 1H, Ph-H), 8.45 (d, 1H, J=5.3 Hz, pyrimidinyl-H).

{4-2,4-Dimethyl-thiazol-5-yl)-pyrimidin-2-yl}-(4-trifluoromethyl-phenyl)-amine {28}

Orange solid. M.p. 183–185° C. LC-MS: m/z=351.4 (M+1). $C_{16}H_{13}F_3N_4S$ requires: C, 54.85; H, 3.74; N, 15.99; found: C, 54.71; H, 3.59; N, 16.26. $^1$H-NMR (300 MHz, CDCl$_3$) δ 2.72 (s, 3H, CH$_3$), 2.73 (s, 3H, CH$_3$), 7.03 (d, 1H, J=5.3 Hz, pyrimidinyl-H), 7.60 (m, 2H, Ph-H), 7.79 (m, 2H, Ph-H), 8.46 (d, 1H, J=5.3 Hz, pyrimidinyl-H).

(2-Bromo-phenyl)-{4-(2,4-dimethyl-thiazol-5-yl)-pyrimidin-2-yl}-amine {29}

$^1$H-NMR (300 MHz, CDCl$_3$), 2.71 (s, 3H, CH$_3$), 2.72 (s, 3H, CH$_3$), 6.92 (m, 1H, Ph-H), 7.00 (d, 1H, J=5.3 Hz, pyrimidinyl-H), 7.38 (m, 1H, Ph-H), 7.59 (m, 2H, Ph-H), 8.46 (d, 1H, J=5.3 Hz, pyrimidinyl-H), 8.51 (m, 1H, Ph-H).

(3-Bromo-phenyl)-{4-(2,4-dimethyl-thiazol-5-yl)-pyrimidin-2-yl}-amine {30}

$^1$H-NMR (300 MHz, CDCl$_3$) δ 2.72 (s, 6H, CH$_3$), 6.98 (d, 1H, J=5.3 Hz, pyrimidinyl-H), 7.19 (m, 2H, Ph-H), 7.41 (m, 1H, Ph-H), 8.11 (m, 1H, Ph-H), 8.44 (d, 1H, J=5.3 Hz, pyrimidinyl-H).

(4-Bromo-phenyl)-{4-(2,4-dimethyl-thiazol-5-yl)-pyrimidin-2-yl}-amine {31}

Yellow solid. M.p. 173–175° C. LC-MS: m/z=363 (M+1). $C_{15}H_{13}BrN_4S$ requires: C, 49.87; H, 3.63; N, 15.51; found: C, 49.81; H, 3.61; N, 15.56. $^1$H-NMR (300 MHz, CDCl$_3$) δ 2.70 (s, 3H, CH3), 2.72 (s, 3H, CH3), 6.97 (d, 1H, J=5.3 Hz, pyrimidinyl-H), 7.47 (m, 2H, Ph-H), 7.55 (m, 2H, Ph-H), 8.42 (d, 1H, J=5.3 Hz, pyrimidinyl-H).

{4-(2,4-Dimethyl-thiazol-5-yl)-pyrimidin-2-yl}-(2-iodo-phenyl)-amine {32}

$^1$H-NMR (300 MHz, CDCl$_3$) δ 2.70 (s, 3H, CH$_3$), 2.72 (s, 3H, CH$_3$), 6.80 (m, 1H, Ph-H), 6.99 (d, 1H, J=5.3 Hz, pyrimidinyl-H), 7.42 (m, 1H, Ph-H), 7.84 (m, 1H, Ph-H), 8.39 (m, 1H, Ph-H), 8.45 (d, 1H, J=5.3 Hz, pyrimidinyl-H).

{4-(2,4-Dimethyl-thiazol-5-yl)-pyrimidin-2-yl}-(3-iodo-phenyl)-amine {33}

$^1$H-NMR (300 MHz, d$_6$-DMSO) δ : 2.68 (s, 6H, CH$_3$), 7.03 (m, 2H, pyrimidinyl-H and Ph-H), 7.28 (d, 1H, J=7.9 Hz, Ph-H), 7.68 (m, 1H, Ph-H), 8.41 (m, 1H, Ph-H), 8.47 (d, 1H, J=5.3 Hz, pyrimidinyl-H).

{4-(2,4-Dimethyl-thiazol-5-yl)-pyrimidin-2-yl}-(4-iodo-phenyl)-amine {34}

Yellow solid. M.p. 171–173° C. LC-MS:=m/z 409 (M+1). $C_{15}H_{13}IN_4S$ requires: C, 44.13; H, 3.21; N, 13.72; found: C, 44.03; H, 3.17; N, 13.73. $^1$H-NMR (300 MHz, d$_6$-DMSO) δ 2.70 (s, 3H, CH$_3$), 2.72 (s, 3H, CH$_3$), 6.97 (d, 1H, J=5.3 Hz, pyrimidinyl-H), 7.46 (m, 1H, Ph-H), 7.64 (m, 2H, Ph-H), 8.42 (d, 1H, J=5.3 Hz, pyrimidinyl-H).

(3,4-Difluoro-phenyl)-(4-(2,4-dimethyl-thiazol-5-yl)-pyrimidin-2-yl)-amine {36}

$^1$H-NMR (300 MHz, d$_6$-DMSO) δ 2.70 (s, 3H, CH$_3$), 2.72 (s, 3H, CH$_3$), 6.98 (d, 1H, J =5.3 Hz, pyrimidinyl-H), 7.11 (m, 2H, Ph-H), 7.83 (m, 1H, Ph-H), 8.43 (d, 1H, J=5.3 Hz, pyrimidinyl-H).

{4-(2,4-Dimethyl-thiazol-5-yl)-pyrimidin-2-yl/-(3-methoxy-phenyl)-amine {38}

$^1$H-NMR (300 MHz, CDCl$_3$) δ 2.70 (s, 3H, CH$_3$), 2.71 (s, 3H, CH$_3$), 3.86 (s, 3H, OCH$_3$), 6.61 (m, 1H, Ph-H), 6.94 (d, 1H, J=5.3 Hz, pyrimidinyl-H), 7.10–7.28 (m, 3H, Ph-H), 8.42 (d, 1H, J=5.3 Hz, pyrimidinyl-H).

{4-(2,4-Dimethyl-thiazol-5-yl)-pyrimidin-2-yl}-(2-methoxy-phenyl)-amine {37}

$^1$H-NMR (300 MHz, CDCl$_3$) δ 2.71 (s, 3H, CH$_3$), 2.72 (s, 3H, CH$_3$), 3.92 (s, 3H, OCH$_3$), 6.89–7.04 (d, 4H, Ph-H and pyrimidinyl-H), 8.43 (d, 1H, J=5.3 Hz, pyrimidinyl-H), 8.53 (m, 1H, Ph-H).

{4-(2,4-Dimethyl-thiazol-5-yl)-pyrimidin-2-yl}-(4-methoxy-phenyl)-amine {39}

Orange-yellow solid. M.p. 137–139° C. LC-MS: m/z=313 (M+1). $C_{16}H_{16}N_4OS$ requires: C, 61.51; H, 5.16; N, 17.94; found: C, 61.32; H, 5.18; N, 18.36. $^1$H-NMR (300 MHz, CDCl$_3$), 2.68 (s, 3H, CH$_3$), 2.70 (s, 3H, CH$_3$), 3.82 (s, 3H, OCH$_3$), 6.88–6.93 (d, 4H, Ph-H and pyrimidinyl-H), 7.52 (m, 1H, Ph-H), 8.37 (d, 1H, J=5.3 Hz, pyrimidinyl-H).

3-{4-(2,4-Dimethyl-thiazol-5-yl)-pyrimidin-2-ylamino}-phenol {40}

$^1$H-NMR (300 MHz, d$_6$-DMSO) δ 2.67 (s, 3H, CH$_3$), 2.68 (s, 3H, CH$_3$), 6.42 (d, 1H, J =8.0 Hz, Ph-H), 6.94 (d, 1H, J=5.2 Hz, pyrimidinyl-H), 7.05 (m, 1H, Ph-H), 7.24 (m, 2H, Ph-H), 7.99 (m, 1H, Ph-H), 8.43 (d, 1H, J=5.2 Hz, pyrimidinyl-H), 8.99 (br. s, 1H, NH), 9.21 (br. s, 1H, OH).

4-{4-(2,4-Dimethyl-thiazol-5-yl)-pyrimidin-2-ylamino}-phenol {41}

$^1$H-NMR (300 MHz, d$_6$-DMSO) δ 2.61 (s, 3H, CH$_3$), 2.64 (s, 3H, CH$_3$), 6.71 (m, 2H, Ph-H), 6.97 (d, 1H, J=5.2 Hz, pyrimidinyl-H), 7.49 (m, 2H, Ph-H), 7.24 (m, 2H, Ph-H), 8.43 (d, 1H, J=5.2 Hz, pyrimidinyl-H), 9.06 (br. s, 1H, NH), 9.32 (br. s, 1H, OH).

4-{4-(2,4-Dimethyl-thiazol-5-yl)-pyrimidin-2-ylamino}-benzonitrile {48}

$^1$H-NMR (300 MHz, d$_6$-DMSO), δ 2.65 (s, 3H, CH$_3$), 2.67 (s, 3H, CH$_3$), 7.22 (d, 1H, J =5.2 Hz, pyrimidinyl-H), 7.77 (m, 2H, Ph-H), 7.99 (m, 2H, Ph-H), 8.61 (d, 1H, J=5.2 Hz, pyrimidinyl-H), 10.2 (s, 1H, NH).

3-{4-(2,4-Dimethyl-thiazol-5-yl)-pyrimidin-2-ylamino}-benzonitrile {49}

$^1$H-NMR (300 MHz, d$_6$-DMSO) δ 2.71 (s, 3H, CH$_3$), 2.72 (s, 3H, CH$_3$), 7.03 (d, 1H, J =5.2 Hz, pyrimidinyl-H), 7.31–7.45 (m, 2H, Ph-H), 7.67 (m, 1H, Ph-H), 8.29 (m, 1H, Ph-H), 8.45 (d, 1H, J=5.2 Hz, pyrimidinyl-H).

4-{4-(2,4-Dimethyl-thiazol-5-yl)-pyrimidin-2-ylamino}-benzoic acid {53}

$^1$H-NMR (300 MHz, CDCl$_3$) δ 2.65 (s, 3H, CH$_3$), 2.67 (s, 3H, CH$_3$), 7.09 (d, 1H, J=5.3 Hz, pyrimidinyl-H), 7.70 (m, 2H, Ph-H), 7.82 (m, 2H, Ph-H), 8.52 (d, 1H, J=5.3 Hz, pyrimidinyl-H).

4-{4-(2,4-Dimethyl-thiazol-5-yl)-pyrimidin-2-ylamino}-benzoic acid methyl ester {50}

$^1$H-NMR (300 MHz, CDCl$_3$) δ 2.72 (s, 3H, CH$_3$), 2.73 (s, 3H, CH$_3$), 3.91 (s, 3H, OCH$_3$), 7.02 (d, 1H, J=5.3 Hz, pyrimidinyl-H), 7.41 (sbr, 1H, NH), 7.76 (m, 2H, Ph-H), 8.05 (m, 2H, Ph-H), 8.47 (d, 1H, J=5.3 Hz, pyrimidinyl-H).

(3-Chloro-4-methyl-phenyl)-{4-(2,4-dimethyl-thiazol-5-yl)-pyrimidin-2-yl}-amine {51}

$^1$H-NMR (300 MHz, CDCl$_3$) δ 2.45 (s, 3H, CH$_3$), 2.71 (s, 6H, CH$_3$), 6.99 (d, 1H, J=5.3 Hz, pyrimidinyl-H), 7.18–7.32 (m, 2H, Ph-H), 7.82 (m, 1H, Ph-H), 8.41 (d, 1H, J =5.3 Hz, pyrimidinyl-H).

(3-Chloro-4-methoxy-phenyl)-{4-(2,4-dimethyl-thiazol-5-yl)-pyrimidin-2-yl}-amine {52}

$^1$H-NMR (300 MHz, CDCl$_3$) δ 2.70 (s, 3H, CH$_3$), 2.71 (s, 3H, CH$_3$), 3.90 (s, 3H, OCH$_3$), 6.92 (m, 2H, pyrimidinyl-H & Ph-H), 7.10 (sbr, 1H, NH), 7.38 (m, 1H, Ph-H), 7.85 (m, 1H, Ph-H), 8.40 (d, 1H, J=5.3 Hz, pyrimidinyl-H).

5-{4-(2,4-Dimethyl-thiazol-5-yl)-pyrimidin-2-ylamino}-2-fluoro-benzoic acid 2-methoxy-ethyl ester {98}

$^1$H-NMR (300 MHz, d$_6$-DMSO) (2.64 (s, 3H, CH$_3$), 2.66 (s, 3H, CH$_3$), 3.29 (s, 3H, OCH$_3$), 3.66 (m, 2H, CH$_2$), 4.44 (m, 2H, CH$_2$), 7.13 (d, 1H, J=5.3 Hz, pyrimidinyl-H), 7.32 (m, 1H, Ph-H), 7.98 (m, 1H, Ph-H), 8.39 (m, 1H, Ph-H), 8.54 (d, 1H, J=5.3 Hz, pyrimidinyl-H), 9.93 (s, 1 H, NH).

Example 8

4-(2,4-Dimethyl-thiazol-5-yl)-pyrimidin-2-ylamine

This compound was prepared by heating equimolar amounts of 3-dimethylamino-1-(2,4-dimethyl-thiazol-5-yl)- propenone and guanidine in refluxing 2-methoxethanol. $^1$H-NMR (300 MHz, CDCl$_3$), δ 2.67 (s, 3H, CH$_3$), 2.68 (s, 3H, CH$_3$), 5.14 (br, 2H, NH$_2$), 6.83 (d, 1H, J=5.3 Hz, pyrimidinyl-H), 8.30 (d, 1H, J=5.3 Hz, pyrimidinyl-H).

N-{4-(2,4-Dimethyl-thiazol-5-yl)-pyrimidin-2-yl}-3-nitro-benzenesulfonamide {42}

A solution of 4-(2,4-dimethyl-thiazol-5-yl)-pyrimidin-2-ylamine (1 mmol, 0.227 g), 3-nitrobenenesulfonyl chloride (1.5 mmol, 0.33 g) in pyridine (4 mL) was stirred at r.t. for 24 h. The reaction mixture was evaporated to dryness. The dark brown residue was dissolved in EtOAc and was washed with 2M aq HCl solution, water, brine and was dried over MgSO$_4$. Concentration gave a light yellow residue and this was purified by flash chromatography (EtOAc/PE, 5:1) and recrystallisation from EtOAc/MeOH to afford the title compound as yellow crystals (44 mg). $^1$H-NMR (300 MHz, CDCl$_3$) δ 2.68 (s, 3H, CH$_3$), 2.73 (s, 3H, CH$_3$), 7.59 (d, 1H, J=5.3 Hz, pyrimidinyl-H), 7.90 (m, 1H, Ph-H), 8.60 (m, 1H, Ph-H), 8.75 (m, 1H, Ph-H), 8.81 (d, 1H, J=5.4 Hz, pyrimidinyl-H), 9.15 (t, 1H, J=1.98, 3.91 Hz, Ph-H).

Example 9

3-Dimethylamino-1-(4-methyl-2-methylamino-thiazol-5-yl)-propenone

A solution of 3-chloro-2,4-pentadione (2.5 g, 19 mmol) in MeOH (15 mL) treated with N-methyl-2-thiourea (1.67 g, 19 mmol) and pyridine (1.5 mL). The reaction mixture was stirred at r.t. for 2–3 h. The resulting precipitates were filtered and washed with Et$_2$O to afford a white solid product of 5-acetyl-2-methylamino-4-methylthiazol, which was used in the next reaction step without further purification. A mixture of this product (2.05 g) in N,N-dimethylformamide dimethyl acetal (10 mL) was heated at 100–110° C. for 22 h. The reaction mixture was concentrated. The precipitate was collected and washed with EtOAc to afford the title compound as an orange solid. $^1$H-NMR (300 MHz, CDCl$_3$) δ 2.55, 2.94 (s, 6H, CH$_3$), 3.40 (s, 6H, NCH$_3$), 5.29 (d, 1H, J=12.2 Hz, CH), 7.62 (d, 1H, J=12.2 Hz, CH).

Example 10

(4-Fluoro-phenyl)-{4-(4-methyl-2-methylamino-thiazol-5-yl)-pyrimidin-2-yl}-amine {62}

A mixture 3-dimethylamino-1-(4-methyl-2-methylamino-thiazol-5-yl)-propenone (1 mmol, 0.22 g) and N-(4-fluoro-phenyl)-guanidine nitrate (2 mmol, 0.44 g) in 2-methoxyethanol (5 mL) was added NaOH (40 mg). The reaction mixture was heated at 110–120° C. under N$_2$ for 20 h. The solvent was evaporated to dryness and the residue was purified by flash chromatography, using EtOAc/PE (1:1, v/v) to elute the product as a yellow solid. Recrystallisation from EtOAc/MeOH yielded 230 mg brown crystals of pure title compound. $^1$H-NMR (300 MHz, d$_6$-DMSO) δ 2.46 (s, 3H, CH$_3$), 2.86 (d, 3H, CH$_3$), 6.90 (d, 1H, J=5.4 Hz, pyrimidinyl-H), 7.11 (m, 2H, Ph-H), 7.76 (m, 2H, Ph-H), 8.07 (m, 1H, NH), 8.32 (d, 1H, J=5.4 Hz, pyrimidinyl-H), 9.48 (s, 1H, NH).

The following compounds were prepared in a manner analogous to that described above:

4-{4-(4-Methyl-2-methylamino-thiazol-5-yl)-pyrimidin-2-ylamino}-phenol {62}

$^1$H-NMR (300 MHz, CD$_3$OD$_3$) δ 2.53 (s, 3H, CH$_3$), 2.98 (s, 3H, CH$_3$), 6.77 (d, 2H, J=8.8 Hz, Ph-H), 6.86 (d, 1H, J=5.5 Hz, pyrimidinyl-H), 7.44 (d, 2H, J=8.8 Hz, Ph-H), 8.21 (d, 1 H, J=5.5 Hz, pyrimidinyl-H).

(4-Iodo-phenyl)-{4-4-methyl-2-methylamino-thiazol-5-yl)-pyrimidin-2-yl}-amine {72}

Yellow solid. $^1$H-NMR (300 MHz, d$_6$-DMSO) δ 2.50 (s, 3H, CH$_3$), 2.92 (d, 6H, CH$_3$), 6.85 (d, 1H, J=5.4 Hz, pyrimidinyl-H), 7.53 (d, 2H, J=8.8 Hz, Ar-H), 7.65 (d, 2H, J=8.8 Hz, Ar-H), 8.28 (d, 1H, J=5.4 Hz, pyrimidinyl-H) 9.41 (s, 1H, NH).

{4-(4-Methyl-2-methylamino-thiazol-5-yl)-pyrimidin-2-yl}-(3-nitro-phenyl)-amine {76}

Yellow solid. $^1$H-NMR (300 MHz, d$_6$-DMSO) δ 2.80 s, 3H, CH$_3$), 3.09 (s, 3H, CH$_3$), 7.01 (d, 1H, J=5.4 Hz, pyrimidinyl-H), 7.55 (m, 1H, Ph-H), 7.79 (d, 1H, Ph-H), 8.02 (d, 1H, Ph-H), 8.15 (m, 1H, NH), 8.41 (d, 1H, J=5.4 Hz, pyrimidinyl-H), 9.00 (s, 1H, Ph-H), 10.02 (s, 1H, NH). DE MALDI-TOF MS: {M+H}$^+$=345.15 (C$_{15}$H$_{14}$N$_6$O$_2$S requires 342.38).

3-{4-(4-Methyl-2-methylamino-thiazol-5-yl)-pyrimidin-2-ylamino}-phenol {85}

Yellow crystals. $^1$H-NMR (300 MHz, d$_6$-DMSO) δ 2.86 (s, 3H, CH$_3$), 3.24 (s, 3H, CH$_3$), 6.36 (m, 1H, Ph-H), 6.88 (d, 1H, J=5.5 Hz, pyrimidinyl-H), 7.03 (m, 1H, Ph-H), 7.24 (m, 1H, Ph-H), 8.06 (m, 1H, NH), 8.32 (d, 1H, J=4.5 Hz, pyrimidinyl-H), 9.21 (s, 1H, Ph-H), 9.31 (s, 1H, NH). DE MALDI-TOF MS: {M+H}$^+$=315.92 (C$_{15}$H$_{15}$N$_6$OS requires 313.38).

(4-Bromo-phenyl)-{4-(4-methyl-2-methylamino-thiazol-5-yl)-pyrimidin-2-yl}-amine {86}

Yellow-brown solid. $^1$H-NMR (300 MHz, d$_6$-DMSO) δ 2.86 (s, 3H, CH$_3$), 3.09 (s, 3H, CH$_3$), 6.93 (d, 1H, J=5.5 Hz, pyrimidinyl-H), 7.43 (m, 2H, Ph-H), 7.75 (m, 2H, Ph-H), 8.07 (m, 1H, NH), 8.34 (d, 1H, J=5.5 Hz, pyrimidinyl-H), 9.61 (s, 1H, NH). DE MALDI-TOF MS: {M+H}$^+$=378.8 (C$_{15}$H$_{14}$N$_6$SBr requires 376.28).

(4-Chloro-phenyl)-=4-(4-methyl-2-methylamino-thiazol-5-yl)-pyrimidin-2-yl}-amine {87}

Tan crystals. $^1$H-NMR (300 MHz, d$_6$-DMSO) δ 2.87 (s, 3H, CH$_3$), 3.23 (s, 3H, CH$_3$), 6.94 (d, 1H, J=5.3 Hz, pyrimidinyl-H), 7.32 (m, 2H, Ph-H), 7.81 (m, 2H, Ph-H), 8.09 (m, 1H, NH), 8.35 (d, 1H, J=5.7 Hz, pyrimidinyl-H), 9.61 (s, 1H, NH). DE MALDI-TOF MS: {M+H}$^+$=332.1 (C$_{15}$H$_{14}$N$_6$SCl requires 331.8).

(3-Methoxy-phenyl)-{4-(4-methyl-2-methylamino-thiazol-5-yl)-pyrimidin-2-yl}-amine {88}

Light-yellow solid. $^1$H-NMR (300 MHz, d$_6$-DMSO) δ 2.85 (s, 3H, CH$_3$), 3.09 (s, 3H, CH$_3$), 3.78 (s, 3H, CH$_3$), 6.52 (m, 1H, Ph-H), 6.92 (d, 1H, J=5.5 Hz, pyrimidinyl-H), 7.16 (m, 1H, Ph-H), 7.29 (m, 1H, Ph-H), 7.56 (s, 1H, Ph-I), 8.10 (m, 1H, NH), 8.35 (d, 1H, J=5.3 Hz, pyrimidinyl-H), 9.45 (s, 1H, NH). DE MALDI-TOF MS: {M+H}$^+$=327.8 (C$_{16}$H$_{17}$N$_5$OS requires 327.4).

{4-(4-Methyl-2-methylamino-thiazol-5-yl)-pyrimidin-2-yl}-(4-trifluoromethyl-phenyl)-amine {89}

Yellow-brown solid. $^1$H-NMR (300 MHz, d$_6$-DMSO) δ 2.88 (s, 3H, CH$_3$), 3.10 (s, 3H, CH$_3$), 7.01 (d, 1H, J=5.5 Hz, pyrimidinyl-H), 7.62 (m, 2H, Ph-H), 8.01 (m, 2H, Ph-H), 8.12 (m, 1H, NH), 8.40 (d, 1H, J=5.5 Hz, pyrimidinyl-H), 9.91 (s, 1H, NH). DE MALDI-TOF MS: {M+H}$^+$=365.5 ($C_{16}H_{14}N_5SF_3$ requires 365.4).

{4-(4-Methyl-2-methylamino-thiazol-5-yl)-pyrimidin-2-yl}-(3-trifluoromethyl-phenyl)-amine {90}

Yellow-brown solid. $^1$H-NMR (300 MHz, d$_6$-DMSO) δ 2.86 (s, 3H, CH$_3$), 3.11 (s, 3H, CH$_3$), 6.99 (d, 1H, J=5.5 Hz, Ph-H), 7.27 (m, 1H, Ph-H), 7.50 (m, 1H, Ph-H), 7.87 (m, 1H, Ph-H), 8.15 (m, 1H, NH), 8.40 (d, 1H, J=5.4 Hz, pyrimidinyl-H), 8.47 (s, 1H, Ph-H), 9.86 (s, 1H, NH). DE MALDI-TOF MS: {M+H}$^+$=369.8 ($C_{16}H_{14}N_5SF_3$ requires 365.4).

(3-Bromo-phenyl)-{4-(4-methyl-2-methylamino-thiazol-5-yl)-pyrimidin-2-yl}-amine {83}

Yellow solid. $^1$H-NMR (300 MHz, d$_6$-DMSO) δ 2.87 (s, 3H, CH$_3$), 3.11 (s, 3H, CH$_3$), 6.96 (d, 1H, J=5.4 Hz, pyrimidinyl-H), 7.10 (m, 1H, Ph-H), 7.23 (m, 1H, Ph-H), 7.62 (m, 1H, Ph-H), 8.15 (m, 1H, NH), 8.31 (s, 1H, Ph-H), 8.38 (d, 1H, J=5.0 Hz, pyrimidinyl-H), 9.70 (s, 1H, NH). DE MALDI-TOF MS: {M+H}$^+$=377.4 ($C_{15}H_{14}N_6SBr$ requires 376.3).

(3-Chloro-phenyl)-{4-(4-methyl-2-methylamino-thiazol-5-yl)-pyrimidin-2-yl}-amine {108}

Yellow crystals. $^1$H-NMR (300 MHz, d$_6$-DMSO) δ 2.86 (s, 3H, CH$_3$), 3.10 (s, 3H, CH$_3$), 6.95 (d, 2H, J=5.7 Hz, pyrimidinyl-H), 7.29 (m, 1H, Ph-H), 7.61 (m, 1H, Ph-H), 8.14 (s, 1H, Ph-H), 8.38 (d, 1H, J=4.3 Hz, pyrimidinyl-H), 9.72 (s, 1H, NH). DE MALDI-TOF MS: {M+H}$^+$=331.6 ($C_{15}H_{14}N_6SCl$ requires 331.8).

(3-Iodo-phenyl)-{4-(4-methyl-2-methylamino-thiazol-5-yl)-pyrimidin-2-yl}-amine {102}

Yellow crystals. $^1$H-NMR (30 MHz, d$_6$-DMSO) δ 2.88 (s, 3H, CH$_3$), 3.10 (s, 3H, CH$_3$), 6.96 (d, 1H, J=5.3 Hz, pyrimidinyl-H), 7.07 (m, 1H, Ph-H), 7.28 (m, 1H, Ph-H), 7.61 (m, 1H, Ph-H), 8.14 (m, 1H, NH), 8.37 (d, 1H, J=5.3 Hz, pyrimidinyl-H), 8.50 (s, 1H, Ph-H), 9.64 (s, 1H, NH). DE MALDI-TOF MS: {M+H}$^+$=423.3 ($C_{15}H_{14}N_6SI$ requires 423.3).

(3-Fluoro-phenyl)-{4-(4-methyl-2-methylamino-thiazol-5-yl)-pyrimidin-2-yl}-amine {103}

Yellow solid. $^1$H-NMR (300 MHz, d$_6$-DMSO) δ 2.87 (s, 3H, CH$_3$), 3.10 (s, 3H, CH$_3$), 6.74 (m, 1H, Ph-H), 6.97 (d, 1H, J=5.4 Hz, pyrimidinyl-H), 7.29 (m, 1H, Ph-H), 7.47 (m, 1H, Ph-H), 7.87 (m, 1H, Ph-H), 8.12 (m, 1H, NH), 8.38 (d, 1H, J=5.3 Hz, pyrimidinyl-H), 9.71 (s, 1H, NH). DE MALDI-TOF MS: {M+H}$^+$=316.3 ($C_{15}H_{14}N_5SF$ requires 315.4).

(3,3-Difluoro-phenyl)-{4-4-methyl-2-methylamino-thiazol-5-yl)-pyrimidin-2-yl}-amine {106}

Yellow solid. $^1$H-NMR (300 MHz, d$_6$-DMSO) δ 2.87 (s, 3H, CH$_3$), 3.10 (s, 3H, CH$_3$), 6.74 (m, 1H, Ph-H), 7.02 (d, 1H, J=5.5, pyrimidinyl-H), 7.60 (m, 2H, Ph-H), 8.18 (m, 1H, NH), 8.41 (d, 1H, J=5.4 Hz, pyrimidinyl-H), 9.92 (s, 1H, NH). DE MALDI-TOF MS: {M+H}$^+$=333.4 ($C_{15}H_{13}N_5SF_2$ requires 333.4).

(4-Chloro-3-trifluoromethyl-phenyl)-{4-(4-methyl-2-methylamino-thiazol-5-yl)-pyrimidin-2-yl}-amine {107}

Light-yellow crystals. $^1$H-NMR (300 MHz, d$_6$-DMSO) δ 2.86 (s, 3H, CH$_3$), 3.10 (s, 3H, CH$_3$), 7.01 (d, 1H, J=5.4 Hz, pyrimidinyl-H), 7.61 (m, 1H, Ph-H), 7.92 (m, 1H, Ph-H), 8.17 (m, 1H, NH), 8.40 (d, 1H, J=5.5 Hz, Ph-H), 8.53 (s, 1H, Ph-H), 9.96 (s, 1H, NH). DE MALDI-TOF MS: {M+H}$^+$=399.8 ($C_{16}H_{13}N_3SClF_3$ requires 399.8).

(3,4-Difluoro-phenyl)-{4-(4-methyl-2-methylamino-thiazol-5-yl)-pyrimidin-2-yl}-amine {104}

Light-yellow solid. $^1$H-NMR (300 MHz, d$_6$-DMSO) δ 2.87 s, 3H, CH$_3$), 3.12 (s, 3H, CH$_3$), 6.97 (d, 1H, J=5.1 Hz, pyrimidinyl-H), 7.35 (m, 1H, Ph-H), 8.04 (d, 1H, Ph-H), 8.08 (d, 1H, Ph-H), 8.20 (m, 1H, NH), 8.37 (d, 1H, J=5.3, pyrimidinyl-H), 9.71 (s, 1H, NH). DE MALDI-TOF MS: {M+H}$^+$=333.8 ($C_{15}H_{13}N_5SF_2$ requires 333.4).

(2,4-Difluoro-phenyl)-{4-(4-methyl-2-methylamino-thiazol-5-yl)-pyrimidin-2-yl}-amine {105}

Light-yellow solid. $^1$H-NMR (300 MHz, d$_6$-DMSO) δ : 2.84 (s, 3H, CH$_3$), 3.10 (s, 3H, CH$_3$), 6.86 (d, 1H, J=5.5 Hz, pyrimidinyl-H), 7.06 (m, 1H, Ph-H), 7.29 (m, 1H, Ph-H), 7.67 (m, 1H, Ph-H), 8.04 (m, 1H, NH), 8.26 (d, 1H, J=5.3, pyrimidinyl-H), 8.92 (s, 1H, NH). DE MALDI-TOF MS: {M+H}$^+$=334.2 ($C_{15}H_{13}N_5SF_2$ requires 333.4).

(4-Methoxy-phenyl)-{4-(4-methyl-2-methylamino-thiazol-5-yl)-pyrimidin-2-yl}-amine {109}

Green-yellow solid. $^1$H-NMR (300 MHz, d$_6$-DMSO) δ 2.87 (s, 3H, CH$_3$), 3.35 (s, 3H, CH$_3$), 3.74 (s, 3H, CH$_3$), 6.85 (m, 1H, pyrimidinyl-H), 6.86 (m, 2H, Ph-H), 7.66 (m, 2H, Ph-H), 8.02 (m, 1H, NHCH$_3$), 8.29 (d, 1H, J=5.4 Hz, pyrimidinyl-H), 9.25 (s, 1H, NH). DE MALDI-TOF MS: {M+H}$^+$=327.8 ($C_{16}H_{17}N_5OS$ requires 327.4).

2-Chloro-4-{4-(2,4-dimethyl-thiazol-5-yl)-pyrimidin-2-ylamino}-benzoic acid methyl ester {101}

Yellow crystals. $^1$H-NMR (30 MHz, d$_6$-DMSO) δ 2.88 (s, 3H, CH$_3$), 3.10 (s, 3H, CH$_3$), 3.82 (s, 3H, CH$_3$), 7.05 (d, 1H, J=5.5, pyrimidinyl-H), 7.73 (d, 1H, J=8.8 Hz, Ph-H), 7.85 (d, 1H, J=8.7 Hz, Ph-H), 8.20 (m, 1H, NHCH$_3$), 8.27 (s, 1H, Ph-H), 8.43 (d, 1H, J=5.6 Hz, pyrimidinyl-H). DE MALDI-TOF MS: {M+H}$^+$=388.8 ($C_{17}H_{16}N_5O_2SCl$ requires 389.9).

Example 11

3-Dimethylamino-1-(4-methyl-2-pyridin-3-yl-thiazol-5-yl)-propenone

A mixture of 5-chloro-pentadione (5.12 g, 38 mmol) and thionicotinamide (5.25 g, 38 mmol) in MeOH (10 mL) was treated with pyridine (3 mL). The reaction mixture was heated at 70–75° C. for 5 h. The solvent was evaporated. The resulting solid was filtered and washed with EtOAc/MeOH to afford 4.33 g 5-acetyl-4-methyl-2-(3-pyridyl)-thiazol as a yellow solid, which was subjected to the next reaction without further purification. A mixture of this material (2.0 g) and N,N-dimethylformamide dimethyl acetal (4 mL) was heated at 80° C. for 22 h. The reaction mixture was concentrated and then triturated with EtOAc/PE. The precipitates were collected and washed with EtOAc/PE to afford the title compound (2.05 g, 75%) as a grey solid. $^1$H-NMR (300 MHz, CDCl$_3$) δ 2.80 (s, 6H, CH$_3$), 3.50 (s, 3H, CH$_3$), 5.47 (d, 1H, J=12.1 Hz, CH), 7.39 (m, 1H, Ar-H), 7.78 (d, 1H, J=12.1 Hz, CH), 8.28 (m, 1H, Ar-H), 8.66 (m, 1H, Ar-H), 9.16 (s, 1H, Ar-H).

Example 12

{4-4-Methyl-2-pyridin-3-yl-thiazol-5-yl)-pyrimidin-2-yl}-3-nitro-phenyl)-amine {71}

To a mixture of 3-dimethylamino-1-(4-methyl-2-pyridin-3-yl-thiazol-5-yl)-propenone (1 mmol, 0.27 g) and N-(3- nitro-phenyl)-guanidine nitrate (1 mmol, 0.24 g) in 2-methoxyethanol (5 mL) was added NaOH (40 mg). The reaction mixture was heated at 120° C. under $N_2$ for 20 h. The solvent was evaporated to dryness and the residue was purified by flash chromatography, using EtOAc/PE (2:1, v/v) to elute the product, which was recrystallized from MeOH to afford the title compound (154 mg) as light-yellow crystals. $^1$H-NMR (300 MHz, $d_6$-DMSO) δ 2.82 (s, 3H, $CH_3$), 7.24 (d, 1H, J=5.2 Hz, pyrimidinyl-H), 7.53 (m, 2H, Ar-H), 7.82 (m, 1H, Ph-H), 8.00 (m, 1H, Ar-H), 8.09 (s, 1H, Ar-H), 8.35 (m, 1H, Ar-H), 8.61 (d, 1H, J=5.2 Hz, Py-H), 8.68 (m, 1H, Ar-H), 10.23 (s, 1 H, NH).

The following compound was prepared in a manner analogous to that described above:

(4-Fluoro-phenyl)-{4-(4-methyl-2-pyridin-3-yl-thiazol-5-yl)-pyrimidin-2-yl}-amine {67}

$^1$H-NMR (300 MHz, $d_6$-DMSO) δ 2.78 (s, 3H, $CH_3$), 7.22 (m, 2H, pyrimidinyl-H, Ar-H), 7.59 (m, 1H, Ar-H), 7.82 (m, 2H, Ar-H), 8.38 (m, 1H, Ar-H), 8.60 (d, 1H, J=5.2 Hz, pyrimidinyl-H), 8.72 (m, 1H, Ar-H), 9.21 (s, 1H, Ar-H), 9.83 (s, 1H, NH).

Example 13

1-(2,4-Dimethyl-thiazol-5-yl)-3-(4-trifluoromethyl-phenyl)-propenone To an ice-cold solution of NaOH (2.2 g) in $H_2O$ (10 mL) 2,4-dimethyl-5-acetylthiazol (43 mmol, 6.6 g) was added. After 5 min stirring this was treated with trifluoro-p-tolualdehyde (43 mmol, 7.49 g). The reaction mixture was warmed to r.t. and stirred for 2 h. It was diluted with $CH_2Cl_2$, washed with $HCl/H_2O$, brine and was dried over $MgSO_4$. The solvent was evaporated to afford the title compound (4.86 g).

Example 14

4-{4-(2,4-Dimethyl-thiazol-5-yl)-6-(4-trifluoromethyl-phenyl)-pyrimidin-2-ylamino}-2-nitro-phenol {66}

A mixture of 1-(2,4-dimethyl-thiazol-5-yl)-3-(4-trifluoromethyl-phenyl)-propenone (1 mmol, 0.31 g) and N-(4-hydroxy-3-nitro-phenyl)-guanidine nitrate (1.5 mmol, 0.39 g) in 2-methoxyethanol (5 mL) was added NaOH (40 mg). The reaction mixture was heated at 120° C. under $N_2$ for 20 h. The solvent was evaporated to dryness and the residue was purified by flash chromatography, using EtOAc/PE (2:1, v/v) to elute the product, which was recrystallized from MeOH/EtOAc to afford the title compound (178 mg) as orange crystals. $^1$H-NMR (300 MHz, $CDCl_3$) δ 2.75 (s, 3H, $CH_3$), 2.79 (s, 3H, $CH_3$), 7.18 (m, 1H, Ar-H), 7.44 (s, 1H, pyrimidinyl-H), 7.61 (m, 1H, Ar-H), 7.81 (m, 2H, Ar-H), 8.22 (m, 2H, Ar-H), 8.98 (m, 1H, Ar-H).

The following compounds were prepared in a manner analogous to that described above:

{4-(2,4-Dimethyl-thiazol-5-yl)-6-(4-trifluoromethyl-phenyl)-pyrimidin-2-yl}-(4-fluoro-phenyl)-amine {64}

$^1$H-NMR (300 MHz, $CDCl_3$) δ 2.73 (s, 3H, $CH_3$), 2.78 (s, 3H, $CH_3$), 7.05 (m, 2H, Ar-H), 7.36 (s, 1H, pyrimidinyl-H), 7.78 (m, 4H, Ar-H), 8.22 (m, 2H, Ar-H), 8.67 (sbr, 1H, NH).

(4-Chloro-phenyl)-{4-(2,4-dimethyl-thiazol-5-yl)-6-(4-trifluoromethyl-phenyl)-pyrimidin-2-yl}-amine {65}

$^1$H-NMR (300 MHz, $CDCl_3$) δ 2.73 (s, 3H, $CH_3$), 2.79 (s, 3H, $CH_3$), 7.29 (m, 2H, Ar-H), 7.39 (s, 1H, pyrimidinyl-H), 7.80 (m, 4H, Ar-H), 8.22 (m, 2H, Ar-H), 8.96 (sbr, 1H, NH).

{4-(2,4-Dimethyl-thiazol-5-yl)-6-phenyl-pyrimidin-2-yl}-(3-nitro-phenyl)-amine {57}

$^1$H-NMR (300 MHz, $d_6$-DMSO) δ 2.68(s, 3H, $CH_3$), 2.75 (s, 3H, $CH_3$), 7.61 (m, 4H, Ar-H), 7.84 (m, 1H, Ar-H), 8.08 (m, 1H, Ar-H), 8.27 (m, 2H, Ar-H), 9.15 (s, 1H, Ar-H), 10.3 (s, 1H, NH).

4-{6-(2,4-Dimethyl-thiazol-5-yl)-2-(4-fluoro-phenylamino)-pyrimidin-4-yl}-phenol {70}

$^1$H-NMR (300 MHz, $d_6$-DMSO) δ 2.67 (s, 3H, $CH_3$), 2.72 (s, 3H, $CH_3$), 6.93 (m, 2H, Ar-H), 7.18 (m, 2H, Ar-H), 7.42 (s, 1H, pyrimidinyl-H), 7.84 (m, 2H, Ar-H), 8.09 (m, 2H, Ar-H), 9.67 (s, 1H, NH or OH), 10.11 (s, 1H, NH or OH).

Example 15

{4-(2-Allylamino-4-methyl-thiazol-5-yl)-pyrimidin-2-yl}-(3-nitro-phenyl)-amine {91}

To a mixture of 1-(2-allylamino-4-methyl-thiazol-5-yl)-3-dimethylamino-propenone (1.0 mmol, 0.25 g) and N-(3-nitro-phenyl)-guanidine nitrate (1.5 mmol, 0.36 g) in 2-methoxyethanol (5 mL) was added NaOH (40 mg). The reaction mixture was heated at 110–120° C. under $N_2$ for 22 h. The solvent was evaporated to dryness and the residue was purified by flash chromatography, using EtOAc/PE (1:1, v/v) to elute the product as yellow solid. Recrystallisation from EtOAc/MeOH yielded the title compound as brown crystals. $^1$H-NMR (300 MHz, $d_6$-DMSO) δ 2.51 (s, 3H, $CH_3$), 3.92 (sbr, 2H, $CH_2$), 5.20 (m, 2H, $CH_2$), 5.91 (m, 1H, CH), 7.02 (d, 1H, J=5.5 Hz, pyrimidinyl-H ), 7.57 (m, 2H, Ph-H), 7.80 (m, 1 H, Ph-H), 8.06 (m, 1H, Ph-H), 8.43 (d, 1H, J=5.5 Hz, pyrimidinyl-H), 8.94 (s, 1H, Ph-H), 10.04 (s, 1H, NH).

The following compound was prepared in a manner analogous to that described above:

{4-(2-Allylamino-4-methyl-thiazol-5-yl)-pyrimidin-2-yl}-(4-fluoro-phenyl)-amine {82}

$^1$H-NMR (300 MHz, $d_6$-DMSO) δ 2.51 (s, 3H, $CH_3$), 3.92 (sbr, 2H, $CH_2$), 5.24 (m, 2H, $CH_2$), 5.91 (m, 1H, CH), 6.90 (d, 1H, J=5.5 Hz, pyrimidinyl-H), 7.11 (m, 2H, Ph-H), 7.76 (m, 2H, Ph-H), 8.33 (d, 1H, J=5.5 Hz, pyrimidinyl-H), 9.49 (s, 1H, NH). DE MALDI-TOF MS: {M+H}$^+$=341.4 ($C_{17}H_{16}FN_5S$ requires 341.4).

Example 16

{4-(2-Ethylamino-4-methyl-thiazol-5-yl)-pyrimidin-2-yl}-(4-fluoro-phenyl)-amine {75}

A mixture of 3-dimethylamino-1-(2-ethylamino-4-methyl-thiazol-5-yl}-propenone (1 mmol, 0.24 g) and NaOH (40 mg) in 2-methoxyethanol (5 mL) was treated with of N-4-fluoro-phenyl)-guanidine nitrate (0.36 g, 1.5 mmol). The reaction mixture was heated at 110–120° C. under $N_2$ for 20 h. After concentration, the residue was filtered and washed with MeOH. Recrystallisation from EtOAc/MeOH afforded the title compounds (291 mg) as a yellow solid. $^1$H-NMR (300 MHz, $d_6$-DMSO) δ 1.17 (m, 3H, $CH_3$), 2.51 (s, 3H, $CH_3$), 3.26 (m, 2H, $CH_2$), 6.89 (d, 1H, J=5.5 Hz, pyrimidinyl-H), 7.11 (m, 2H, Ph-H), 7.77 (m, 2H, Ph-H), 8.33 (d, 1H, J=5.5 Hz, pyrimidinyl-H). DE MALDI-TOF MS: {M+H}$^+$=331.2 ($C_{16}H_{16}FN_5S$ requires 329.4).

Example 17

4-{4-{2-(4-Nitro-phenylamino)-thiazol-5-yl}-pyrimidin-2-ylamino}-phenol {111}

A mixture of 3-dimethylamino-1-2-(4-nitro-phenylamino)-thiazol-5-yl}-propenone (1 mmol, 0.32 g) and NaOH (50 mg) in 2-methoxyethanol (5 mL) was treated with N-(4-hydroxy-phenyl)-guanidine nitrate (0.32 g, 1.5 mmol). The reaction mixture was heated at 110–120° C. under $N_2$ for 6 h. After concentration, the residue was filtered and washed with MeOH. Recrystallisation from MeOH afforded the title compound as an orange solid. $^1$H-NMR (300 MHz, $d_6$-DMSO) δ 6.67 (m, 2H, Ph-H), 6.93 (d, 1H, J =5.4 Hz, pyrimidinyl-H), 7.48 (m, 2H, Ph-H), 7.86 (m, 2H, Ph-H), 8.26 (m, 2H, Ph-H), 8.36 (d, 1H, J=5.3 Hz, pyrimidinyl-H). DE MALDI-TOF MS: $\{M+H\}^+$=406.82 ($C_{19}H_{14}N_6O_3S$ requires 406.42).

Example 18

N-{3-{4-(2,4-Dimethyl-thiazol-5-yl)-pyrimidin-2-ylamino}-phenyl}-guanidine {115}

To a mixture of {4-(2,4-dimethyl-thiazol-5-yl)-pyrimidin-2-yl}-(3-nitro-phenyl)-amine (3.97 mmol, 1.3 g) in 2-methoxyethanol (15 mL) was added AcOH (1 mL). The reaction mixture was stirred under $N_2$ for 10 min. Palladium catalyst (660 mg; 10% on activated carbon) was the added and the reaction mixture was allowed to stir under $H_2$ for 18 h. The reaction mixture was passed through Celite 521 and the precipitates were washed several times with MeOH. The filtrate was concentrated and recrystallised from MeOH/EtOAc to afford grey crystals of N-{4-(2,4-dimethyl-thiazol-5-yl)-pyrimidin-2-yl}-benzene-1,3-diamine. An aliquot of this material (500 mg) in 2-methoxyethanol was cooled on an ice bath and was treated with HCl (conc. 1 mL). Cyanamide (50% aq soln., 4 mL) was added dropwise. After completion of the addition the reaction mixture was warmed to r.t. and heated at reflux for 20 h. The reaction mixture was concentrated. The residue was diluted with EtOAc and washed with water and brine. The organic phase was evaporated and purified by chromatography, using EtOAc/MeOH (3:1, v/v) to elute the title compound. DE MALDI-TOF MS: $\{M+H\}^+$=339.16 ($C_{16}H_{17}N_7S$ requires 339.42).

Example 19

{3-{4-(2,4-Dimethyl-thiazol-5-yl)-pyrimidin-2-ylamino}-phenyl}-methanol {116}

A mixture of 3-dimethylamino-1-(2,4-dimethyl-thiazol-5-yl)-propenone (10 mmol, 2.1 g) in 2-methoxyethanol was treated with N-(4-hydroxymethyl-phenyl)-guanidine hydrochloride (1.65 g) in the presence of NaOH (400 mg). The reaction mixture was allowed to reflux for 20 h. After concentration, the precipitates were filtered and washed with EtOAc/MeOH several times. Recrystallisation from MeOH/EtOAc afforded the title compound (2.17 g, 70%). $^1$H-NMR (300 MHz, $d_6$-DMSO) δ 3.00 (s, 3H, $CH_3$), 3.02 (s, 3H, $CH_3$), 4.86 (s, 2H, $CH_2$), 7.30 (m, 1H, Ph-H), 7.44 (d, 1H, J=6.1 Hz, pyrimidinyl-H), 7.61 (m, 1H, Ph-H), 8.01 (m, 1H, Ph-H), 8.13 (s, 1H, Ph-H), 8.88 (d, 1H, J=6.1 Hz, pyrimidinyl-H).

Example 20

{3-(2-Diethylamino-ethoxymethyl)-phenyl}-{4-(2,4-dimethyl-thiazol-5-yl)-pyrimidin-2-yl}-amine {118}

A solution of {3-{4-(2,4-dimethyl-thaizol-5-yl)-pyrimidin-2-ylamino}-phenyl}-methanol (1 mmol, 0.34 g) in dry DMF was treated with NaH (1 mmol, 24 mg). After stirring at r.t. for 20 min, (2-chloro-ethyl)-diethyl-amine hydrochloride (0.17 g, 1 mmol) and pyridine (0.4 mL) were added. After stirring at r.t. for 21 h the reaction mixture was cooled on an ice bath and water was added dropwise. The reaction mixture was neutralised by addition of aq HCl soln. and extracted with EtOAc. The organic phases were combined, washed with brine and dried over $MgSO_4$. The solvent was evaporated to dryness. The residue was purified by chromatography, using EtOAc/MeOH (1:1, v/v) to elute the title compound as light-yellow solid, which was recrystallised from EtOAc/PE. $^1$H-NMR ($CDCl_3$) δ 1.00 (t, 6H, J=7.0 Hz, $CH_3$), 2.59 (m, 2H, $CH_2$), 2.62 (s, 3H, $CH_3$), 2.66 (s, 3H, $CH_3$), 2.78 (m, 2H, $CH_2$), 4.12 (m, 2H, $CH_2$), 4.72 (s, 2H, $CH_2$), 6.76 (d, 1H, J=5.5 Hz, pyrimidinyl-H), 7.24 (m, 3H, Ph-H), 7.36 (m, 1H, Ph-H), 7.40 (m, 2H, Ph-H), 8.28 (d, 1H, J=5.5 Hz, pyrimidinyl-H). DE MALDI-TOF MS: $\{M+H\}^+$=416.15 ($C_{22}H_{29}N_5SO$ requires 411.56).

Example 21

{4-(2,4-Dimethyl-thiazol-5-yl)-pyrimidin-2-yl}-(4-pyridin-4-ylmethyl-phenyl)-amine {117}

A solution of 4-(4-nitro-benzyl)-pyridine (24 mmol, 5.1 g) in MeOH (15 mL) was hydrogenated in the presence of 500 mg palladium (10% on activated carbon). After stirring at r.t. for 20 h the reaction mixture was filtered through Celite 521. The filter aid was washed with MeOH several times. The filtrate was evaporated to dryness to afford 4-pyridin-4-ylmethyl-phenylamine (1.84 g) as a grey solid. Anal. RP-HPLC indicated a single product. A solution of this product in MeOH (15 mL) was cooled on an ice bath and was treated first with HCl (conc. 1.75 mL) followed by addition of cyanamide (50% aq soln.; 5 mL). The reaction mixture was heated at reflux for 18 h. The solvent was evaporated and the residue was washed with EtOAc/MeOH (2:1, v/v) to afford N-(4-pyridin-4-ylmethyl-phenyl)-guanidine hydrochloride (2.25 g) as a white solid.

A mixture of 3-dimethylamino-1-(2,4-dimethyl-thiazol-5-yl)-propenone (1 mmol, 0.21 g) and N-(4-pyridin-4-ylmethyl-phenyl)-guanidine hydrochloride (2 mmol, 0.40 mg) in 2-methoxyethanol was treated with NaOH (40 mg). The reaction mixture was allowed to heat at reflux for 2 d. The solvent was evaporated and the residue was crystallised from EtOAc/MeOH to afford the title compound as an orange solid. $^1$H-NMR (300 MHz, $d_6$-DMSO) δ 3.00 (s, 3H, $CH_3$), 3.02 (s, 3H, $CH_3$), 4.29 (s, 2H, $CH_2$), 7.44 (d, 1H, J=5.5 Hz, pyrimidinyl-H), 7.56 (m, 2H, Ph-H), 7.61 (m, 2H, Ar-H), 8.09 (m, 2H, Ph-H), 8.82 (m, 2H, Ar-H), 8.87 (d, 1H, J=5.5 Hz, pyrimidinyl-H). DE MALDI-TOF MS: $\{M+H\}^+$=377.52 ($C_{21}H_{19}N_5S$ requires 373.48).

Example 22

{4-{4-(2,4-Dimethyl-thiazol-5-yl)-pyrimidin-2-ylamino}-phenyl}-trimethyl-ammonium {120}

A mixture of 3-dimethylamino-1-(2,4-dimethyl-thiazol-5-yl)-propenone (0.95 mmol, 0.19 g) and N-(4-dimethylamino-phenyl)-guanidine (2 mmol) in 2-methoxyethanol (5 mL) was added NaOH (40 mg). The reaction mixture was heated at 120° C. for 18 h. The solvent was evaporated and the residue was purified by chromatography, using EtOAc/PE to afford N,N-dimethyl-N'-{4-(2,4-dimethyl-thiazol-5-yl)-pyrimidin-2-yl}-benzene-1,4-diamine {119} (74 mg) as a reddish-brown solid. $^1$H-NMR (300 MHz, $d_6$-DMSO) δ 2.62 (s, 3H, $CH_3$), 2.65 (s, 3H, $CH_3$), 2.86 (s, 6H, $CH_3$), 6.73 (m, 2H, Ph-H), 6.97 (d, 1H, J=5.1 Hz, pyrimidinyl-H), 7.56 (m, 2H, Ph-I), 8.44

(d, 1H, J=5.0 Hz, pyrimidinyl-H), 9.33 (s, 1H, NH). DE MALDI-TOF MS: {M+H}$^+$=329.51 (C$_{17}$H$_{19}$N$_5$S requires 325.43).

To the above compound (0.13 mmol, 42 mg) in dry acetone (6 mL) was added 12 □L iodomethane dropwise and the reaction mixture was heated at reflux for 18 h. The solvent was evaporated and the resulting oil was triturated with toluene (5 mL). The resulting precipitate was filtered, washed with EtOAc and dried under high vacuum overnight to afford the title compound (18 mg). $^1$H-NMR (300 MHz, d$_6$-DMSO) δ 2.63 (s, 3H, CH$_3$), 2.65 (s, 3H, CH$_3$), 3.56 (s, 9H, CH$_3$), 7.17 (d, 1H, J=5.4 Hz, pyrimidinyl-H), 7.88 (m, 2H, Ph-H), 7.96 (m, 2H, Ph-H), 8.57 (d, 1H, J=5.4 Hz, pyrimidinyl-H), 10.04 (s, 1H, NH). DE MALDI-TOF MS: {M+H}=343.39 (C$_{19}$H$_{25}$N$_5$S requires 340.47).

The biological activity of the compounds of the invention was demonstrated by measuring the CDK inhibition by virtue of an assay-based screen, and/or by a cytotoxicity assay using one or more cell lines.

Example 23
Kinase specificity of selected compound

Selected compounds from the above examples were investigated for their kinase selectivity. A panel of protein kinases, including the CDKs relevant to the present invention, as well as a representative number of functionally unrelated kinases, were used.

Assays for CDK4/Cyclin D1, CDK2/Cyclin E, CDIK1/Cyclin B kinase may be carried out by monitoring phosphorylation of GST-Rb in an appropriate system. Thus, GST-Rb phosphorylation, induced by CDK4/Cyclin D1, CDK2/Cyclin E or CDK1/Cyclin B is determined by incorporation of radio-labeled phosphate in GST-Rb(772-928) using radiolabelled ATP in 96-well format in vitro kinase assay. The phosphorylation reaction mixture (total volume 40 μl) consisted of 50 mM HEPES pH 7.4, 20 mM MgCl$_2$, 5 mM EGTA, 2 mM DTT, 20 mM β-glycerophosphate, 2 mM NaF, 1 mM Na$_3$VO$_4$, Protease Inhibitors Cocktail (Sigma, see above), BSA 0.5 mg/ml, 1 μg purified enzyme complex, 10 μl of GST-Rb-Sepharose beads, 100 μM ATP, 0.2 μCi $^{32}$P-ATP. The reaction is carried out for 30 min at 30° C. at constant shaking. At the end of this period 100 μl of 50 mM HEPES, pH 7.4 and 1 mM ATP is added to each well and the total volume transferred onto GFC filtered plate. The plate is washed 5 times with 200 μl of 50 mM HEPES, pH 7.4 and 1 mM ATP. To each well were added 50 μl scintillant liquid and the radioactivity of the samples is measured on Scintilation counter (Topcount, HP). The IC$_{50}$ values of different peptides were calculated using GraFit software.

Alternatively, CDK2/cyclin A kinase assays may be performed in 96-well plates using recombinant CDK2/cyclin A. Assay buffer consisted of 25 mM β-glycerophosphate, 20 mM MOPS, 5 mM EGTA, 1 mM DTT, 1 mM NaVO$_3$, pH 7.4, into which is added 2–4 μg of CDK2/cyclin A with substrate pRb(773–928). The reaction is initiated by addition of Mg/ATP mix (15 mM MgCl$_2$, 100 μM ATP with 30–50 kBq per well of {γ-$^{32}$P}-ATP) and mixtures incubated for 10–30 min, as required, at 30° C. Reactions were stopped on ice, followed by filtration through p81 filterplates (Whatman Polyfiltronics, Kent, UK). After washing 3 times with 75 mM orthophosphoric acid, plates were dried, scintillant added and incorporated radioactivity measured in a scintillation counter (TopCount, Packard Instruments, Pangbourne, Berks, UK).

PKCα kinase activity may be measured by the incorporation of radio-labeled phosphate in Histone 3, as described. The reaction mixture (total volume 65 μl) consist of 50 mM Tris-HCl, 1 mM Calcium acetate, 3 mM DTT, 0.03 mg/ml Phosphatidylserine, 2.4 μg/ml PMA, 0.04% NP40, 12 mM Mg/Cl, purified PKCα-100 ng, Histone 3, 0.2 mg/ml, 100 μM ATP, 0.2 μCi {γ-$^{32}$P}-ATP. The reaction is carried over 15 min at 37° C. in microplate shaker and is stopped by adding 10 μl 75 mM orthophosphoric acid and placing the plate on ice. 50 μl of the reaction mixture is transferred onto P81 filterplate and after washing off the free radioactive phosphate (3 times with 200 μl 75 mM orthophosphoric acid per well) 50 μl of scintillation liquid (Microscint 40) were added to each well and the radioactivity is measured on Scintillation counter (Topcount, HP).

For use in said assays CDK2 and/or PKC may be obtained from available sources or produced by recombinant methods as described. His-tagged CDK2/Cyclin E and CDK1/Cyclin B may be co-expressed and PKCα singularly expressed in Sf 9 insect cells infected with the appropriate baculovirus constructs. The cells are harvested two days after infection by low speed centrifugation and the proteins purified from the insect cell pellets by Metal-chelate chromatography. Briefly, the insect cell pellet is lysed in Buffer A (10 mM Tris-HCl, pH 8.0, 150 mM NaCl, 0.02% NP40 and 5 mM β-marcaptoethanol, 1 mM NaF. 1 mM Na$_3$VO$_4$ and Protease Inhibitors Coctail (Sigma) containing AEBSF, pepstatin A, E 64, bestatin, leupeptin) by sonication. The soluble fraction is cleared by centrifugation and loaded onto Ni-NTA-Agarose (Quiagen). Non bound proteins were washed off with 300 mM NaCl, 5–15 mM Imidazole in Buffer A and the bound proteins eluted with 250 mM Imidazole in Buffer A. The purified proteins are extensively dialyzed against Storage buffer (20 mM HEPES pH 7.4, 50 mM NaCl, 2 mM DTT, 1 mM EDTA, 1 mM EGTA, 0.02% NP40, 10% v/v Glycerol) aliquoted and stored at −70° C. PKC-α-6×His may be purified the same way but using different buffers—50 mM NaH2PO4, pH 8.0 and 0.05% Triton X-100 instead of Tris and NP40 respectively.

The results in the Table 1 below show that the compounds in question exhibit a high degree of selectivity for inhibition of CDKs.

TABLE 1

| | Kinase assay IC$_{50}$ (μM) | | | | | | |
|---|---|---|---|---|---|---|---|
| Compound | CDK1/ cyclin B | CDK2/cyclin E | CDK4/cyclin D1 | ERK-2 | PKCa | SAPK2a | S6 |
| 2-[N-(4-Chlorophenyl)]-4-(2,4-dimethylthiazol-5-yl)-pyrimidineamine | >20 | 9 ± 12 | 0.5 ± 0.5 | >20 | >20 | >20 | >20 |
| 2-N-[(3-Nitrophenyl)-4-(2,4-dimethylthiazol-5-yl)-pyrimidineamine | 0.1 | 0.17 ± 0.06 | 0.19 ± 0.14 | >20 | >20 | >20 | >20 |

TABLE 1-continued

| Compound | Kinase assay IC$_{50}$ ($\mu$M) | | | | | | |
|---|---|---|---|---|---|---|---|
| | CDK1/cyclin B | CDK2/cyclin E | CDK4/cyclin D1 | ERK-2 | PKCa | SAPK2a | S6 |
| 2-[N-(4-Fluorophenyl)]-4-(2,4-dimethylthiazol-5-yl)-pyrimidineamine | 0.2 | 0.019 ± 0.004 | 0.47 ± 0.14 | 2.5 | >20 | >20 | 1 |

Further results for CDK2/cyclin E inhibition are shown below in Table 2.

TABLE 2

| Compound | CDK2/cyclin E | Compound | CDK2/cyclin E |
|---|---|---|---|
| 6 | 5 ± 9 | 62 | 0.06 ± 0.03 |
| 7 | 0.1 | 63 | 0.05 |
| 9 | 4.7 | 72 | 0.9 |
| 12 | 0.23 ± 0.07 | 73 | 0.2 |
| 13 | 8 ± 3 | 74 | 0.1 |
| 20 | 2.5 ± 0.1 | 75 | 0.2 |
| 21 | 0.07 ± 0.08 | 76 | 0.8 |
| 22 | 0.02 | 82 | 0.2 | of different human tumour cell lines. Standard 72-h MTT (thiazolyl blue; 3-{4,5-dimethylthiazol-2-yl}-2,5-diphenyltetrazolium bromide) assays were performed (Haselsberger, K.; Peterson, D. C.; Thomas, D. G.; Darling, J. L. Anti Cancer Drugs 1996, 7, 331-8; Loveland, B. E.; Johns, T. G.; Mackay, I. R.; Vaillant, F.; Wang, Z. X.; Hertzog, P. J. Biochemistry International 1992, 27, 501–10). Human tumour cell lines were obtained from the ATCC (American Type Culture Collection, 10801 University Boulevard, Manessas, Va. 20110-2209, USA).

The results in Table 3 below illustrate the anti-proliferative effect of compounds described in this application.

TABLE 3

| Compound | 72-h Cytotoxicity IC$_{50}$ ($\mu$M) | | | | | |
|---|---|---|---|---|---|---|
| | A549 | Saos-2 | MCF-7 | AGS | DU145 | HeLa |
| 2-N-[(3-Nitrophenyl)-4-(2,4-dimethylthiazol-5-yl)-pyrimidineamine | 1.5 ± 0.3 | 1.4 ± 0.3 | 1.7 ± 0.1 | 1.0 ± 0.2 | 1.0 ± 0.1 | 1.2 ± 0.2 |
| 2-[N-(4-Fluorophenyl)]-4-(2,4-dimethylthiazol-5-yl)-pyrimidineamine | 5.4 ± 0.4 | 8.5 ± 1.6 | 9.9 ± 0.4 | 4.2 ± 0.3 | 4.3 ± 0.2 | 3.2 ± 0.8 |

Additional data for cytotoxicity assay using the A549 cell line is shown below in Table 4.

TABLE 2-continued

| Compound | CDK2/cyclin E | Compound | CDK2/cyclin E |
|---|---|---|---|
| 23 | 1.7 | 83 | 0.2 |
| 28 | 0.94 ± 0.54 | 84 | 0.2 |
| 30 | 0.94 ± 0.49 | 85 | 0.09 |
| 31 | 0.2 | 86 | 0.13 |
| 33 | 0.2 | 87 | 0.08 |
| 35 | 0.2 ± 0.1 | 88 | 0.2 |
| 36 | 0.5 ± 0.2 | 89 | 1.2 |
| 37 | 6.4 ± 0.1 | 90 | 0.2 |
| 38 | 0.4 ± 0.3 | 94 | 0.6 |
| 39 | 0.22 ± 0.07 | 97 | 0.6 |
| 40 | 0.11 ± 0.05 | 98 | 1.1 |
| 41 | 0.06 | 102 | 0.6 |
| 45 | 0.21 ± 0.16 | 103 | 1.2 |
| 47 | 0.8 ± 0.4 | 105 | 2 |
| 48 | 0.03 | 106 | 10 |
| 49 | 0.02 | 107 | 3 |
| 50 | 0.3 | 108 | 0.8 |
| 51 | 0.75 | 114 | 1.4 |
| 52 | 0.06 | 116 | 0.7 |
| 53 | 0.7 ± 0.4 | 118 | 0.7 |
| 54 | 0.01 | 119 | 1.5 |
| 60 | 4 | | |

Example 24

Anti-proliferative effect of selected compounds

Selected compounds from the above examples were subjected to a standard cellular proliferation assay using a range

TABLE 4

| Compound | A549 | Compound | A549 |
|---|---|---|---|
| 2 | 41 ± 8 | 60 | 2.1 ± 0.3 |
| 3 | 5 ± 4 | 62 | 1.1 ± 0.2 |
| 4 | 16 ± 11 | 63 | 0.8 ± 0.2 |
| 7 | 2.8 | 65 | 55 ± 50 |
| 12 | 0.2 | 69 | 12 ± 5 |
| 15 | 6 | 70 | 3 ± 1 |
| 21 | 6.3 | 72 | 0.8 ± 0.5 |
| 22 | 20 ± 1 | 73 | 9 ± 4 |
| 24 | 5 | 74 | 18 ± 4 |
| 25 | 1.5 | 75 | 3.2 ± 0.4 |
| 26 | 3.3 | 76 | 3 ± 0.9 |
| 27 | 3.8 | 82 | 1.1 ± 0.3 |
| 28 | 3.5 | 83 | 0.6 ± 0.3 |
| 30 | 6.4 ± 0.05 | 84 | 0.26 ± 0.06 |
| 31 | 0.3 ± 0.05 | 85 | 0.4 |
| 32 | 23 | 86 | 8 ± 6 |
| 33 | 61 ± 55 | 87 | 1.7 ± 0.1 |
| 34 | 0.02 | 88 | 0.4 ± 01 |
| 35 | 4.2 | 89 | 18 ± 11 |
| 37 | 25 | 90 | 1.8 ± 0.8 |
| 38 | 4.5 ± 1.6 | 91 | 22.1 ± 0.2 |
| 39 | 0.3 | 92 | 4.4 ± 3 |
| 40 | 0.3 | 93 | 1.1 ± 1 |
| 41 | 0.02 | 94 | 0.5 ± 0.6 |
| 42 | 56 | 95 | 0.05 ± 0.03 |

TABLE 4-continued

| Compound | A549 | Compound | A549 |
|---|---|---|---|
| 45 | 3.3 ± 0.5 | 97 | 4.2 ± 0.4 |
| 47 | 1.8 ± 1.4 | 98 | 2.8 ± 2.1 |
| 48 | 6.7 ± 1.1 | 99 | 3.7 ± 2.7 |
| 49 | 2.2 ± 0.02 | 101 | 0.9 ± 0.2 |
| 50 | 8.8 ± 10 | 102 | 0.8 ± 0.2 |
| 51 | 0.3 ± 0.3 | 104 | 4.9 ± 2.5 |
| 52 | 0.8 ± 0.3 | 105 | 0.7 ± 0.9 |
| 53 | 12 ± 5 | 106 | 2.8 ± 0.5 |
| 57 | 5.2 ± 0.4 | 107 | 0.7 ± 0.2 |
| 59 | 22 ± 21 | | |

The following examples indicate the ability of some compounds to induce cell cycle arrest and apoptosis in human tumour cells.

Example 25

Induction of mitotic arrest and apoptosis in human tumour cells

Human osteosarcoma tumour cells (Saos-2) were treated with 1 μM of compound 28 for 48 h. The accumulation of mitotic cells and appearance of apoptotic cells was observed by phase-contract microscopy (FIG. 1). Compound 28-induced accumulation of mitotic cells was further quantified using mitotic index HitKit (Cellomix).

Example 26

Figures 1, 2, 3:
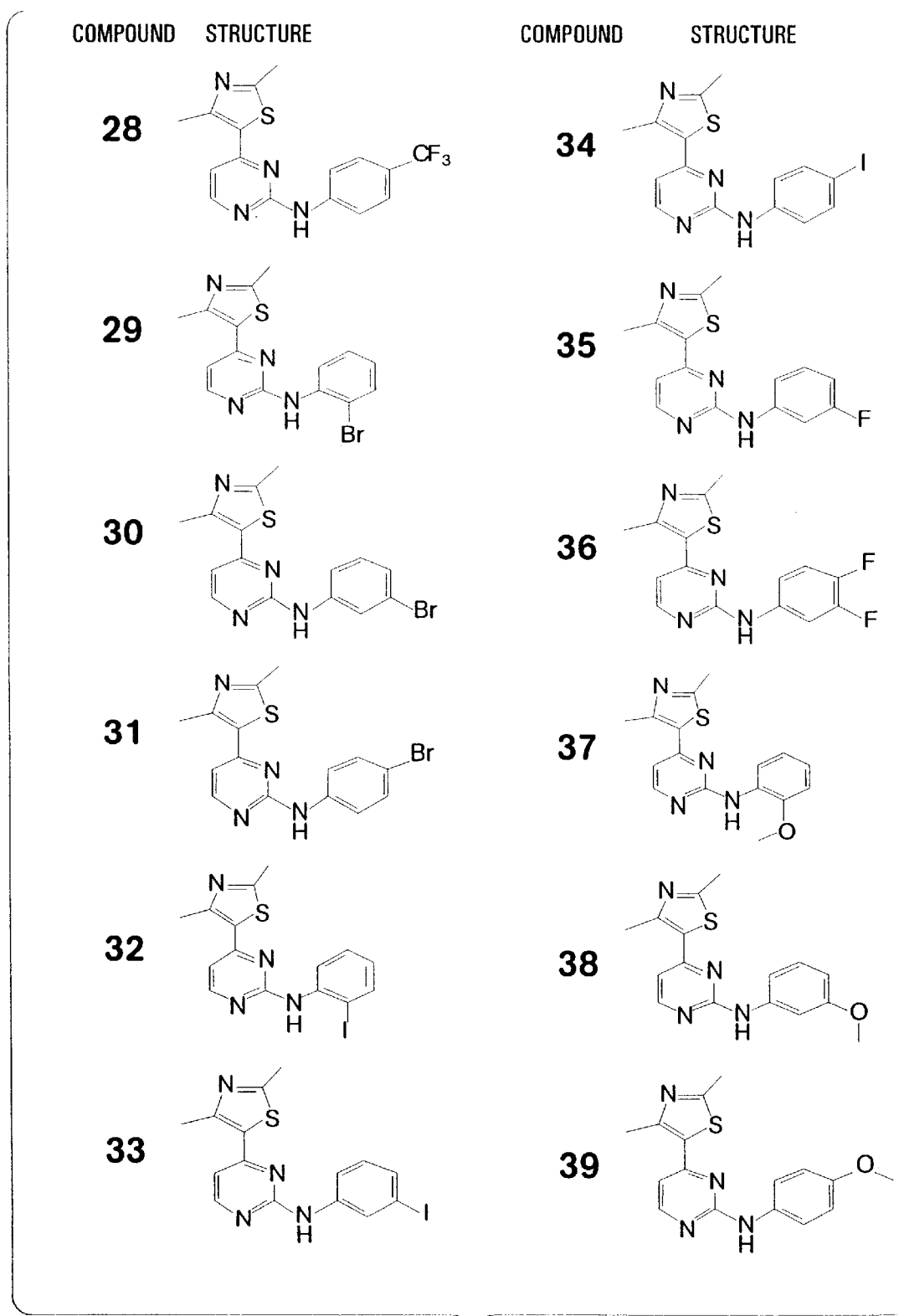
FIG. 3 shows the effect of compound 28 and Vinblastine on mitotic index.
Figures 1, 2, 3, 4:
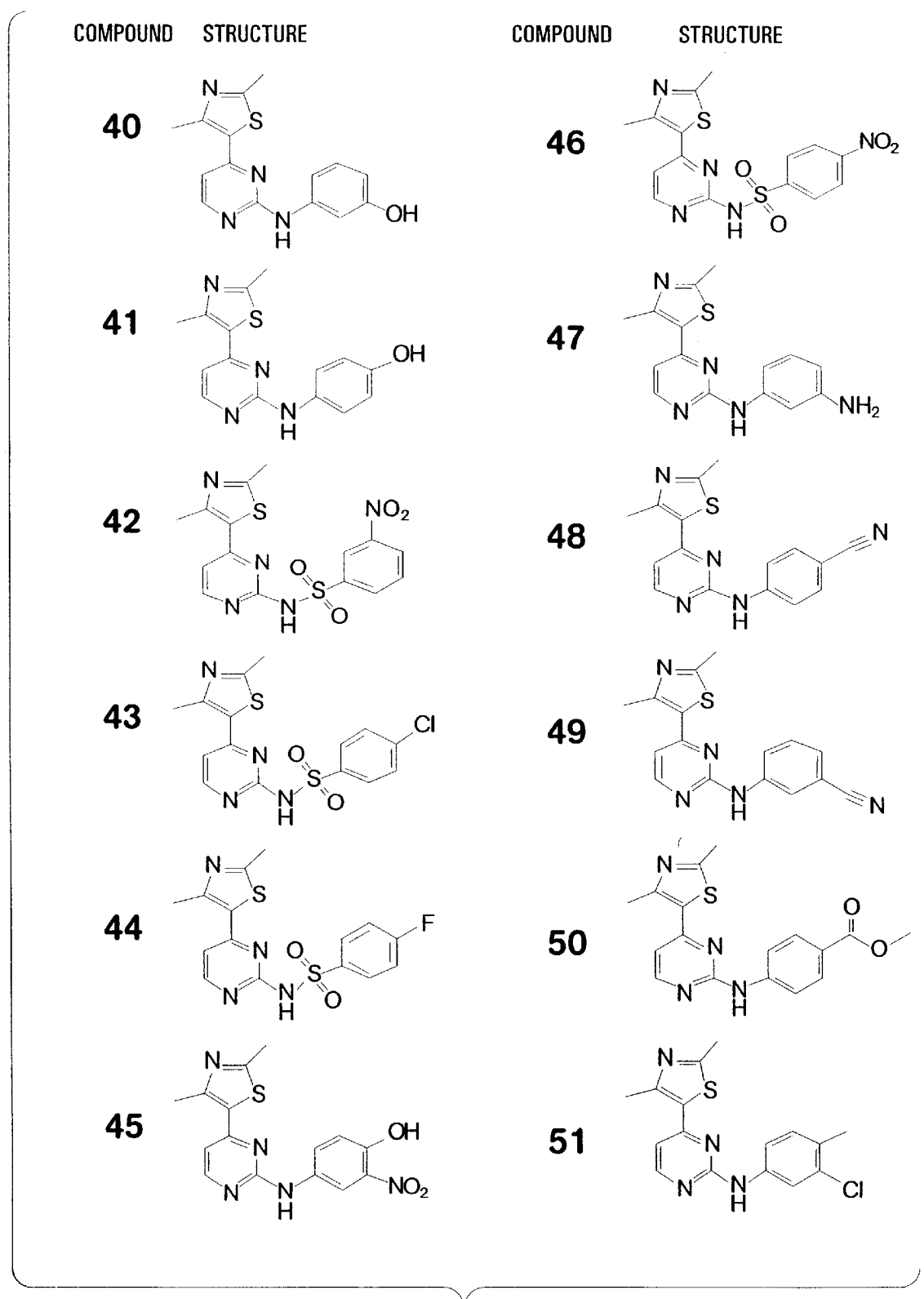
FIG. 4 shows representative images from compound 28 treated wells.

The effect of compound 28 on the mitotic index was studied using mitotic index HitKit (Cellomix). Vinblastine was used as control in the experiments. Plates of A549 cells were prepared as instructed in the mitotic index HitKit and the results obtained are shown in the FIGS. 3 and 4.

Example 27

Figures 1, 2, 3, 4, 5:
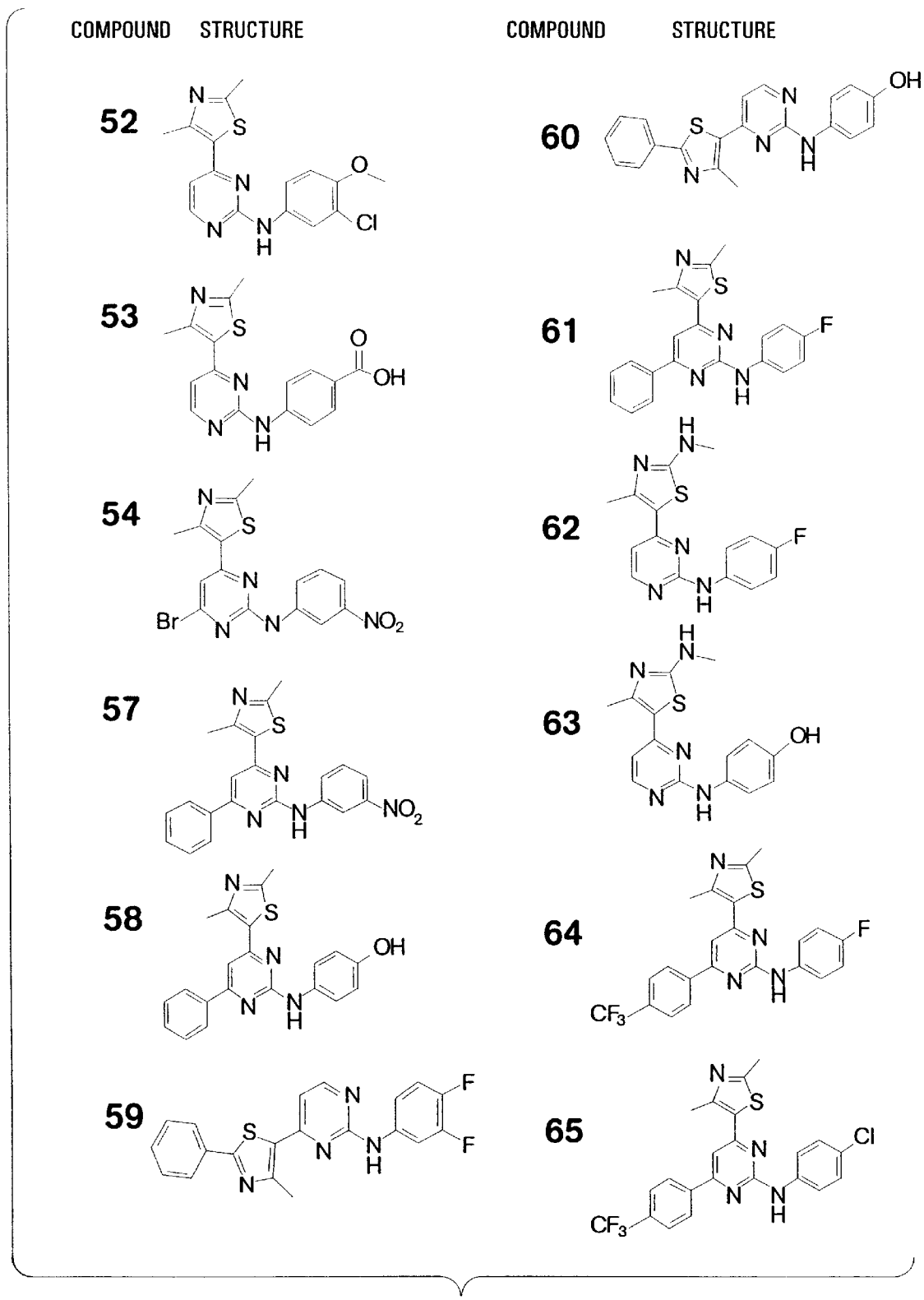
FIG. 5 shows the effect of compound 28 on the mitotic index (% cells against concentration of compound). (The curve on the left is Vinblastine.) (The curve on the right is CYC4068.)

FIG. 5 shows the effect of compound 28 on the mitotic index. The data shown in FIG. 5 demonstrate the effects of the compounds tested on the percentage of mitotic cells observed in 6 fields within each well. Compound 28 increased the percentage of mitotic cells from 2.6% (data not shown) in untreated wells to a maximum of 17% at a concentration of 4.4 μM. Above this concentration a decrease in the number of mitotic cells is observed which correlates with a decrease in the total number of cells. This indicates that toxicity is occurring and that cells are detaching from the bottom of the plate. Vinblastine increases the percentage of mitotic cells to a maximum of 31% at a concentration of 22 nM with toxicity being seen again above this concentration.

Example 28

Figures 1, 2, 3, 4, 5, 6:
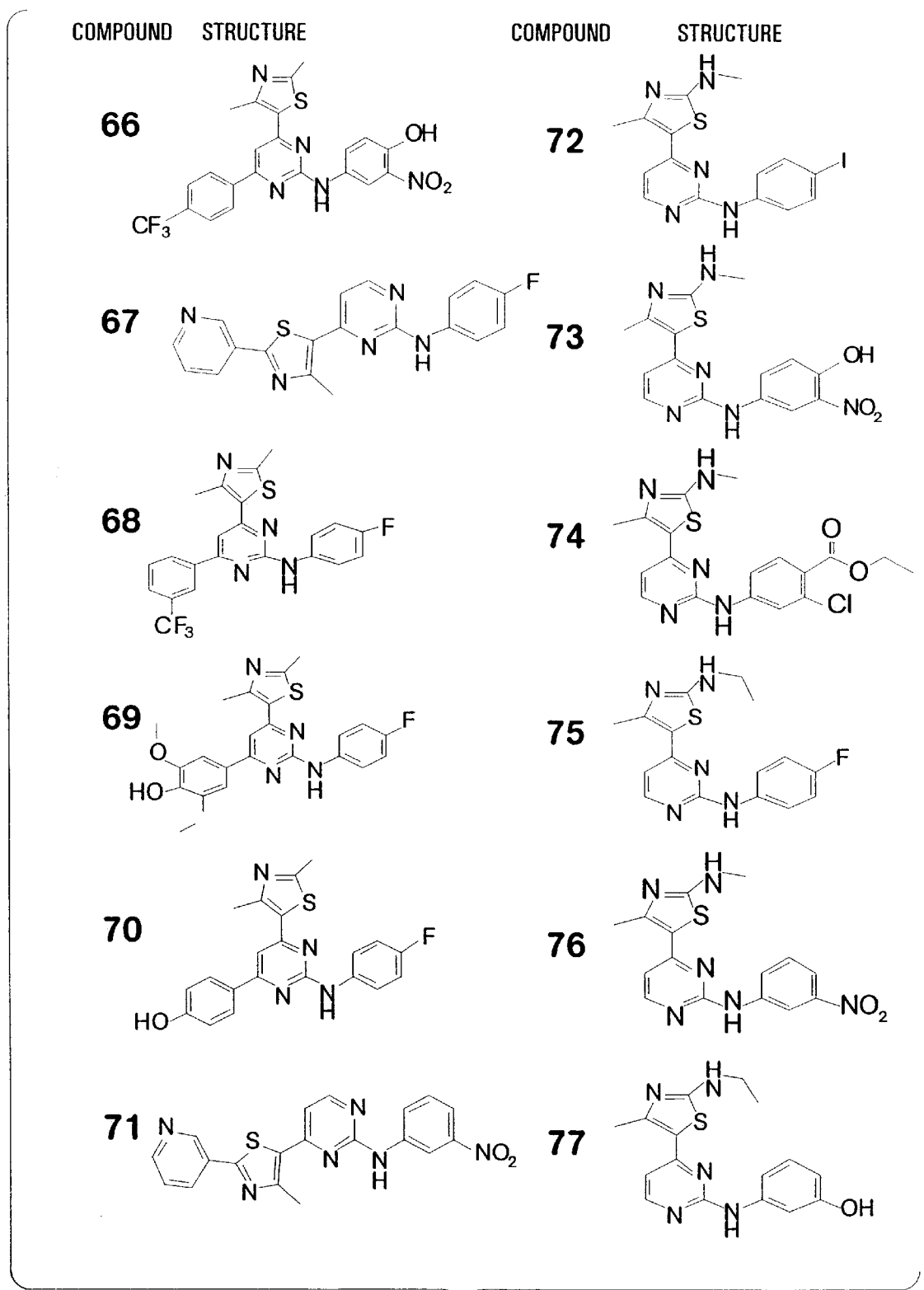
FIG. 6 shows the induction of programmed cell death by compound 28. In more detail.
Figures 1, 2, 3, 4, 5, 6, 7:
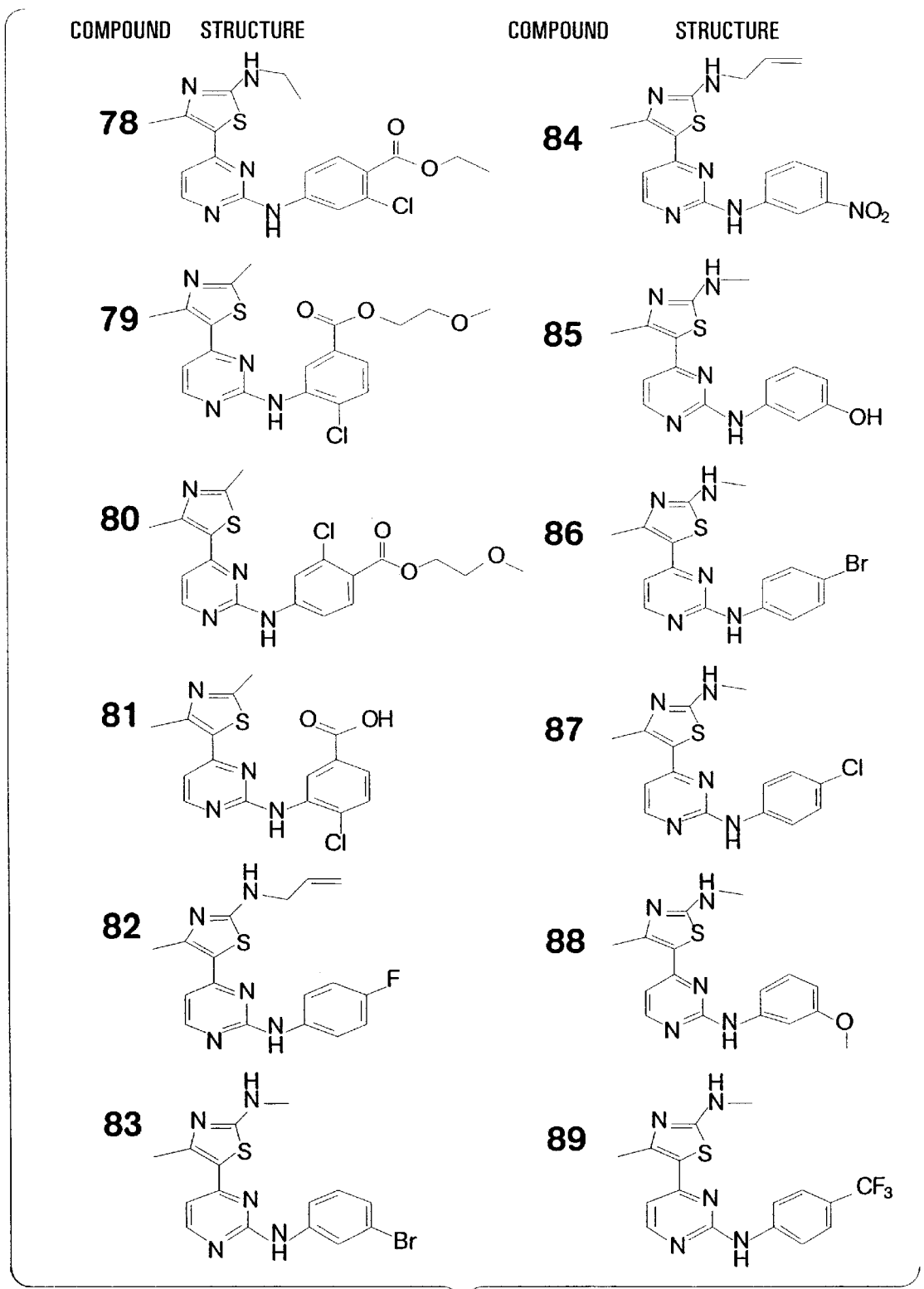
Figures 1, 2, 3, 4, 5, 6, 7, 8:
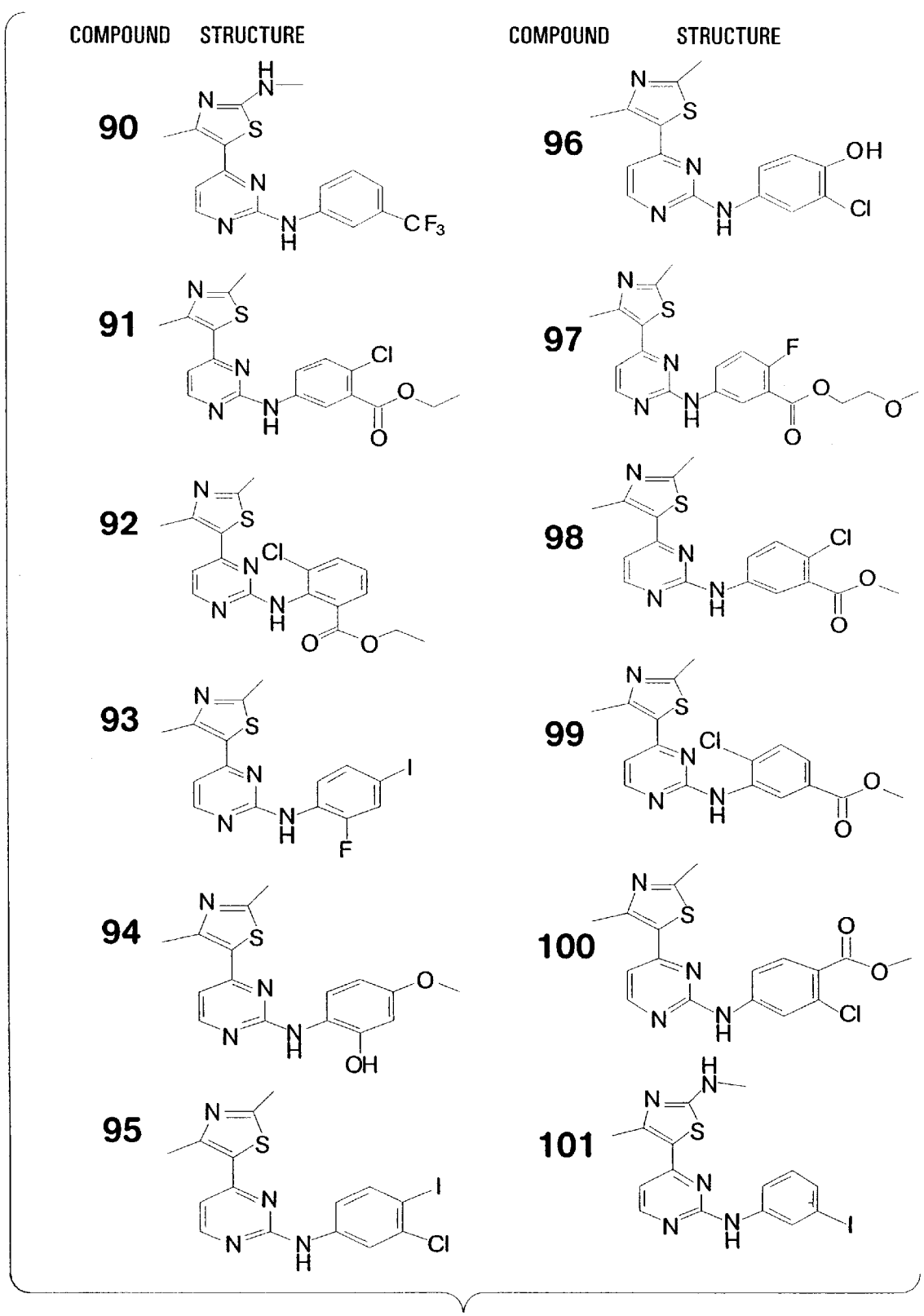
Figures 1, 2, 3, 4, 5, 6, 7, 8, 9:
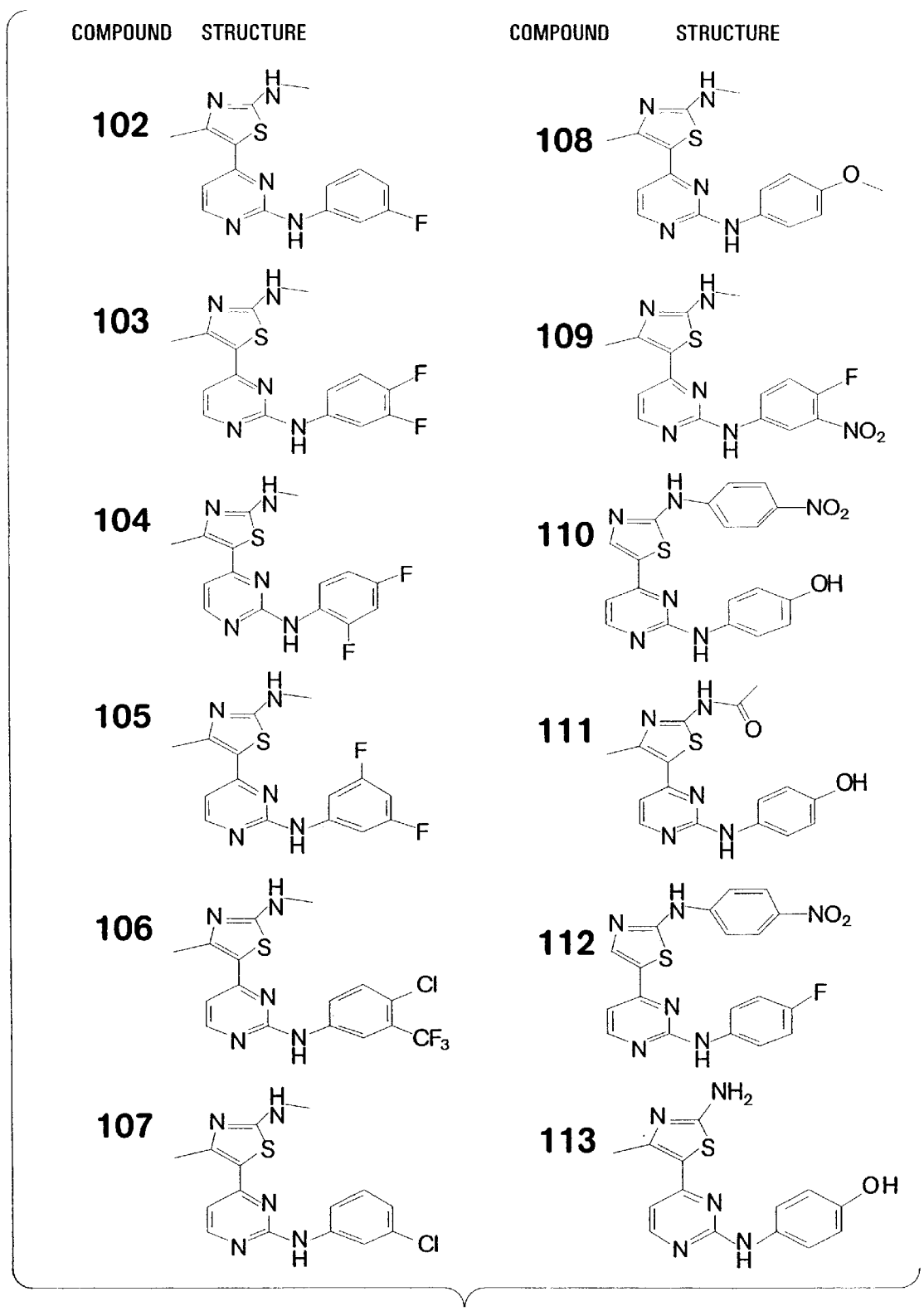
Figures 1, 2, 3, 4, 5, 6, 7, 8, 9, 10:
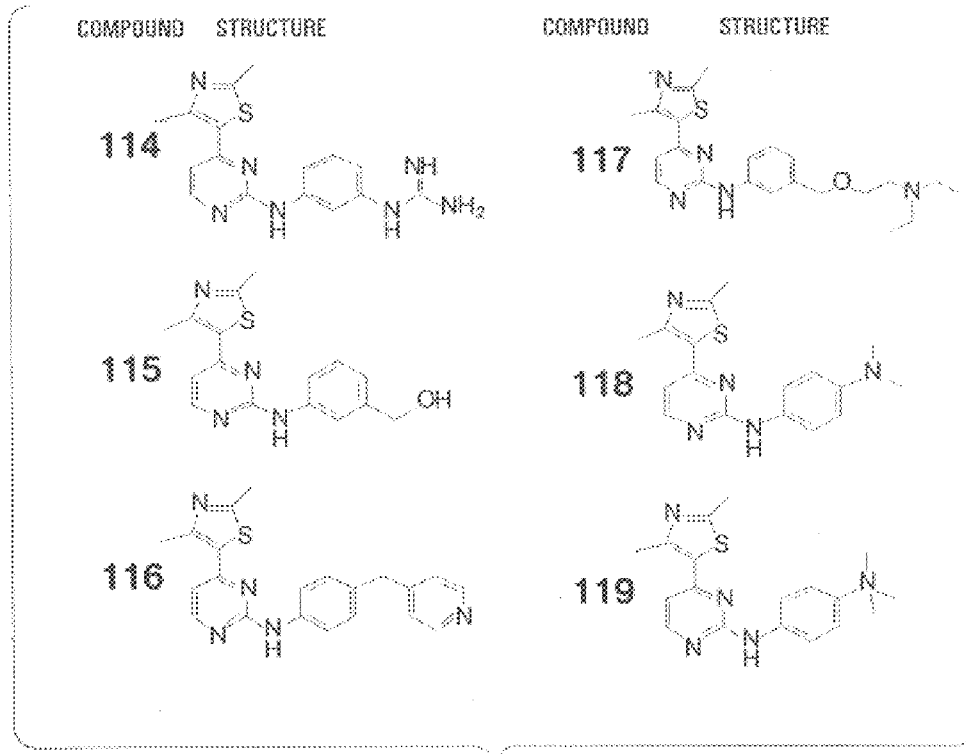
Figure 2:
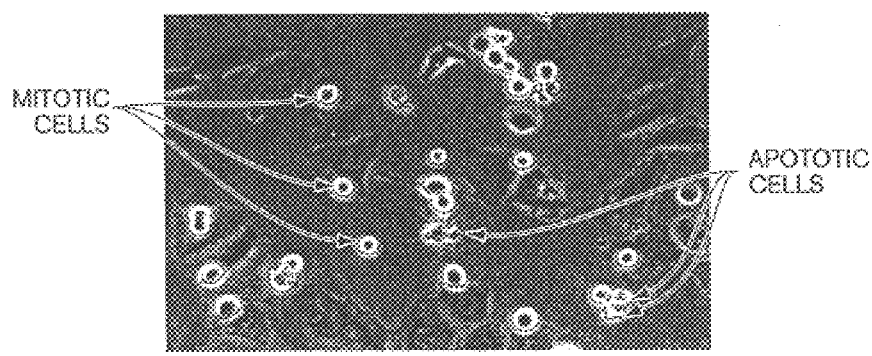
Figures 3A, 3B:
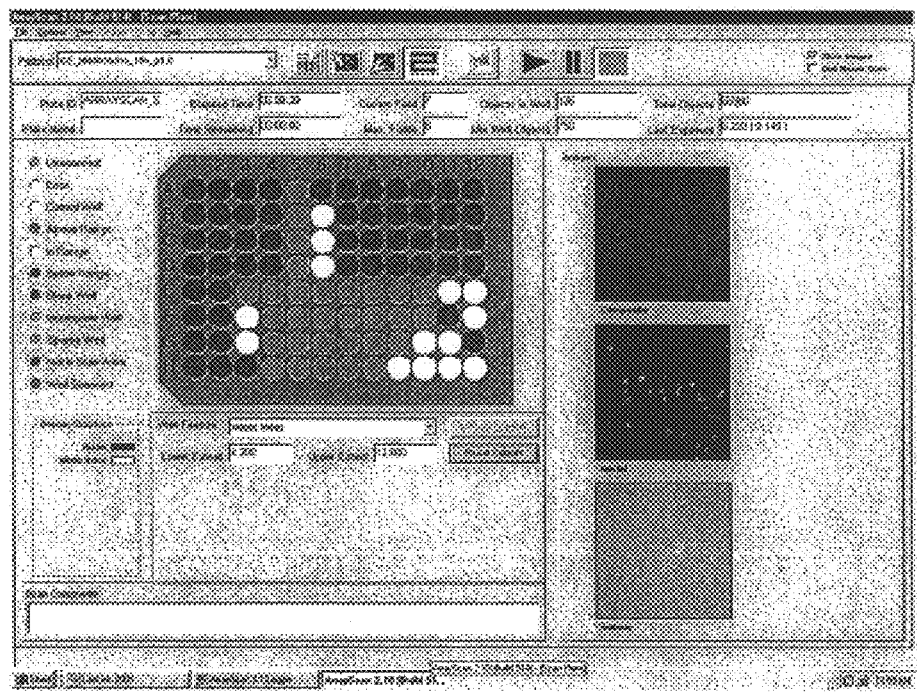
FIG. 3A shows the plate plan and FIG. 3B shows the image from the scan plate window. (The plates shaded in black are "below range." The plates shaded in dark gray are "above range." The plates shaded in light gray are "in range.")
Figure 4A:
FIG. 4A—Compound 28, 4.4 μM Hoechst stain for nuclei
Figure 4B:
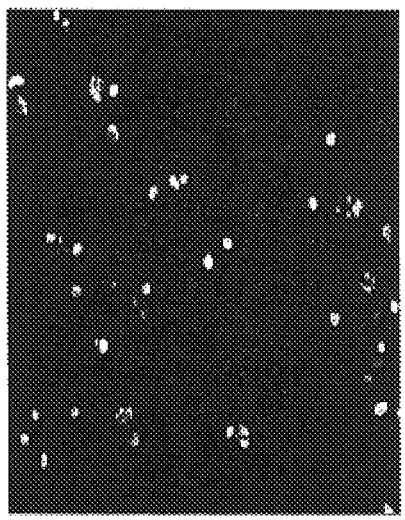
FIG. 4B—Compound 28, 4.4 μM anti mitotic stain
Figure 4C:
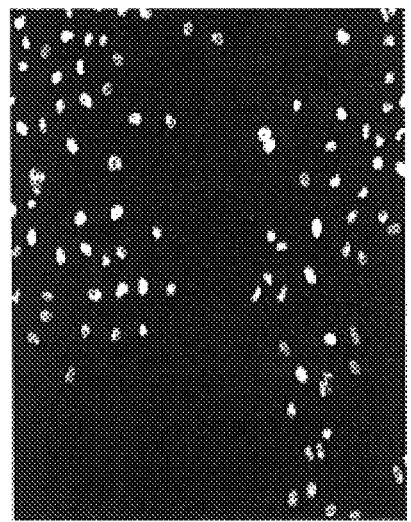
FIG. 4C—Control cells, Hoechst stain for nuclei
Figure 4D:
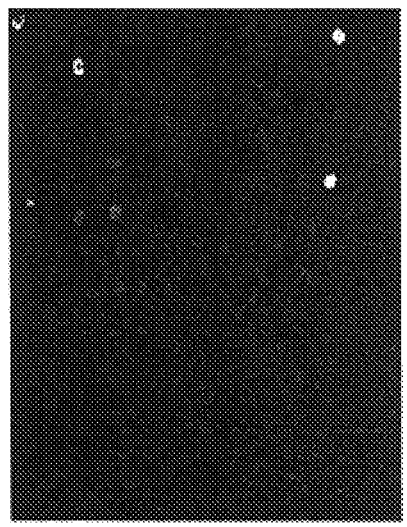
FIG. 4D—Control cells, anti mitotic stain
Figure 5:
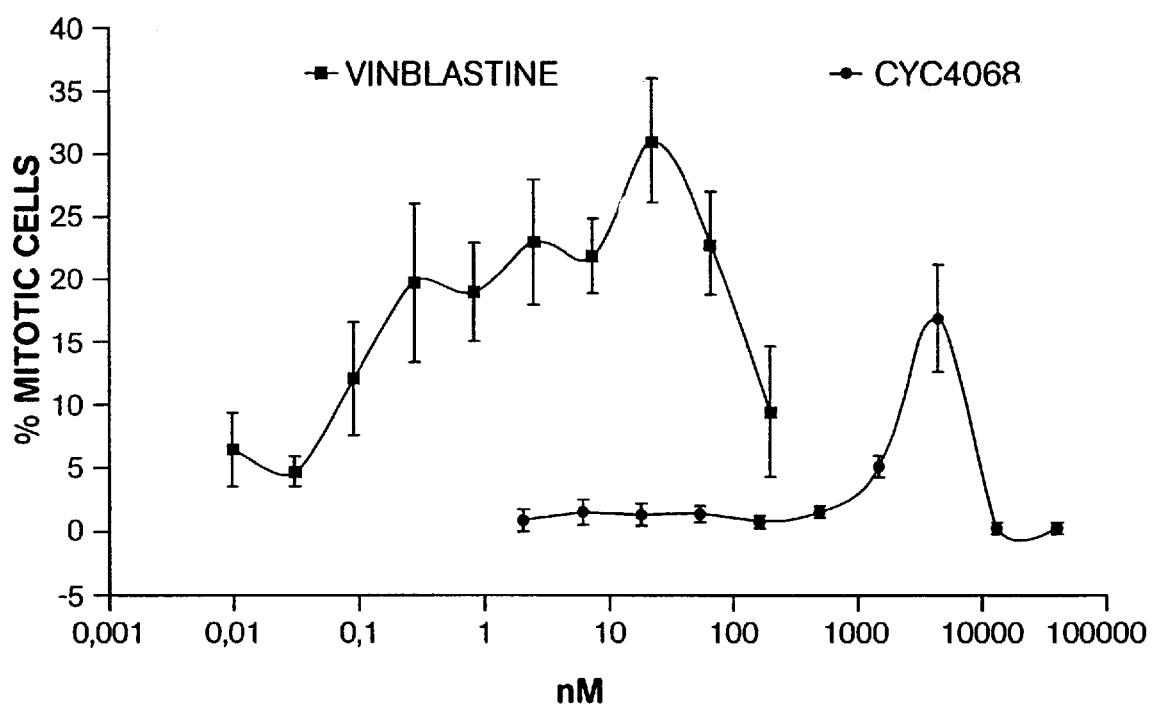
Figure 6A:
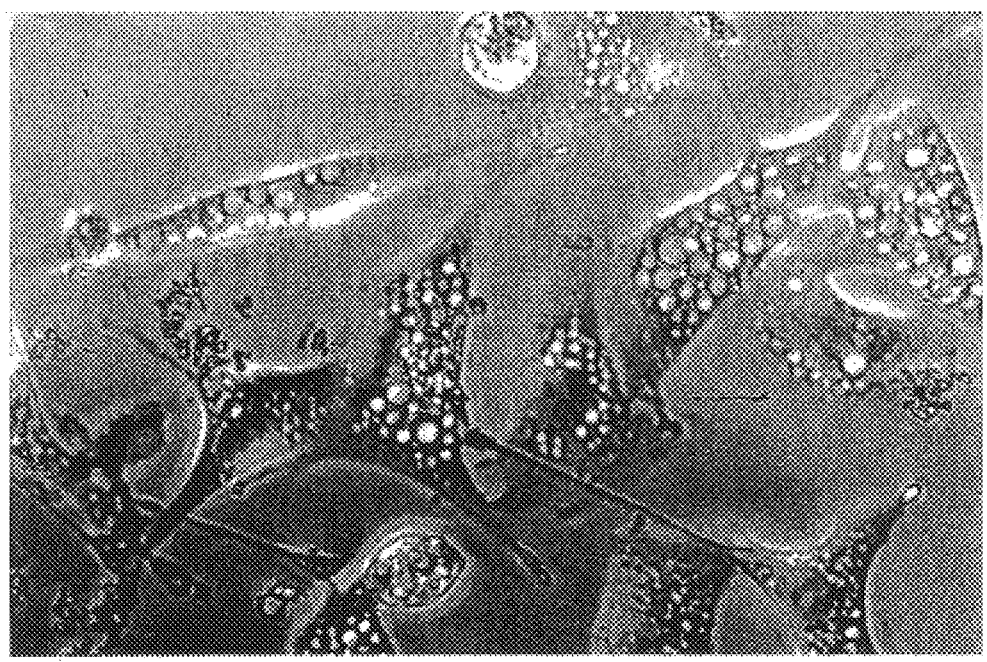
Figure 6B:
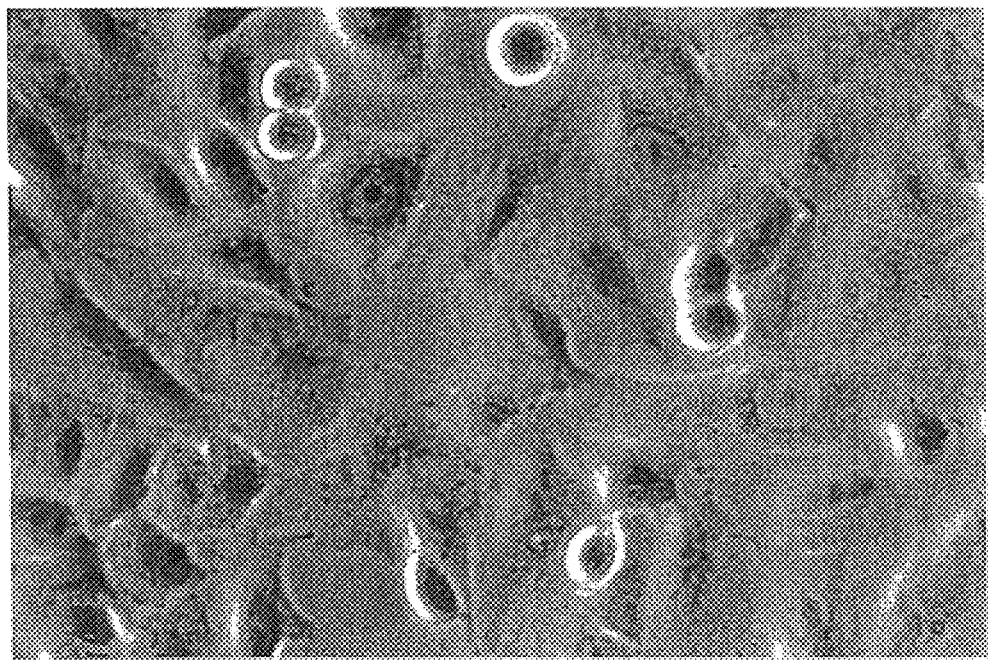

In addition to the induction of apoptosis some of the compounds of the invention are capable of inducing forms of programmed cell death that is distinct from apoptosis by the criteria of morphology. The induction of programmed cell death by compound 28, characterised by cytoplasmic vaculation, is shown in FIG. 6. Human lung carcinoma cells (A549) were treated for 16 h with 10 μM compound 28. Extensive cytoplasmic vaculation is observed in the treated cell (A) but not in the control cells (B).

What is claimed is:

1. A compound of general formula I:

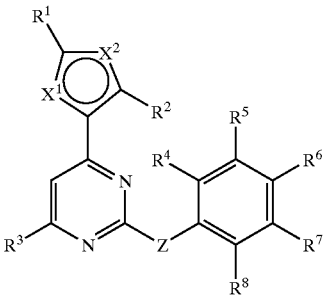

wherein
one of $X^1$ and $X^2$ is S, and the other of $X^1$ and $X^2$ is N;
Z is NH, NHCO, NHSO$_2$, NHCH$_2$, CH$_2$, CH$_2$CH$_2$, or CH=CH;
$R^1$, $R^2$, and $R^3$ are independently H, alkyl, aryl, aralkyl, heterocycle, halogen, NO$_2$, CN, OH, alkoxy, aryloxy, NH$_2$, NH—R', N—(R')(R"), NH—COR', NH-aryl, N-(aryl)$_2$, COOH, COO—R', COO-aryl, CONH$_2$, CONH—R', CON—(R')(R"), CONH-aryl, CON-(aryl)$_2$, SO$_3$H, SO$_2$NH$_2$, CF$_3$, CO—R', or CO-aryl, wherein alkyl, aryl, aralkyl, heterocycle and NH-aryl groups may be further substituted with one or more groups selected from halogen, NO$_2$, CN, OH, O-methyl, NH$_2$, COOH, CONH$_2$ and CF$_3$; at least one of the groups $R^1$ and $R^2$ being other than H when either $X^1$ or $X^2$ is S;
$R^4$, $R^5$, $R^6$, $R^7$, and $R^8$ are independently from each other H, substituted or unsubstituted lower alkyl, halogen, amino, carbamoyl, sulfamyl, NO$_2$, CN, OH, substituted or unsubstituted alkoxy, NH$_2$, NH—R', alkyl-aryl, alkyl-heteroaryl, NH(C=NH)NH$_2$, N(R')$_3^+$, N—(R')(R"), COOH, COO—R', CONH$_2$, CONH—R', CON—(R') (R"), SO$_3$H, SO$_2$NH$_2$, CF$_3$ or (CH$_2$)$_n$O(CH$_2$)$_m$NR'R", (CH$_2$)$_n$CO$_2$(CH$_2$)$_m$OR'" wherein n is 0, 1, 2 or 3 and m is 1, 2 or 3;
wherein R', R" and R'" are each independently alkyl groups that may be the same or different;
and pharmaceutically acceptable salts thereof.

2. A compound according to claim 1, wherein
$X^1$ and $X^2$ are S and N respectively;
$R^1$, $R^2$ and $R^3$ are each independently selected from the group consisting of: H, alkyl, aryl, aralkyl, halogen, NO$_2$, CN, OH, alkoxy, aryloxy, NH$_2$, NHCOR', NHCOR', NH-aryl, NH—R', N—(R')(R"), COOH, COO—R', CONH$_2$, CONH—R', CON—(R')(R"), SO$_3$H, SO$_2$NH$_2$, CF$_3$, and CO—R' wherein alkyl, aryl, NH-aryl and aralkyl groups may be further substituted with one or more groups selected from halogen, NO$_2$, CN, OH, O-methyl, NH$_2$, COOH, CONH$_2$ and CF$_3$;
Z is selected from the group consisting of: NH, NHSO$_2$ and NHCH$_2$;
$R^4$, $R^5$, $R^6$, $R^7$, and $R^8$ are each independently selected from the group consisting of: H, OH, halogen, nitro, amino, alkoxy, carbamoyl, sulfamyl, C$_{1-4}$ alkyl, substituted C$_{1-4}$ alkyl, COOH, COOR', CN, CF$_3$, (CH$_2$)$_n$O(CH$_2$)$_m$NR'R", alkyl-aryl, alkyl-heteroaryl, NH(C=NH)NH$_2$, N(R')$_3^-$, N(R')(R") and (CH$_2$)$_n$CO$_2$(CH$_2$)$_m$OR'".

3. A compound according to claim 1, wherein $X^1$ and $X^2$ are S and N respectively.

4. A compound according to claim 1, 2, or 3, wherein Z is NH and $R^3$ is H.

5. A compound according to claim 1, 2, or 3, wherein $R^1$ and $R^2$ are each independently one or more of halogen, a $C_{1-4}$ alkyl group, H, aryl, heterocycle or NH(R').

6. A compound according to claim 5, wherein $R^1$ and $R^2$ are chloro or methyl.

7. A compound according to claim 1, 2, or 3, wherein $R^3$ is selected from the group consisting of: H, aryl, substituted aryl, halogen, $C_{1-4}$ alkoxy and OH.

8. A compound according to claim 1, 2, or 3, wherein $R^4$, $R^5$, $R^6$, $R^7$, and $R^8$ are selected independently from the group consisting of: F, $NH_2$, $NO_2$, OH, Cl, Br, I, $CF_3$, OMe, COOH, COOR', CN, H, $C_{1-4}$ alkyl, $C_{1-4}$ alkoxy, $CH_2CO_2CH_2CH_2OMe$, $NH(C=NH)NH_2$, and $CO_2CH_2CH_2OMe$, $CH_2OCH_2CH_2NEt_2$, $CH_2$-heteroaryl, $NMe_3^+$, $NMe_2$.

9. A compound according to claim 1 selected from the group consisting of:
2-{N-(phenyl)}-4-(2,4-dimethylthiazol-5-yl)pyrimidineamines in which the phenyl group is 2-, 3- or 4-substituted by at least one of Me, F, $NH_2$, $NO_2$, OH, Cl, Br, I, $CF_3$, OMe, CN, COOH, $CH_2OH$, COOMe, COOEt, $NH(C=NH)NH_2$, $CH_2CO_2CH_2CH_2OMe$, $CH_2$-pyridyl, $CH_2OCH_2CH_2NEt_2$, $CO_2CH_2CH_2OMe$, $NMe_3^+$ and $NMe_2$.

10. A compound according to claim 9, wherein the phenyl group is mono-substituted by F, $NH_2$, $NO_2$, OH, Cl, Br, I, $CF_3$, OMe, CN, $CH_2OH$, COOH, COOMe, COOEt, $CH_2CO_2CH_2CH_2OMe$ or $CO_2CH_2CH_2OMe$ at any of the 2, 3 or 4-positions, or di-substituted by 2,4-difluoro, 3,5-difluoro, 3,4-difluoro, 2,4-dichloro, 3,5-dichloro, 3,4-dichloro, 4-hydroxy-2-nitro, 4-hydroxy-3-nitro, 6-chloro-3-carboxy, 4-chloro-3-carboxy, 6-chloro-2-carboxy, 2-fluoro-4-iodo, 2-hydroxy-4-methoxy, 3-chloro-4-iodo, 3-chloro-4-hydroxy, 3-chloro-4-methyl, 3-chloro-4-methoxy, 4-fluoro-3-nitro, 6-chloro-3-methoxycarbonyl, 3-chloro-4-methoxcarbonyl, 3-chloro-4-ethoxcarbonyl, 2-hydroxy-4-methoxy, 2-chloro-5-methoxycarbonyl, 4-chloro-3-methoxycarbonyl, 6-chloro-3-($CO_2CH_2CH_2OMe$), 3-chloro-4-($CO_2CH_2CH_2OMe$), 4-chloro-3-trifluoromethyl, or 3-($CO_2CH_2CH_2OMe$)-4-fluoro.

11. A compound according to claim 9 wherein for group (a) the phenyl group is monosubstituted by Br, I or $CF_3$.

12. A compound according to claim 1 selected from the group consisting of
(2-Chloro-phenyl)-{4-(2,4-dimethyl-thiazol-5-yl)-pyrimidin-2-yl}-amine,
(4-Chloro-phenyl)-{4-(2,4-dimethyl-thiazol-5-yl)-pyrimidin-2-yl}-amine,
(3-Chloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-nitrophenyl)-amine,
{4-(2,4-Dimethyl-thiazol-5-yl)-pyrimidin-2-yl}-(3-nitrophenyl)-amine,
{4-(2,4-Dimethyl-thiazol-5-yl)-pyrimidin-2-yl}-(4-nitrophenyl)-amine,
{4-(2,4-Dimethyl-thiazol-5-yl)-pyrimidin-2-yl}-(2-fluorophenyl)-amine,
{4-(2,4-Dimethyl-thiazol-5-yl)-pyrimidin-2-yl}-(4-fluorophenyl)-amine,
(2,4-Difluoro-phenyl)-{4-(2,4-dimethyl-thiazol-5-yl)-pyrimidin-2-yl}-amine,
(3,5-Difluoro-phenyl)-{4-(2,4-dimethyl-thiazol-5-yl)-pyrimidin-2-yl}-amine,
(3,5-Dichloro-phenyl)-{4-(2,4-dimethyl-thiazol-5-yl)-pyrimidin-2-yl}-amine,
(2,4-Dichloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-trifluoromethyl-phenyl)-amine,
{4-(2,4-Dimethyl-thiazol-5-yl)-pyrimidin-2-yl}-(2-trifluoromethyl-phenyl)-amine,
{4-(2,4-Dimethyl-thiazol-5-yl)-pyrimidin-2-yl}-(4-trifluoromethyl-phenyl)-amine,
(2-Bromo-phenyl)-{4-(2,4-dimethyl-thiazol-5-yl)-pyrimidin-2-yl}-amine,
(3-Bromo-phenyl)-{4-(2,4-dimethyl-thiazol-5-yl)-pyrimidin-2-yl}-amine,
(4-Bromo-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-iodo-phenyl)-amine,
{4-(2,4-Dimethyl-thiazol-5-yl)-pyrimidin-2-yl}-(3-iodo-phenyl)-amine,
{4-(2,4-Dimethyl-thiazol-5-yl)-pyrimidin-2-yl}-(4-iodo-phenyl)-amine,
{4-(2,4-Dimethyl-thiazol-5-yl)-pyrimidin-2-yl}-pyridin-2-yl-amine,
{4-(2,4-Dimethyl-thiazol-5-yl)-pyrimidin-2-yl}-(3-fluoro-phenyl)-amine,
(3,4-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-methoxy-phenyl)-amine,
{4-(2,4-Dimethyl-thiazol-5-yl)-pyrimidin-2-yl}-(3-methoxy-phenyl)-amine,
{4-(2,4-Dimethyl-thiazol-5-yl)-pyrimidin-2-yl}-(4-methoxy-phenyl)-amine,
3-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-phenol,
N-{4-(2,4-Dimethyl-thiazol-5-yl)-pyrimidin-2-yl}-3-nitro-benzenesulfonamide,
4-Chloro-N-{4-(2,4-dimethyl-thiazol-5-yl)-pyrimidin-2-yl}-benzenesulfonamide,
N-{4-(2,4-Dimethyl-thiazol-5-yl)-pyrimidin-2-yl}-4-fluoro-benzenesulfonamide,
4-{4-(2,4-Dimethyl-thiazol-5-yl)-pyrimidin-2-ylamino}-2-nitro-phenol,
N-{4-(2,4-Dimethyl-thiazol-5-yl)-pyrimidin-2-yl}-4-nitro-benzenesulfonamide,
N-{4-(2,4-Dimethyl-thiazol-5-yl)-pyrimidin-2-yl}-benzene-1,3-diamine,
4-{4-(2,4-Dimethyl-thiazol-5-yl)-pyrimidin-2-ylamino}-benzonitrile,
3-{4-(2,4-Dimethyl-thiazol-5-yl)-pyrimidin-2-ylamino}-benzonitrile,
4-{4-(2,4-Dimethyl-thiazol-5-yl)-pyrimidin-2-ylamino}-benzoic acid methyl ester,
(3-Chloro-4-methyl-phenyl)-{4-(2,4-dimethyl-thiazol-5-yl)-pyrimidin-2-yl}-amine,
(3-Chloro-4-methoxy-phenyl)-{4-(2,4-dimethyl-thiazol-5-yl)-pyrimidin-2-yl}-amine,
4-{4-(2,4-Dimethyl-thiazol-5-yl)-pyrimidin-2-ylamino}-benzoic acid,
{4-Bromo-6-(2,4-dimethyl-thiazol-5-yl)-pyrimidin-2-yl}-(3-nitro-phenyl)-amine,
{4-(2,4-Dimethyl-thiazol-5-yl)-6-phenyl-pyrimidin-2-yl}-(3-nitro-phenyl)-amine,
4-{4-(2,4-Dimethyl-thiazol-5-yl)-6-phenyl-pyrimidin-2-ylamino}-phenol,
(3,4-Difluoro-phenyl)-{4-(4-methyl-2-phenyl-thiazol-5-yl)-pyrimidin-2-yl}-amine,
4-{4-(4-Methyl-2-phenyl-thiazol-5-yl)-pyrimidin-2-ylamino}-phenol, {4-(2,4-Dimethyl-thiazol-5-yl)-6-phenyl-pyrimidin-2-yl}-(4-fluoro-phenyl)-amine,
(4-Fluoro-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-phenol,
{4-(2,4-Dimethyl-thiazol-5-yl)-6-(4-trifluoromethyl-phenyl)-pyrimidin-2-yl}-(4-fluoro-phenyl)-amine,
(4-Chloro-phenyl)-{4-(2,4-dimethyl-thiazol-5-yl)-6-(4-trifluoromethyl-phenyl)-pyrimidin-2-yl}-amine,
4-{4-(2,4-Dimethyl-thiazol-5-yl)-6-(4-trifluoromethyl-phenyl)-pyrimidin-2-ylamino}-2-nitro-phenol,
(4-Fluoro-phenyl)-{4-(4-methyl-2-pyridin-3-yl-thiazol-5-yl)-pyrimidin-2-yl}-amine,
{4-(2,4-Dimethyl-thiazol-5-yl)-6-(3-trifluoromethyl-phenyl)-pyrimidin-2-yl}-(4-fluoro-phenyl)-amine,
4-{6-(2,4-Dimethyl-thiazol-5-yl)-2-(4-fluoro-phenylamino)-pyrimidin-4-yl}-2,6-dimethoxy-phenol,
4-{6-(2,4-Dimethyl-thiazol-5-yl)-2-(4-fluoro-phenylamino)-pyrimidin-4-yl}-phenol,
{4-(4-Methyl-2-pyridin-3-yl-thiazol-5-yl)-pyrimidin-2-yl}-(3-nitro-phenyl)-amine,
(4-Iodo-phenyl)-{4-(4-methyl-2-methylamino-thiazol-5-yl)-pyrimidin-2-yl}-amine,
4-{2-Amino-6-(2,4-dimethyl-thiazol-5-yl)-pyrimidin-4-yl}-2,6-dimethoxy-phenol,
4-{4-(4-Methyl-2-methylamino-thiazol-5-yl)-pyrimidin-2-ylamino}-2-nitro-phenol,
2-Chloro-4-{4-(4-methyl-2-methylamino-thiazol-5-yl)-pyrimidin-2-ylamino}-benzoic acid ethyl ester,
{4-(2-Ethylamino-4-methyl-thiazol-5-yl)-pyrimidin-2-yl}-(4-fluoro-phenyl)-amine,
{4-(4Methyl-2-methylamino-thiazol-5-yl)-pyrimidin-2-yl}-(3-nitro-phenyl)-amine,
3-{4-(2-Ethylamino-4-methyl-thiazol-5-yl)-pyrimidin-2-ylamino}-phenol,
2-Chloro-4-{4-(2-ethylamino-4-methyl-thiazol-5-yl)-pyrimidin-2-ylamino}-benzoic acid ethyl ester,
4-Chloro-3-{4-(2,4-dimethyl-thiazol-5-yl)-pyrimidin-2-ylamino}-benzoic acid 2-methoxy-ethyl ester,
2-Chloro-4-{4-(2,4-dimethyl-thiazol-5-yl)-pyrimidin-2-ylamino}-benzoic acid 2-methoxy-ethyl ester,
4-Chloro-3-{4-(2,4-dimethyl-thiazol-5-yl)-pyrimidin-2-ylamino}-benzoic acid,
2-Chloro-5-{3-(2,4-dimethyl-thiazol-5-yl)-phenylamino}-benzoic acid,
{4-(2-Allylamino-4-methylthiazol-5-yl)-pyrimidin-2-yl}-(4-fluoro-phenyl)-amine,
(3-Bromo-phenyl)-{4-(4-methyl-2-methylamino-thiazol-5-yl)-pyrimidin-2-yl}-amine,
{4-(2-Allylamino-4-methyl-thiazol-5-yl)-pyrimidin-2-yl}-(3-nitro-phenyl)-amine,
3-{4-(4-Methyl-2-methylamino-thiazol-5-yl)-pyrimidin-2-ylamino}-phenol,
(4-Bromo-phenyl)-{4-(4-methyl-2-methylamino-thiazol-5-yl)-pyrimidin-2-yl}-amine,
(4-Chloro-phenyl)-{4-(4-methyl-2-methylamino-thiazol-5-yl)-pyrimidin-2-yl}-amine,
(3-Methoxy-phenyl)-{4-(4-methyl-2-methylamino-thiazol-5-yl)-pyrimidin-2-yl}-amine,
{4-(4-Methyl-2-methylamino-thiazol-5-yl)-pyrimidin-2-yl}-(4-trifluoromethyl-phenyl)-amine,
{4-(4-Methyl-2-methylamino-thiazol-5-yl)-pyrimidin-2-yl}-(3trifluoromethyl-phenyl)-amine,
{4-(2-Allylamino-4-methyl-thiazol-5-yl)-pyrimidin-2-yl}-(3-nitro-phenyl)-amine,
2-Chloro-5-{4-(2,4-dimethyl-thiazol-5-yl)-pyrimidin-2-ylamino}-benzoic acid ethyl ester,
3-Chloro-2-{4-(2,4-dimethyl-thiazol-5-yl)-pyrimidin-2-ylamino}-benzoic acid ethyl ester,
{4-(2,4-Dimethyl-thiazol-5-yl)-pyrimidin-2-yl}-(2-fluoro-4-iodo-phenyl)-amine,
2-{4-(2,4-Dimethyl-thiazol-5-yl)-pyrimidin-2-ylamino}-5-methoxy-phenol,
(3-Chloro-4-iodo-phenyl)-{4-(2,4-dimethyl-thiazol-5-yl)-pyrimidin-2-yl}-amine,
2-Chloro-4-{4-(2,4-dimethyl-thiazol-5-yl)-pyrimidin-2-ylamino}-phenol,
5-{4-(2,4-Dimethyl-thiazol-5-yl)-pyrimidin-2-ylamino}-2-fluoro-benzoic acid 2-methoxy-ethyl ester,
2-Chloro-5-{4-(2,4-dimethyl-thiazol-5-yl)-pyrimidin-2-ylamino}-benzoic acid methyl ester,
4-Chloro-3-{4-(2,4-dimethyl-thiazol-5-yl)-pyrimidin-2-ylamino}-benzoic acid methyl ester,
2-Chloro-4-{4-(2,4-dimethyl-thiazol-5-yl)-pyrimidin-2-ylamino}-benzoic acid methyl ester,
(3-Iodo-phenyl)-{4-(4-methyl-2-methylamino-thiazol-5-yl)-pyrimidin-2-yl}-amine,
(3-Fluoro-phenyl)-{4-(4-methyl-2-methylamino-thiazol-5-yl)-pyrimidin-2-yl}-amine,
(3,4-Difluoro-phenyl)-{4-(4-methyl-2-methylamino-thiazol-5-yl)-pyrimidin-2-yl}-amine,
(2,4-Difluoro-phenyl)-{4-(4-methyl-2-methylamino-thiazol-5-yl)-pyrimidin-2-yl}-amine,
(3,5-Difluoro-phenyl)-{4-(4-methyl-2-methylamino-thiazol-5-yl)-pyrimidin-2-yl}-amine,
(4-Chloro-3-trifluoromethyl-phenyl)-{4-(4-methyl-2-methylamino-thiazol-5-yl)-pyrimidin-2-yl}-amine,
(3-Chloro-phenyl)-{4-(4-methyl-2-methylamino-thiazol-5-yl)-pyrimidin-2-yl}-amine,
(4-Methoxy-phenyl)-{4-(4-methyl-2-methylamino-thiazol-5-yl)-pyrimidin-2-yl}-amine,
(4-Fluoro-3-nitro-phenyl)-{4-(4-methyl-2-methylamino-thiazol-5-yl)-pyrimidin-2-yl}-amine,
4-{4-{2-(4-Nitro-phenylamino)-thiazol-5-yl}-pyrimidin-2-ylamino}-phenol,
N-{5-{2-(4-Hydroxy-phenylamino)-pyrimidin-4-yl}-4-methyl-thiazol-2-yl}-acetamide,
(4-Fluoro-phenyl)-{4-{2-(4-nitro-phenylamino)-thiazol-5-yl}-pyrimidin-2-yl}-amine,
4-{4-(2-Amino-4-methyl-thiazol-5-yl)-pyrimidin-2-ylamino}-phenol,
N-{3-{4-(2,4-Dimethyl-thiazol-5-yl)-pyrimidin-2-ylamino}-phenyl}-guanidine,
{3-{4-(2,4-Dimethyl-thiazol-5-yl)-pyrimidin-2-ylamino}-phenyl}-methanol,
{4-(2,4-Dimethyl-thiazol-5-yl)-pyrimidin-2-yl}-(4-pyridin-4-ylmethyl-phenyl)-amine,
{3-(2-Diethylamino-ethoxymethyl)-phenyl}-{4-(2,4-dimethyl-thiazol-5-yl)-pyrimidin-2-yl}-amine,
N,N-Dimethyl-N'-{4-(2,4-dimethyl-thiazol-5-yl)-pyrimidin-2-yl}-benzene-1,4-diamine, and
{4-{4-(2,4-Dimethyl-thiazol-5-yl)-pyrimidin-2-ylamino}-phenyl}-trimethyl-ammonium.

13. A compound according to claim 1 selected from the group consisting of:
(4-Chloro-phenyl)-{4-(2,4-dimethyl-thiazol-5-yl)-pyrimidin-2-yl}-amine,
(3-Chloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-nitro-phenyl)-amine,
{4-(2,4-Dimethyl-thiazol-5-yl)-pyrimidin-2-yl}-(4-nitro-phenyl)-amine,
{4-(2,4-Dimethyl-thiazol-5-yl)-pyrimidin-2-yl}-(2-fluoro-phenyl)-amine, {4-(2,4-Dimethyl-thiazol-5-yl)-pyrimidin-2-yl}-(4-fluoro-phenyl)-amine,
(2,4-Difluoro-phenyl)-{4-(2,4-dimethyl-thiazol-5-yl)-pyrimidin-2-yl}-amine,
(3,5-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(4-trifluoromethyl-phenyl)-amine,
(3-Bromo-phenyl)-{4-(2,4-dimethyl-thiazol-5-yl)-pyrimidin-2-yl}-amine,
(4-Bromo-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-iodo-phenyl)-amine,
{4-(2,4-Dimethyl-thiazol-5-yl)-pyrimidin-2-yl}-(3-fluoro-phenyl)-amine,
(3,4-Difluoro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(2-methoxy-phenyl)-amine,
{4-(2,4-Dimethyl-thiazol-5-yl)-pyrimidin-2-yl}-(3-methoxy-phenyl)-amine,
{4-(2,4-Dimethyl-thiazol-5-yl)-pyrimidin-2-yl}-(4-methoxy-phenyl)-amine,
3-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-phenol,
4-{4-(2,4-Dimethyl-thiazol-5-yl)-pyrimidin-2-ylamino}-2-nitro-phenol,
N-{4-(2,4-Dimethyl-thiazol-5-yl)-pyrimidin-2-yl}-benzene-1,3-diamine,
4-{4-(2,4-Dimethyl-thiazol-5-yl)-pyrimidin-2-ylamino}-benzonitrile,
3-{4-(2,4-Dimethyl-thiazol-5-yl)-pyrimidin-2-ylamino}-benzonitrile,
4-{4-(2,4-Dimethyl-thiazol-5-yl)-pyrimidin-2-ylamino}-benzoic acid methyl ester,
(3-Chloro-4-methyl-phenyl)-{4-(2,4-dimethyl-thiazol-5-yl)-pyrimidin-2-yl}-amine,
(3-Chloro-4-methoxy-phenyl)-{4-(2,4-dimethyl-thiazol-5-yl)-pyrimidin-2-yl}-amine,
4-{4-(2,4-Dimethyl-thiazol-5-yl)-pyrimidin-2-ylamino}-benzoic acid,
{4-Bromo-6-(2,4-dimethyl-thiazol-5-yl)-pyrimidin-2-yl}-(3-nitro-phenyl)-amine,
4-{4-(4-Methyl-2-phenyl-thiazol-5-yl)-pyrimidin-2-ylamino}-phenol,
(4-Fluoro-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-phenol,
(4-Iodo-phenyl)-{4-(4-methyl-2-methylamino-thiazol-5-yl)-pyrimidin-2-yl}-amine,
4-{4-(4-Methyl-2-methylamino-thiazol-5-yl)-pyrimidin-2-ylamino}-2-nitro-phenol,
2-Chloro-4-{4-(4-methyl-2-methylamino-thiazol-5-yl)-pyrimidin-2-ylamino}-benzoic acid ethyl ester,
{4-(2-Ethylamino-4-methyl-thiazol-5-yl)-pyrimidin-2-yl}-(4-fluoro-phenyl)-amine,
{4-(4-Methyl-2-methylamino-thiazol-5-yl)-pyrimidin-2-yl}-(3-nitro-phenyl)-amine,
{4-(2-Allylamino-4-methyl-thiazol-5-yl)-pyrimidin-2-yl}-(4-fluoro-phenyl)-amine,
(3-Bromo-phenyl)-{4-(4-methyl-2-methylamino-thiazol-5-yl)-pyrimidin-2-yl}-amine,
{4-(2-Allylamino-4-methyl-thiazol-5-yl)-pyrimidin-2-yl}-(3-nitro-phenyl)-amine,
3-{4-(4-Methyl-2-methylamino-thiazol-5-yl)-pyrimidin-2-ylamino}-phenol,
(4-Bromo-phenyl)-{4-(4-methyl-2-methylamino-thiazol-5-yl)-pyrimidin-2-yl}-amine,
(4-Chloro-phenyl)-{4-(4-methyl-2-methylamino-thiazol-5-yl)-pyrimidin-2-yl}-amine,
(3-Methoxy-phenyl)-{4-(4-methyl-2-methylamino-thiazol-5-yl)-pyrimidin-2-yl}-amine,
{4-(4-Methyl-2-methylamino-thiazol-5-yl)-pyrimidin-2-yl}-(4-trifluoromethyl-phenyl)-amine,
{4-(4-Methyl-2-methylamino-thiazol-5-yl)-pyrimidin-2-yl}-(3-trifluoromethyl-phenyl)-amine,
5-{4-(2,4-Dimethyl-thiazol-5-yl)-pyrimidin-2-ylamino}-2-fluoro-benzoic acid 2-methoxy-ethyl ester,
2-Chloro-5-{4-(2,4-dimethyl-thiazol-5-yl)-pyrimidin-2-ylamino}-benzoic acid methyl ester,
(3,5-Difluoro-phenyl)-{4-(4-methyl-2-methylamino-thiazol-5-yl)-pyrimidin-2-yl}-amine,
(4-Chloro-3-trifluoromethyl-phenyl)-{4-(4-methyl-2-methylamino-thiazol-5-yl)-pyrimidin-2-yl}-amine,
(3-Chloro-phenyl)-{4-(4-methyl-2-methylamino-thiazol-5-yl)-pyrimidin-2-yl}-amine,
(4-Methoxy-phenyl)-{4-(4-methyl-2-methylamino-thiazol-5-yl)-pyrimidin-2-yl}-amine,
2-{4-(2,4-Dimethyl-thiazol-5-yl)-pyrimidin-2-ylamino}-5-methoxy-phenol,
(3-Fluoro-phenyl)-{4-(4-methyl-2-methylamino-thiazol-5-yl)-pyrimidin-2-yl}-amine,
(3,4-Difluoro-phenyl)-{4-(4-methyl-2-methylamino-thiazol-5-yl)-pyrimidin-2-yl}-amine,
N-{3-{4-(2,4-Dimethyl-thiazol-5-yl)-pyrimidin-2-ylamino}-phenyl}-guanidine,
{4-(2,4-Dimethyl-thiazol-5-yl)-pyrimidin-2-yl}-(4-pyridin-4-ylmethyl-phenyl)-amine,
N,N-Dimethyl-N'-{4-(2,4-dimethyl-thiazol-5-yl)-pyrimidin-2-yl}-benzene-1,4-diamine, and
{4-{4-(2,4-Dimethyl-thiazol-5-yl)-pyrimidin-2-ylamino}-phenyl}-trimethyl-ammonium.

14. A compound according to claim 1 selected from the following:
{4-(2,4-Dimethyl-thiazol-5-yl)-pyrimidin-2-yl}-(4-trifluoromethyl-phenyl)-amine,
(4-Bromo-phenyl)-{4-(2,4-dimethyl-thiazol-5-yl)-pyrimidin-2-yl}-amine,
4-{4-(4-Methyl-2-methylamino-thiazol-5-yl)-pyrimidin-2-ylamino}-phenol, and
(4-Fluoro-phenyl)-{4-(4-methyl-2-methylamino-thiazol-5-yl)-pyrimidin-2-yl}-amine.

15. A compound according to claim 1 selected from the group consisting of:
(3,5-Dichloro-phenyl)-{4-(2,4-dimethyl-thiazol-5-yl)-pyrimidin-2-yl}-amine,
(2,4-Dichloro-phenyl)-{4-(2,4-dimethyl-thiazol-5-yl)-pyrimidin-2-yl}-amine,
{4-(2,4-Dimethyl-thiazol-5-yl)-pyrimidin-2-yl}-(3-trifluoromethyl-phenyl)-amine,
{4-(2,4-Dimethyl-thiazol-5-yl)-pyrimidin-2-yl}-(2-trifluoromethyl-phenyl)-amine,
{4-(2,4-Dimethyl-thiazol-5-yl)-pyrimidin-2-yl}-(2-iodo-phenyl)-amine,
{4-(2,4-Dimethyl-thiazol-5-yl)-pyrimidin-2-yl}-(4-iodo-phenyl)-amine,
N-{4-(2,4-Dimethyl-thiazol-5-yl)-pyrimidin-2-yl}-3-nitro-benzenesulfonamide,
{4-(2,4-Dimethyl-thiazol-5-yl)-6-phenyl-pyrimidin-2-yl}-(3-nitro-phenyl)-amine,
(3,4-Difluoro-phenyl)-{4-(4-methyl-2-phenyl-thiazol-5-yl)-pyrimidin-2-yl}-amine, (4-Chloro-phenyl)-{4-(2,4-dimethyl-thiazol-5-yl)-6-(4-trifluoromethyl-phenyl)-pyrimidin-2-yl}-amine,
4-{6-(2,4-Dimethyl-thiazol-5-yl)-2-(4-fluoro-phenylamino)-pyrimidin-4-yl}-2,6-dimethoxy-phenol,
4-{6-(2,4-Dimethyl-thiazol-5-yl)-2-(4-fluoro-phenylamino)-pyrimidin-4-yl}-phenol,
2-Chloro-5-{4-(2,4-dimethyl-thiazol-5-yl)-pyrimidin-2-ylamino}-benzoic acid ethyl ester,
3-Chloro-2-{4-(2,4-dimethyl-thiazol-5-yl)-pyrimidin-2-ylamino}-benzoic acid ethyl ester,
{4-(2,4-Dimethyl-thiazol-5-yl)-pyrimidin-2-yl}-(2-fluoro-4-iodo-phenyl)-amine,
(3-Chloro-4-iodo-phenyl)-{4-(2,4-dimethyl-thiazol-5-yl)-pyrimidin-2-yl}-amine,
4-Chloro-3-{4-(2,4-dimethyl-thiazol-5-yl)-pyrimidin-2-ylamino}-benzoic acid methyl ester,
(3-Iodo-phenyl)-{4-(4-methyl-2-methylamino-thiazol-5-yl)-pyrimidin-2-yl}-amine, and
(2,4-Difluoro-phenyl)-{4-(4-methyl-2-methylamino-thiazol-5-yl)-pyrimidin-2-yl}-amine.

16. The compound of claim 1 that is {4-(2,4-Dimethyl-thiazol-5-yl)-pyrimidin-2-yl}-(4-iodo-phenyl)-amine.

17. The compound of claim 1, wherein said compound is selected from the group consisting of 2-{N-(phenyl)}-4-(4-methyl-2-methylamino-thiazol-5-yl)pyrimidineamines in which the phenyl group is 2-, 3- or 4-substituted by at least one of F, OH, I, $NO_2$, Cl, COOR', Br, OMe or $CF_3$.

18. The compound of claim 17, wherein the phenyl group is mono-substituted by chloro, bromo, iodo, fluoro, OH, nitro, $CF_3$ or OMe at any of the 2, 3 or 4 positions, or disubstituted by 4-hydroxy-3-nitro, 3-chloro-4-ethoxycarbonyl, 3,4-difluoro, 2,4-difluoro, 4-chloro-3-trifluoromethyl or 4-fluoro-3-nitro.

19. Pharmaceutical compositions comprising a compound as defined in claims 1, 2, or 3 or a pharmaceutically acceptable salt thereof together with a pharmaceutically acceptable excipient.

20. A method of treating a CDK dependent or sensitive disorder in a subject, comprising administering to the subject one or more compounds of claims 1, 2, or 3 or pharmaceutically acceptable salts thereof to the subject, thereby treating the CDK dependent or sensitive disorder in the subject, and wherein said compounds are administered in an amount sufficient to inhibit at least one CDK enzyme.

21. The method of claim 20, wherein the CDK dependent or sensitive disorder is cancer or leukemia.

22. The method of claim 20, wherein the CDK enzyme is CDK2 or CDK4.

23. The method of claim 21, wherein the CDK enzyme is CDK2 or CDK4.

* * * * *